(12) United States Patent
Lickert et al.

(10) Patent No.: US 11,733,236 B2
(45) Date of Patent: *Aug. 22, 2023

(54) FLATTOP (FLTP) IS A NOVEL BIOMARKER FOR BETA CELL MATURATION

(71) Applicant: Helmholtz Zentrum München—Deutsches Forschungszentrum Für Gesundheit Und Umwelt (GmbH), Neuherberg (DE)

(72) Inventors: Heiko Lickert, Munich (DE); Adriana Migliorini, Munich (DE); Moritz Gegg, Munich (DE); Erik Bader, Munich (DE)

(73) Assignee: Helmholtz Zentrum München—Deutsches Forschungszentrum Für Gesundheit Und Umwelt (GMBH), Neuherberg (DE)

( * ) Notice: Subject to any disclaimer, the term of this patent is extended or adjusted under 35 U.S.C. 154(b) by 882 days.

This patent is subject to a terminal disclaimer.

(21) Appl. No.: 16/683,994

(22) Filed: Nov. 14, 2019

(65) Prior Publication Data
US 2020/0141922 A1 May 7, 2020

Related U.S. Application Data

(63) Continuation of application No. 15/126,623, filed as application No. PCT/EP2015/056664 on Mar. 26, 2015, now Pat. No. 10,520,494.

(30) Foreign Application Priority Data

Mar. 26, 2014 (EP) ..................... 14161818

(51) Int. Cl.
| | | |
|---|---|---|
| G01N 33/50 | (2006.01) | |
| C12Q 1/6881 | (2018.01) | |
| G01N 33/569 | (2006.01) | |
| G01N 33/68 | (2006.01) | |
| A61K 38/17 | (2006.01) | |
| C12N 5/071 | (2010.01) | |

(52) U.S. Cl.
CPC ....... *G01N 33/507* (2013.01); *A61K 38/1709* (2013.01); *C12N 5/0676* (2013.01); *C12Q 1/6881* (2013.01); *G01N 33/56966* (2013.01); *G01N 33/6893* (2013.01); *C12N 2501/00* (2013.01); *C12N 2501/415* (2013.01); *C12N 2501/727* (2013.01); *C12Q 2600/158* (2013.01); *G01N 2800/042* (2013.01)

(58) Field of Classification Search
None
See application file for complete search history.

(56) References Cited

U.S. PATENT DOCUMENTS

2014/0329704 A1 11/2014 Melton et al.

FOREIGN PATENT DOCUMENTS

| JP | 2009511061 A | 3/2009 |
|---|---|---|
| JP | 2010500568 A | 1/2010 |
| JP | 2010150262 A | 7/2010 |
| JP | 2010222330 A | 10/2010 |
| WO | 2010104949 A2 † | 9/2010 |
| WO | WO-2015144861 A1 | 10/2015 |

OTHER PUBLICATIONS

Bader et al., "Identification of proliferative and mature β-cells in the islets of Langerhans," Nature, 535:430-450 (2016).
Blum et al., "Functional beta-cell maturation is marked by an increased glucose threshold and by expression of urocortin 3," Nature Biotechnology, 30(3):261-264 (2012).
Bouckenooghe et al., "Expression of progenitor cell markers during expansion of sorted human pancreatic beta cells," Gene Expression, 12(2): 83-98 (2005).

(Continued)

*Primary Examiner* — Daniel C Gamett
(74) *Attorney, Agent, or Firm* — Foley Hoag LLP; David P. Halstead

(57) ABSTRACT

The present invention relates to the use of the biomarker Flattop (Fltp) for distinguishing mature β cells from immature progenitor β cells. The present invention further relates to a method for distinguishing a mature β cell from an immature progenitor β cell, the method comprising: determining the presence or absence of the biomarker Flattop (Fltp) in a β cell; wherein the presence of Fltp in the cell indicates that the cell is a mature β cell and wherein the absence of Fltp in the cell indicates that the cell is an immature progenitor β cell. Furthermore, the present invention relates to a method of identifying a compound suitable for differentiating immature progenitor β cells into mature β cells as well as to a method of identifying a compound suitable for preventing the de-differentiating of mature β cells. The present invention additionally relates to a method of differentiating immature progenitor β cells into mature β cells as well as to a method of preventing de-differentiating of mature β cells. In addition, the present invention also relates to a kit for distinguishing mature β cells from immature progenitor β cells and to a pharmaceutical composition for use in treating or preventing diabetes.

19 Claims, 23 Drawing Sheets

Figure 1:
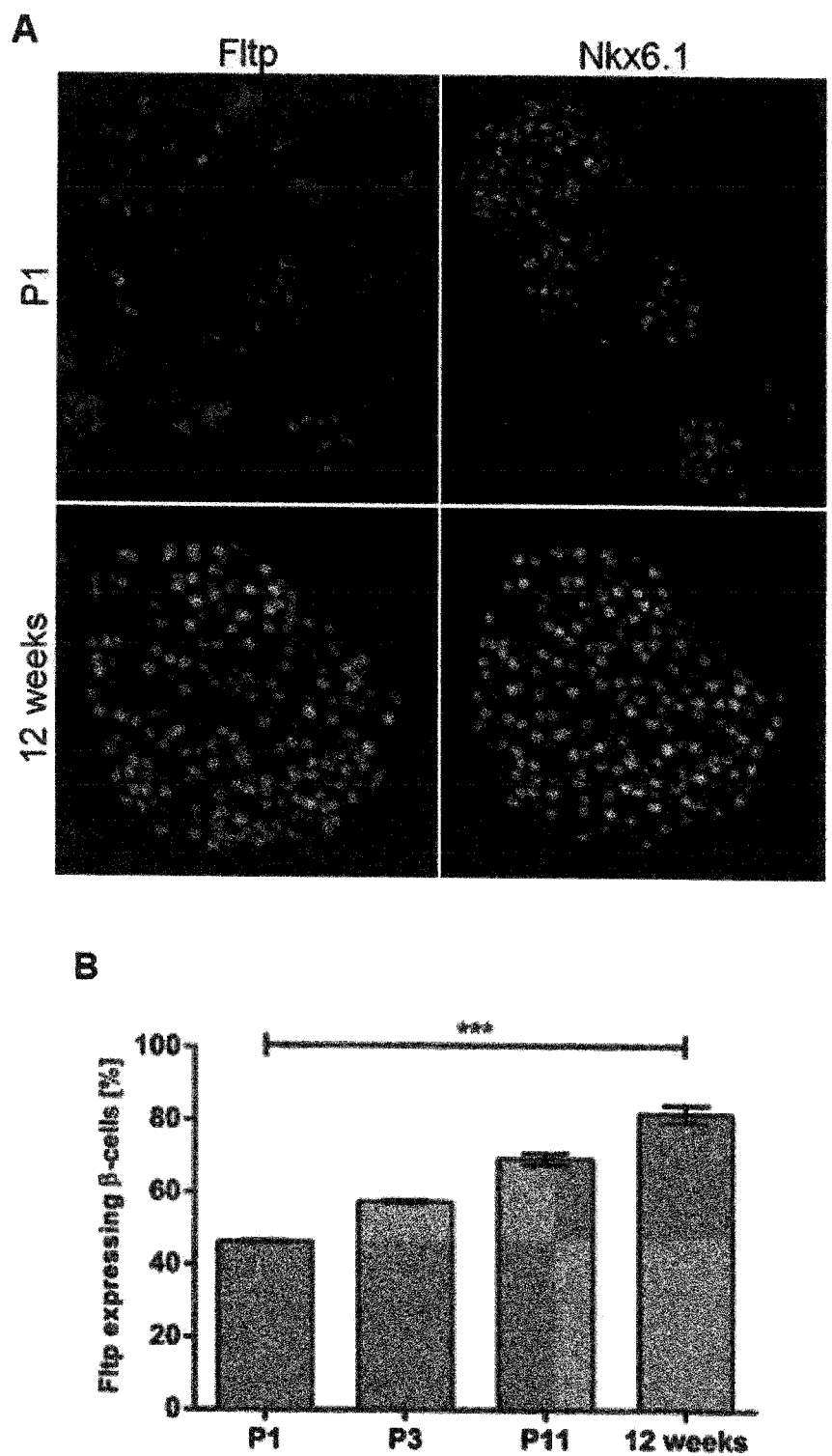
Figure 1:
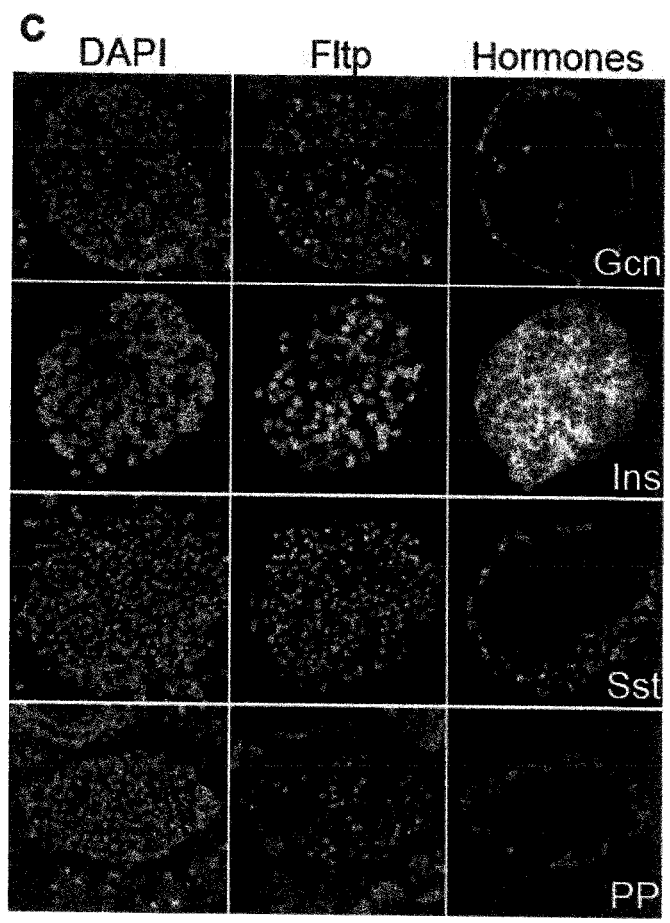
Figure 1:
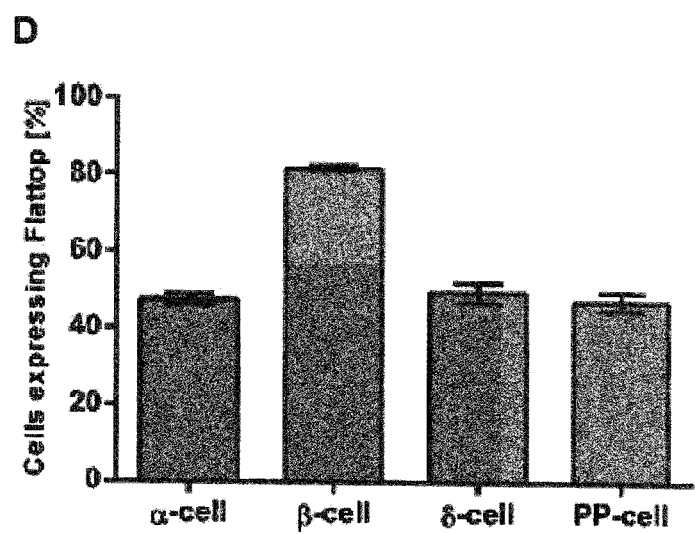

Specification includes a Sequence Listing.

(56) References Cited

OTHER PUBLICATIONS

Dor et al., "Adult pancreatic beta-cells are formed by self-duplication rather than stem-cell differentiation," Nature, 429(6987): 41-46 (2004).
Lange et al., "A new knock-in mouse line for conditional gene targeting in distinct mono- and multiciliated tissues," Differentiation, 83(2): S105-S113 (2011).
Jena et al., Redirecting T-cell specificity by introducing a tumor-specific chimeric antigen receptor, pp. 1035-1044, Aug. 19, 2010, Blood.†

† cited by third party

A

B

E

FLATTOP (FLTP) IS A NOVEL BIOMARKER FOR BETA CELL MATURATION

RELATED APPLICATIONS

This application is a continuation of U.S. patent application Ser. No. 15/126,623, filed on Sep. 16, 2016, which has received a Notice of Allowance on Aug. 7, 2019, and which is a US § 371 national stage of International Patent Application No. PCT/EP2015/056664, filed on Mar. 26, 2015 (published as WO 2015/144861 A1 on Oct. 1, 2015), which claims the benefit of priority to EP Patent Application No. 14161818.1, filed on Mar. 26, 2014. The contents of U.S. patent application Ser. No. 15/126,623 are hereby incorporated by reference in their entirety.

REFERENCE TO A SEQUENCE LISTING SUBMITTED VIA EFS-WEB

The contents of the ASCII text file of the sequence listing named SWH-00702-SL-ST25.txt, which is 20,584 bytes in size, which was created on Nov. 13, 2019, and which is being concurrently electronically submitted via EFS-Web are hereby incorporated by reference in its entirety.

The present invention relates to the use of the biomarker Flattop (Fltp) for distinguishing mature β cells from immature progenitor β cells. The present invention further relates to a method for distinguishing a mature β cell from an immature progenitor β cell, the method comprising: determining the presence or absence of the biomarker Flattop (Fltp) in a β cell; wherein the presence of Fltp in the cell indicates that the cell is a mature β cell and wherein the absence of Fltp in the cell indicates that the cell is an immature progenitor β cell. Furthermore, the present invention relates to a method of identifying a compound suitable for differentiating immature progenitor β cells into mature β cells as well as to a method of identifying a compound suitable for preventing the de-differentiating of mature β cells. The present invention additionally relates to a method of differentiating immature progenitor β cells into mature β cells as well as to a method of preventing de-differentiating of mature β cells. In addition, the present invention also relates to a kit for distinguishing mature β cells from immature progenitor β cells and to a pharmaceutical composition for use in treating or preventing diabetes.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The islet of Langerhans is a complex micro-organ that contains five endocrine cell types (α, β, δ, PP, and ε cells), arterial and venous blood supply as well as sympathetic, parasympathetic and sensory neuron innervation (In't Veid and Marichal 2010). The sole function of this micro-organ is to regulate energy metabolism. To fulfill this function, glucose-sensitive β cells are organized around vessels in rosette-like structures to secrete at the apical PM insulin into the blood stream upon food intake (Bonner-Weir 1988). β cells are functionally coupled by gap junctions and establish cell-matrix adhesion to blood vessels, which is required for optimal 1 cell function, suggesting that cell polarity might also be important (Eberhard and Lammert 2009). Some support for this idea comes from the β cell-specific knock out of the Lkb1 kinase that is involved in polarity establishment and mTOR regulation (Granot, Swisa et al. 2009). This leads to a dramatic increase in insulin secretion as well as cell polarity and cilia positioning defects. However, due to the dual role of Lkb1 in polarity establishment and energy control it is difficult to conclude on the requirement of cell polarity for β cell function.

As mentioned above, β cells are arranged around blood vessels and are often, but not always, in direct contact to blood vessels on the apical and basal side (Bonner-Weir 1988). It is uncertain if this heterogeneity in tissue organization also reflects heterogeneity in β cell function. Salomon and Meda already reported that β cells in vitro are heterogeneous in their insulin secretion capacity depending on cell-cell coupling (Salomon and Meda 1986). One year later these results were confirmed in vivo and it was shown that central versus peripheral, but also splenic versus duodenal β cells showed different insulin secretion capacities upon glucose challenge (Stefan, Meda et al. 1987). Further evidence for the heterogeneity of β cells was provided by the demonstration that β cells differ in their glucose-responsiveness due to the higher expression and activity of glucokinase, rather than differences in Glut2 mRNA or glucose transport (Heimberg, De Vos et al. 1993). In contrast, a pancreatic multipotent progenitor (PMP) population was described in mouse and human that resides in the islet, expresses insulin and low levels of Glut2 and shows extensive proliferative capacity, self-renewal and multipotency (Smukler, Amtfield et al. 2011). Recently, the expression of a fluorescent marker under the mouse insulin promoter allowed to distinguish subpopulations of β cells that differ in their granularity, size and secretion capacity, but the reason for these differences is still under debate (Katsuta, Aguayo-Mazzucato et al. 2012). Thus although β cell heterogeneity was discovered over 25 years ago, the underlying principal of this phenomenon is still controversially discussed.

During early postnatal islet neogenesis in mouse, naïve β cells are still organized in solitary or cord-like structures and acquire the typical spheric 3D islet architecture in the first two weeks after birth. These naïve β cells secrete insulin at low thresholds and do not reach maturation until a couple weeks after birth when they start to express the currently only known maturation marker, Urocortin 3 (Ucn3) (Blum, Hrvatin et al. 2012). Functional maturation of β cells derived from progenitor cells is currently one of the major hurdles for cell-replacement therapy (Pagliuca and Melton 2013). Moreover, it was recently proposed that β cell de-differentiation is one of the mechanisms of β cell failure in type 2 diabetes (Talchai, Xuan et al. 2012). Further support for this idea comes from a recent report that Pdx1 maintains β cell identity and β cell specific knock-out of Pdx1 causes an β- to α-cell reprogramming (Gao, McKenna et al. 2014).

Thus, despite the fact that a lot of effort has been invested into investigating β cell maturation, there is still a need to identify novel maturation markers in order to allow understanding the pathomechanisms underlying diabetes, enable regeneration of de-differentiated β cells in islets of Langerhans, and generate functional mature β cells from pluripotent stem cells for cell replacement therapy.

This need is addressed by the provision of the embodiments characterized in the claims.

Accordingly, the present invention relates in a first aspect to the use of the biomarker Flattop (Fltp) for distinguishing mature β cells from immature progenitor β cells.

The term "biomarker" according to the present invention relates to the recited marker in any of its naturally occurring forms, including nucleic acid molecules such as e.g. DNA, including cDNA or genomic DNA, and RNA as well as proteins.

As used herein, the term "Flattop (Fltp)" refers to a recently identified gene expressed in the embryonic node, but also active in other monociliated tissues such as the sensory organs of the inner ear (IE), duct and islets of the pancreas as well as in testis (Lange, Gegg et al. 2012). Additionally, Fltp mRNA is expressed in multiciliated epithelial cells of the lung and of the choroid plexi in the brain. Loss-of-gene function in multiciliated lung epithelial cells has been shown to lead to basal body docking defects, which result in loss of cilia. In addition, loss of Fltp causes planar cell polarity (PCP) phenotypes in the IE and the lung. Further, Fltp localizes in a PCP-like asymmetric fashion in sensory IE cells and genetically interacts with the core PCP molecule Celsr1.

Human Flattop (Fltp) is, for example, represented by the Entrez Gene ID 257177 and UniProt ID UPF0740 protein C1Orf192, as shown in SEQ ID NOs: 1 and 2. Mouse Flattop is, for example, represented by the Entrez Gene ID 75472 and UniProt ID Q6P8X9, as shown in SEQ ID NOs: 3 and 4.

β cells are unique cells present in the pancreas, in particular in the endocrine structures thereof, i.e. the islets of Langerhans. β cells are one of at least five different types of islet cells that produce and secrete hormones directly into the bloodstream and they produce, store and release the hormone insulin. Usually, β cells are perfect sensors of blood glucose levels and secrete just the right amount of insulin into the bloodstream to systemically regulate glucose and energy homeostasis (Lickert 2013). Diabetes, a disease that affects a large number of people worldwide, is associated with β cell failure. Type 1 diabetes results from autoimmune destruction of β cells, whereas in type 2 diabetes a failure of β cells to compensate for peripheral insulin resistance leads to exhaustion, dedifferentiation, and loss of function β cell mass. Preferably, the cells referred to herein are from a mammalian animal, such as e.g. a rodent, preferably a mouse, a rat or a rabbit; a pig, a dog, a cat or a primate. More preferably, the cells are human or mouse cells.

The term "mature β cells", as used herein, refers to highly polarized β cells that secrete insulin in response to a glucose stimulus. This requires molecular machineries that measure blood glucose and produce, process and secrete insulin. Mature β cells show almost no proliferation and are clustered around blood vessels, towards which they secrete the insulin (Eberhard and Lammert 2009). Mature β cells are further characterized by the presence of the maturation marker Ucn3 (Blum, Hrvatin et al. 2012). In addition, as shown in Example 6 below, mature β cells were found herein to show a significant enrichment of genes that are important for mature β cell function, such as genes involved in metabolic processes, glucose metabolism, mitochondria and insulin secretion. Anatomically, mature β cells cluster around blood vessels in rosette-like structures and show apical-basal polarity with insulin granules docking towards the apical lumen (Bonner-Weir 1988).

In accordance with the present invention, the terms "immature progenitor β cells" and "naïve progenitor β cells", which are used interchangeably herein, refer to highly proliferative and low polarized progenitor cells that produce and secrete only low amounts of insulin and express low levels of the glucose transporter Glut2 (Smukler, Artfield et al. 2011). Immature β cells are likely in loose contact with each other and might not form clusters around blood vessels, contrary to mature β cells. Known markers for all β cells, including immature progenitor β cells, but also mature β cells are Pdx1, Nkx6.1 and insulin. However, in contrast to mature β cells, immature progenitor cells lack expression of Flattop and express genes like Glp1r, Gck, Insrr, Slc2a2 to an at least 2-fold lower extent as compared to mature β cells, but show an at least 2-fold higher expression in Smarca1 and Sstr2.

In addition, as shown in Example 6 below, immature progenitor β cells were found herein to show a significant enrichment of further genes that associate with cell proliferation, actin binding, Wnt/PCP, TGF receptor-, G-protein coupled receptor- and ERK-signaling transduction. Anatomically, and in contrast to mature β cells, immature progenitor β cells do not form rosette-like structures but appear to be lying next to the rosettes. Moreover, it appears that immature progenitor β cells do not show the apical-basal polarity with insulin granules docking towards the apical lumen, found in mature β cells (Bonner-Weir 1988).

As is shown in the appended examples, immature β cells lack expression of Fltp while mature β cells express this biomarker. Accordingly, the presence of Fltp can be used to distinguishing mature β cells from immature progenitor β cells. To this end, the presence or absence of Fltp in β cells of interest can be determined, wherein the presence of Ftp indicates that the β cell is a mature β cell and wherein the absence of Ftp indicates that the β cell is an immature progenitor β cell.

As used herein, the term "determining the [ . . . ] presence or absence" refers to the analysis whether the recited molecule is present or absent in cells comprised in the sample investigated. The molecule is considered present in accordance with the present invention when it is detected in amounts exceeding the standard procedural error, such as for example observed in the form of background staining obtained in immunohistochemical or western blot analyses. Such procedural errors can be determined according to established procedures, for example by analyzing non-disease control samples or by omitting certain steps or compounds in the procedure, such as for example a primary antibody in immunohistochemical stainings or a template in nucleic acid amplification techniques etc. In the case that the amount of molecule detected corresponds to or is less than the standard procedural error, e.g. the background staining in an immunohistochemical analysis, the molecule is considered as being absent in the sample.

The use of Fltp fusion proteins comprising a detectable moiety or the use of Fltp reporter proteins for determining the presence or absence of Fltp is also encompassed by the present invention.

In the first case, expression of Fltp leads to the concomitant expression of the detectable moiety, for example a tag such as a His-tag, FLAG-tag, TAP-tag or myc-tag; a luminescent or fluorescent marker such as e.g. luciferase, in particular bacterial luciferase (luxAB), *Photinus* luciferase, *Renilla* luciferase; fluorescent proteins such as e.g. green fluorescent protein (GFP) including enhanced GFP (EGFP), yellow fluorescent protein (YFP), including in particular the improved Venus fluorescent protein, red fluorescent protein (RFP), cyan fluorescent protein (CFP), coral-derived photoproteins including DSRed, HcRed, AmCyan, ZsGreen, ZsYellow, AsRed; or an enzymatic marker, such as e.g. β-galactosidase, CAT, ß-glucuronidase, ß-xylosidase, XylE (catechol dioxygenase), TreA (trehalase), alkaline phosphatase or secreted alkaline phosphatase.

As is shown in the appended examples, a Flattop-Venus fusion protein was generated by directly fusing the Venus fluorescent protein to the open-reading frame of Flattop. Mice expressing this Flattop-Venus fusion protein in all tissues were generated, wherein the Flattop-Venus fusion protein is expressed in equal amounts to the wild-type Flattop protein. This Flattop-Venus fusion reporter has the advantage that it is expressed in physiological amounts, shows normal protein turnover and normal subcellular localization.

In the latter case, the expression of a detectable reporter protein is under the control of the Fltp promoter and, preferably, the naturally occurring regulatory sequences of Fltp expression. Such a reporter protein can be expressed either instead of Fltp expression, or in addition to Ftp expression, and can be detected by the methods described below. The detectable reporter protein may e.g. be any of the luminescent, fluorescent or enzymatic markers recited above. As also described in the examples below, a $Flt^{ZV}$ knock-in/knock-out allele was generated where the entire ORF was replaced by a multicistronic lacZ-Venus reporter cassette that contained, amongst others, a bright Histone 2B (H2B)-Venus fluorescent reporter gene and allows to explore Fltp expression and function in vivo.

In accordance with the present invention, the presence or absence of a specific molecule, such as e.g. Fltp, a reporter protein, or a Fltp fusion protein, can be determined either on (i) the protein level, (ii) the nucleic acid level, or (iii) a combination thereof.

Methods for the determination of the presence or absence of a protein include but are not limited to methods such as e.g. immunohistochemical methods, immunocytochemical methods, live cell imaging including, without being limiting high-content screening via live reporters (such as e.g. Opereta, Operon), bulk fluorescent measurements (e.g. Envision), quantitative fluorescence imaging/quantitative fluorescence microscopy, ELISA, FACS analysis or Cytof® Mass Cytometry as well as immunoblotting, such as e.g. Western blotting, or polyacrylamide gel electrophoresis in conjunction with protein staining techniques such as Coomassie Brilliant blue or silver-staining. Preferably, screening for Flattop protein is carried out by immunohistochemistry or immunocytochemistry using antibodies or alternative binding molecules specific for the Flattop protein or by live cell imaging using e.g. a reporter system.

The term "antibody", as used in accordance with the present invention, comprises polyclonal and monoclonal antibodies, as well as derivatives or fragments thereof, which still retain their binding specificity. Antibody fragments or derivatives comprise, inter alia, Fab or Fab' fragments as well as Fd, $F(ab')_2$, Fv or scFv fragments; see, for example Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also includes embodiments such as chimeric (human constant domain, non-human variable domain), single chain and humanized (human antibody with the exception of non-human CDRs) antibodies.

Various techniques for the production of antibodies are well known in the art and described, e.g. in Harlow and Lane (1988) and (1999). For example, the antibodies can be produced as peptidomimetics. Further, techniques described for the production of single chain antibodies (see, inter alia, U.S. Pat. No. 4,946,778) can be adapted to produce single chain antibodies specific for their respective target. Also, transgenic animals or plants (see, e.g., U.S. Pat. No. 6,080,560) may be used to express (humanized) antibodies specific for the target of this invention. Most preferably, the antibody is a monoclonal antibody, such as a human or humanized antibody. For the preparation of monoclonal antibodies, any technique which provides antibodies produced by continuous cell line cultures can be used. Examples for such techniques are described, e.g. in Harlow and Lane (1988) and (1999) and include the hybridoma technique originally developed by Köhler and Milstein (Kohler and Milstein 1975), the trioma technique, the human B-cell hybridoma technique (Kozbor 1983) and the EBV-hybridoma technique to produce human monoclonal antibodies (Cole 1985). Surface plasmon resonance as employed in the BIAcore system can be used to increase the efficiency of phage antibodies which bind to a target protein (Schier and Marks 1996). It is also envisaged in the context of this invention that the term "antibody" comprises antibody constructs which may be expressed in cells, e.g. antibody constructs which may be transfected and/or transduced via, inter alia, viruses or plasmid vectors.

As is shown in the appended examples, two different polyclonal rabbit antibodies were raised against a central and C-terminal epitope. These antibodies can be used as primary antibodies to detect the protein in tissues or cell cultures and using secondary antibodies either conjugated to horseradish peroxidase, alkaline phosphatase or fluorescent dyes. Based on these epitopes shown in examples below, it is possible without further ado to prepare antibodies, for example employing any of the methods known in the art referred to above.

Alternative binding molecules include, without being limiting, proteins or peptides in which specific binding properties have been introduced, for example by mutagenesis, into a protein scaffold with suitable biophysical properties. Ideally, small globular proteins that are easy to express and purify, which are soluble and stable, which do not aggregate and which are non-immunogenic, are used as a scaffold. So far more than 50 proteins of this class have been described, among them affibodies (which are based on the Z-domain of staphylococcal protein A (Feldwisch and Tolmachev 2012)), adnectins (based on the tenth domain of human fibronectin (Gebauer and Skerra 2009)), anticalins (derived from lipocalins (Beste, Schmidt et al. 1999, Gebauer and Skerra 2009)), DARPins (derived from ankyrin repeat proteins (Gebauer and Skerra 2009)), avimers (based e.g. on multimerised Low Density Lipoprotein Receptor (LDLR)-A (Weidle, Auer et al. 2013)), nanofitins (derived from the DNA binding protein Sac7d of *Sulfolobus acidocaldarius* (Mouratou, Behar et al. 2012)), affilins (structurally derived from gamma-B crystalline or Ubiquitin (Weidle, Auer et al. 2013)), Kunitz domain peptides (derived from the Kunitz domains of various protease inhibitors (Weidle, Auer et al. 2013)) and Fynomers®, which are derived from the human Fyn SH3 domain (Bertschinger, Grabulovski et al. 2007, Grabulovski, Kaspar et al. 2007, Gebauer and Skerra 2009, Schlatter, Brack et al. 2012). These proteins or peptides are well known in the art.

As mentioned herein above, and depending on the detection method employed, the determination of Fltp expression can be employed by live imaging, i.e. methods where cells are or tissue is kept alive during observation, or on fixed samples, i.e. where cells or tissues are immobilized and do not survive the imaging process.

The relative amount of the protein of interest is often determined by comparing the total measured amount of protein, e.g. in form of the fluorescence intensity of a labeled protein, derived from a sample of interest with the total measured amount of protein obtained from a control sample. Also of use in protein quantification is the Agilent Bioanalyzer technique.

Determination on the nucleic acid level refers to the determination of the presence or absence of a nucleic acid molecule encoding the protein of interest and that is only present (i.e. up-regulated) when expression of said protein has been activated. Preferably, said nucleic acid molecule is mRNA or a cDNA obtained from mRNA. It will be appreciated that genomic DNA is excluded in accordance with the present invention.

Methods for determining presence or absence of a molecule on the nucleic acid level include, but are not limited to hybridization assays, nucleic acid amplification assays or sequencing assays.

Examples for hybridization assays comprise, without limitation, in situ RNA hybridization, Northern and Southern blot assays. These methods are well known in the art and have been described, e.g. in Michael Green and Joseph Sambrook Molecular Cloning: A Laboratory Manual (Fourth Edition).

Non-limiting examples for nucleic acid amplification assays and means to perform such include PCR, (including nested PCR, RT-PCR, quantitative (real-time) detection, PCR extension assays, nucleic acid sequence base amplification (NASBA), single-strand confirmation polymorphism (SSCP) PCR, PCR-restriction enzyme fragment length polymorphism (RFLP) analysis), amplification refractory mutation systems (ARMSTM) and amplification refractory mutation system linear extension (ALEXTM) assays. Details of such methods can be found in art, (Newton, Graham et al. 1989, Haque, Hehir et al. 1998, Pissard, Huynh et al. 2002, Kakavas, Noulas et al. 2006, Steemers, Chang et al. 2006). Quantitative PCR can for example be used to measure Fltp levels in islet cells. To this end, cDNA can first be linear amplified and the amplified cDNA can then be subjected to quantitative PCR.

Examples for sequencing assays comprise without limitation approaches of sequence analysis by direct sequencing, fluorescent SSCP in an automated DNA sequencer and Pyrosequencing. These procedures are common in the art, see e.g. Adams "Automated DNA Sequencing and Analysis" and Alphey, "DNA Sequencing: From Experimental Methods to Bioinformatics" (Ramon, Braden et al. 2003, Meng, Hager et al. 2005). For example, RNA sequencing can be used to analyze mRNA levels in Flattop positive and negative FACS-isolated islet cell populations.

It is particularly preferred in accordance with the embodiments of the present invention that the presence or absence of Fltp is determined by immunohistochemistry, RNA in situ hybridisation, quantitative PCR or a combination thereof. Preferred antibodies for use in determining the presence or absence (or the amount) of Fltp are the antibodies described in the Examples below, as well as any antibodies directed to the epitope shown in FIG. 11, i.e. epitopel: DNPDEPQSSHPSAGHT (mouse; SEQ ID NO:5); NSPDELQSSHPSAGHT (human; SEQ ID NO:6) and mP17Rik-116-135: KPFDPDSQTKQKKSVTKTVQ (mouse; SEQ ID NO:7); and the corresponding human epitope: KPHDPDSQKKLRKKSITKTVQ (human; SEQ ID NO:8). Preferred primers for use in determining the presence or absence (or the amount) of Fltp are the primers described in the Examples below, in particular the following primers: human forward primer 5'-ACCTGGCAAATGCCTCTGAA-3' (SEQ ID NO:9); human reverse primer 5'-GGATCATGGGGCTTGCCTAA-3' (SEQ ID NO:10) and human forward primer 5'-CCTGACCTCCCGTACAACTG-3' (SEQ ID NO:11); human reverse primer 5'-TGGATCATGGGGCTTGCCTA-3' (SEQ ID NO:12); mouse: 5'-AGCCATACCACAT-TTGTAGAGG-3' (SEQ ID NO:13); 5'-CAGCATGGCATA-GATCTGGAC-3 (SEQ ID NO:14)'; 5'-GAGGCTGACTGGGAACAATC-3' (SEQ ID NO:15).

Preferred probes for use in determining the presence or absence (or the amount) of Fltp is for example the probe shown in SEQ ID NO: 16, which can be prepared using e.g. the primers shown in SEQ ID NOs: 17 and 18.

In accordance with the present invention, it was shown that during post-natal islet neogenesis β cells gradually receive increased Wnt/PCP signaling measured by a Fltp reporter gene, which correlates with 3D islet formation and β cell maturation. Flattop activity rises in α-, PP-, δ-, and ε-cells up to 45% and in β cells up to 70% in the first two weeks of development. In adult islets, the Fltp-negative β cells show a roughly 2-fold higher proliferation rate when compared to the Fltp-positive β cells, which strongly increases to a four-fold increase upon pregnancy. Fltp loss-of-function was found to lead to $1^{st}$ phase insulin secretion defects and shows that PCP-mediated cytoskeletal rearrangements, basal body positioning and likely primary cilia function is required for mature beta cell function. This is further supported by the identification of SNPs in the human FLTP gene, which associate with insulin secretion defects.

The isolation of Fltp reporter negative and Fltp reporter expressing β cells from knock-in reporter animals allowed for the first time to analyze the differential molecular properties of these naïve and mature β cell populations. Strikingly, the expression of maturation and polarity markers, glycolysis enzyme and signaling receptors is markedly different between these β cell populations. This opens new possibilities for a pharmacological targeting of the proliferative vs. mature functions of β cells.

In addition, it was shown by genetic lineage tracing that the highly proliferative Fltp-negative progenitor cells can convert into Fltp-positive, mature β cells. Together, these findings identify Fltp as a novel marker and PCP as the maturation principal of β cells, which solves a long-standing mystery of β cell heterogeneity and opens new avenues for β cell regeneration.

Moreover, these results hints towards the existence of a pancreatic multipotent progenitor (PMP) population that has high self-renewing capacity, can differentiate in all endocrine lineages and resides in mouse and human adult islets of Langerhans (Smukler, Amrntfield et al. 2011). The identification of heterogeneous β cell populations that have either increased proliferative capacity or a more mature phenotype opens new possibilities of triggering these specific β cell features in the future. For example, the identification of differentially expressed signaling receptors and pathways can form a pharmacological entry point for regenerative therapies.

Additionally, the identification of Ftp as a β cell maturation marker will also improve the generation of functional mature β cells from pluripotent stem cells. At present, only naïve, immature and poly-hormonal insulin-producing cells can be produced in vitro. The identification of the PCP effector gene Fltp indicates that 3D environment is important for functional β cell maturation. Moreover, the Fltp PCP reporter gene allows screening for signals, miRNAs and small molecules that activate PCP signaling and lead to functional β cell maturation. In addition, in light of recent findings that β cell de-differentiation contributes to β cell failure in type 2 diabetes, the identification of Fltp as a novel maturation marker allows a more detailed study of the pathogenesis of type 2 diabetes in mouse and man.

Overall, the findings of the present invention resolve the long-standing mystery of β cell heterogeneity and strongly suggest that tissue polarity influences the heterogeneous polarity status of endocrine cells. In terms of β cells, this difference in polarity status directly associates with different biological function. The discovery of this principle and Ftp as a PCP reporter allows deciphering pathomechanisms of diabetes and enables for novel approaches for regenerative therapy.

The present invention further relates to a method for distinguishing a mature β cell from an immature progenitor β cell, the method comprising: determining the presence or absence of the biomarker Flattop (Fltp) in a β cell; wherein the presence of the Ftp in the cell indicates that the cell is a mature β cell and wherein the absence of Ftp in the cell indicates that the cell is an immature progenitor β cell.

In accordance with the present invention, the method for distinguishing a mature β cell from an immature progenitor β cell is not limited to a single cell. Instead, also a plurality of mature β cells can be distinguished from a plurality of immature progenitor β cells.

The term "comprising", as used herein, denotes that further steps and/or components can be included in addition to the specifically recited steps and/or components. However, this term also encompasses that the claimed subject-matter consists of exactly the recited steps and/or components.

The definition of the term "determining the [ . . . ] presence or absence" recited above as well as the above described preferred methods of achieving such a determination apply mutatis mutandis also to this method of the invention.

In a preferred embodiment of this method of the invention, the presence or absence of Fltp is determined by immunohistochemistry, quantitative PCR, FACS sorting or a combination thereof. Preferred antibodies, primers and probes have been described in detail above.

The present invention further relates to a method of identifying a compound suitable for differentiating immature progenitor β cells into mature β cells, the method comprising: (a) contacting a cell population comprising immature progenitor β cells with a test compound; and (b) subsequently determining the presence or expression level of the biomarker Flattop (Fltp) in the β cells comprised in the cell population; wherein the presence of Fltp, or an increased expression level of Fltp, in the β cells comprised in the cell population after the contacting with the test compound is indicative of a compound suitable for differentiating immature progenitor β cells into mature pi cells.

This embodiment relates to a screening assay for the identification of compounds capable of differentiating β cells, wherein Ftp is used as a biomarker to detect said differentiation. All definitions and preferred embodiments provided herein with regard to the use of the biomarker Flattop (Fltp) and the method for distinguishing mature from immature β cells apply mutatis mutandis also to this screening method of the invention.

As used herein, the term "differentiating β cells" refers to converting immature, naïve progenitor β cells to mature β cells.

Essentially any compound can be assayed in accordance with the methods of the present invention. Such compounds include organic or inorganic molecules. Organic molecules relate or belong to the class of chemical compounds having a carbon basis, the carbon atoms linked together by carbon-carbon bonds, including biological entities such as e.g. proteins, sugars, nucleic acids, lipids. The original definition of the term organic related to the source of chemical compounds, with organic compounds being those carbon-containing compounds obtained from plant or animal or microbial sources. Organic compounds can be natural or synthetic. Small organic molecules preferably have a molecular weight of about 500 Da or below. Inorganic compounds are derived from mineral sources and include all compounds without carbon atoms (except carbon dioxide, carbon monoxide and carbonates). There are many suppliers of such compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. In addition, compounds to be analysed may be synthesized by methods known in the art. Test compounds may be comprised in compound libraries of diverse or structurally similar compounds (e.g., combinatorial chemistry synthesized libraries) and a plurality of test compounds in a library can be assayed simultaneously. Optionally, test compounds derived from different libraries can be pooled for simultaneous evaluation. A library can comprise a random collection of molecules. Alternatively, a library can comprise a collection of molecules having a bias for a particular sequence, structure, or conformation. Methods for preparing libraries containing diverse populations of various types of molecules are known in the art (Brenk, Schipani et al. 2008, Quinn, Carroll at al. 2008). Numerous libraries are also commercially available.

Preferred compounds for screening for their potential in differentiating β cells include, without being limiting, small molecules, antisense nucleic acid molecules, siRNA, shRNA, miRNA, antibodies, aptamers or ribozymes as well as hormones and cytokines. Such compounds may be particularly suitable as inhibitors of pathways that are involved in the maintenance of an undifferentiated state of β cells, e.g. by blocking specific binding sites of a relevant target molecule(s) within said pathway. Alternatively, or additionally, such compounds may also act as activators of pathways that drive the differentiation of β cells, such as e.g. the Wnt/PCP pathway, as described in more detail below.

A "small molecule" according to the present invention may be, for example, an organic or inorganic molecule, as defined herein above. Preferably, the small molecule has a molecular weight of less than about 2000 amu, or less than about 1000 amu, such as less than about 500 amu, and even more preferably less than about 250 amu. The size of a small molecule can be determined by methods well-known in the art, e.g., mass spectrometry. The small molecules may be designed, for example, based on the crystal structure of the target molecule, where sites presumably responsible for the biological activity, can be identified and verified in in vivo assays such as in vivo high-throughput screening (HTS) assays.

The term "antisense nucleic acid molecule", as used herein, is known in the art and refers to a nucleic acid which is complementary to a target nucleic acid, i.e. a nucleic acid encoding the target protein. An antisense molecule in accordance with the invention is capable of interacting with the target nucleic acid; more specifically it is capable of hybridizing with the target nucleic acid. Due to the formation of the hybrid, transcription of the target gene(s) and/or translation of the target mRNA is reduced or blocked. Standard methods relating to antisense technology have been described (Melani, Rivoltini et al. 1991).

As used herein, the term "siRNA", refers to "small interfering RNA", also known as "short interfering RNA" or "silencing RNA", and relates to a class of 18 to 30, preferably 19 to 25, most preferred 21 to 23 or even more preferably 21 nucleotide-long double-stranded RNA molecules that play a variety of roles in biology, siRNAs naturally found in nature have a well defined structure: a short double-strand of RNA (dsRNA) with 2-nt 3' overhangs on either end. Each strand has a 5' phosphate group and a 3' hydroxyl (—OH) group. The double-stranded RNA molecule or a metabolic processing product thereof is capable of mediating target-specific nucleic acid modifications, particularly RNA interference, where the siRNA interferes with the expression of a specific gene, and/or DNA methylation.

siRNAs can be exogenously (artificially) introduced into cells to bring about the specific knockdown of essentially any gene of interest of which the sequence is known. Exogenously introduced siRNAs may be devoid of overhangs at their 3' and 5' ends, however, it is preferred that at least one RNA strand has a 5'- and/or 3'-overhang. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3' overhangs on either end. 2'-deoxynucleotides in the 3' overhangs are as efficient as ribonucleotides, but are often cheaper to synthesize and probably more nuclease resistant.

The term "shRNA", as used herein, refers to "short hairpin RNA" and relates to a sequence of RNA that makes a tight hairpin turn that typically can be used to silence gene expression via RNA interference, shRNA can for example use a vector introduced into cells, in which case preferably the U6 promoter is utilized to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

Preferably, si/shRNAs to be used in the present invention are chemically synthesized using conventional methods that, for example, appropriately protected ribonucleoside phosphoramidites and a conventional DNA/RNA synthesizer. Non-limiting examples of suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs or shRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

The term "miRNA", as used herein, refers to "microRNAs" and relates to single-stranded RNA molecules which, as endogenous RNA molecules, regulate gene expression. Binding to a complementary mRNA transcript triggers the degradation of said mRNA transcript through a process similar to RNA interference. Accordingly, miRNA may be employed as an inhibitor of signaling pathways in accordance with the present invention.

The term "antibody", as used in accordance with the present invention, has been defined herein above.

An "aptamer" is a DNA or RNA molecule that binds other molecules, such as nucleic acids, proteins, small organic compounds, and even entire organisms. A database of aptamers is maintained in the world wide web at aptamer.icmb.utexas.edu/.

More specifically, aptamers can be classified as nucleic acid aptamers (i.e. DNA or RNA aptamers) or peptide aptamers. Nucleic acid aptamers consist of (usually short) strands of oligonucleotides and have been engineered through repeated rounds of in-vitro selection or equivalently, SELEX (systematic evolution of ligands by exponential enrichment) to bind to various molecular targets such as small molecules, proteins, nucleic acids, and even cells, tissues and organisms. Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop is typically comprised of 10 to 20 amino acids, and the scaffold may be any protein which has good solubility properties. Currently, the bacterial protein Thioredoxin-A is the most used scaffold protein, the variable loop being inserted within the reducing active site, which is a -Cys-Gly-Pro-Cys-loop in the wild-type protein, the two cysteine lateral chains being able to form a disulfide bridge. Peptide aptamer selection can be made using different systems, but the most used is currently the yeast two-hybrid system.

In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the inherently low molecular weight of aptamers. Several modifications, such as 2'-fluorine-substituted pyrimidines, polyethylene glycol (PEG) linkage, fusion to albumin or other half-life extending proteins etc. are available to scientists with which the half-life of aptamers easily can be increased to the day or even week time scale.

A ribozyme (from ribonucleic acid enzyme, also called RNA enzyme or catalytic RNA) is an RNA molecule that catalyzes a chemical reaction. Many natural ribozymes catalyze either their own cleavage or the cleavage of other RNAs, but they have also been found to catalyze the aminotransferase activity of the ribosome. Non-limiting examples of well-characterized small self-cleaving RNAs are the hammerhead, hairpin, hepatitis delta virus, and in vitro-selected lead-dependent ribozymes, whereas the group I intron is an example for larger ribozymes. The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site. The basic principle of constructing hammerhead ribozymes is as follows: An interesting region of the RNA, which contains the GUC (or CUC) triplet, is selected. Two oligonucleotide strands, each usually with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences.

A recent development, also useful in accordance with the present invention, is the combination of an aptamer recognizing a small compound with a hammerhead ribozyme. The conformational change induced in the aptamer upon binding the target molecule is supposed to regulate the catalytic function of the ribozyme.

Hormones and cytokines are well known in the art. They are polypeptides that function as chemical messengers released by a cell or a gland in one part of the body sending out messages that affect cells in other parts of the organism, thus transporting a signal from one cell to another. Non-limiting examples for hormones and cytokines that might be suitable as test compounds include betatrophin, myokines (i.e. from muscles), hepatokines, adipokines, incretins or other known cytokines (Lickert 2013).

Preferably, the screening methods of the present invention are carried out in high-throughput format. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably carried out by one or more computer-controlled robotic systems including pipetting devices. In case large libraries of test compounds are to be screened and/or screening is to be effected within a short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to said activity.

Also encompassed herein are modified versions of these compounds. In other words, the compounds identified by the screening methods of the present invention may result in the identification of a lead compound, which is subsequently optimized to arrive at a compound that may, for example, be used in a pharmaceutical composition. Methods for the optimization of the pharmacological properties of compounds identified in screens, the lead compounds, are known in the art and comprise a method of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiffs bases, oximes, acetales, ketales, enolesters, oxazolidines, thiazolidines or combinations thereof.

The various steps recited above are generally known in the art. They include or rely on quantitative structure-activity relationship (QSAR) analyses (Kubinyi (1992) "Hausch-Analysis and Related Approaches"), combinatorial biochemistry, classical chemistry and others (Holzgrabe and Bechtold 2000).

In a first step, a cell population comprising immature progenitor β cells is contacted with a test compound as defined above. The cell population comprising immature progenitor β cells may be obtained from embryonic or pluripotent stem or progenitor cells or may be a primary cell population obtained from pancreas, such as e.g. pancreatic explant cultures, or parts thereof such as e.g. the islets of Langerhans, or may be an established immature β cell line, such as e.g. MIN6 (mouse) and INS-1E (rat) insulinoma cell lines, which are commonly used in the diabetes research field, as well as e.g. the immortalized human β cell lines (Ravassard, Hazhouz et al. 2011). Moreover, the cell population may also be a tissue preparation, such as for example (an) isolated, intact islet(s) of Langerhans. Islets of Langerhans are mini-organs that, e.g. in mouse, are present in a capsule. They can be isolated from the pancreas after mildly digesting the pancreas with collagenase to loosen the extracellular matrix and then performing a density gradient centrifugation to isolate the islets, which are visible under a dissecting microscope and can be hand-picked. The cells tissue preparations can be from any animal of interest. Preferably, the cells or tissue preparations are from a mammalian animal, such as e.g. a rodent, preferably a mouse, a rat or a rabbit; a pig, a dog, a cat or a primate. In particular islets isolated from pig are a promising tool, as higher amounts of islets can be isolated from pigs as compared to mice.

Further, the screening assay of the present invention may also be carried out in vive in a suitable non-human animal model. Preferably, said non-human animal model is a mammalian animal, such as e.g. a rodent, preferably a mouse, a rat or a rabbit; a pig, a dog, a cat or a non-human primate. However, it is particularly preferred that this screening method of the present invention is an in vitro method.

The cell population may comprise any amount of immature progenitor β cells, as long as immature progenitor β cells are present in detectable amounts. Preferably, the cell population comprises at least 5% immature progenitor β cells, such as at least 10% immature progenitor β cells, more preferably at least 20% immature progenitor β cells, even more preferably at least 30%, such as at least 40%, at least 50%, at least 60%, at least 70% or even more preferably at least 80% immature progenitor β cells. It is even more preferred that the cell population comprises at least 90% immature progenitor β cells, more preferably at least 95% immature progenitor β cells and even more preferably at least 98% immature progenitor β cells. Most preferably, the cell population comprises 100% immature progenitor β cells, i.e. all of the β cells in the cell population are immature progenitor β cells and no mature β cells are present in detectable amounts.

In those cases where the cell population does not comprise 100% immature β cells, it is preferred that the remaining cells are selected from mature β cells that have already differentiated, as well as other cells naturally present in tissues comprising β cells, such as e.g. the pancreas. Such other cells include e.g. ductal cells, acinar cells, or other endocrine cells of the islet of Langerhans, such as e.g. α-, PP-, δ-, and ε-cells, and fibroblasts. Typically, however, when using primary islet cell preparations, non-endocrine contaminating cells disappear during culture and represent less than 1% of the total cells of the cell population. More preferably, the cell population does not comprise any α-, PP-, δ-, and ε-cells. Most preferably, the cell population consists of immature progenitor β cells, i.e. all of the cells in the cell population are immature progenitor β cells and no other cells are present. Means and methods of enriching a cell population to the desired degree of purity are well known in the art and include, without being limiting, manual picking of cells or automated picking by use of a robot, laser-capture microdissection or FACS (fluorescence activated cell sorting). Such methods are described for example in (Murray 2007, Tung, Heydari at al. 2007).

The term "at least" as used herein, such as e.g. the term "at least 5%" or "at least one" refers to the specifically recited amount or number but also to more than the specifically recited amount or number. For example, the term "at least 5% immature progenitor β cells" encompasses also at least 6%, at least 7%, at least 8%, at least 9% immature progenitor β cells and so on. Furthermore, this term also encompasses exactly 5%, exactly 6%, exactly 7%, exactly 8%, exactly 9% immature progenitor β cells and so on.

The presence of immature progenitor β cells in the cell population can be determined without further ado, for example based on the characteristics of immature progenitor β cells provided herein above. For example, the presence of the markers Pdx1 and Nkx6.1 can be used to determine the presence of immature progenitor β cells in the cell population together with a determination of the absence of the novel biomarker Fltp and/or the absence of the established marker Ucn3. Suitable staining methods for showing the presence or absence of such markers, either in individual cells or in the entire cell population, are well known in the art. Furthermore, as shown in Example 6 below, immature progenitor β cells were found herein to show a significant enrichment of genes that associate with cell proliferation, actin binding, Wnt/PCP-, TGF receptor-, G-protein coupled receptor- and ERK-signaling transduction. These genes may therefore serve as an indicator for the presence of immature progenitor β cells, e.g. via immunohistological staining of the cells for the expression products of these genes, or via in situ hybridisation techniques etc.

Preferably, the cell population comprising immature progenitor β cells used for the screening (also referred to herein as the "starting cell population") is a population comprising, preferably consisting of, Nkx6.1-positive/Fltp-negative cells.

After contacting this cell population with the test compound, the presence or expression level of the biomarker Fltp is determined in the β cells comprised in the cell population in a subsequent step of the method of the invention.

With regard to an individual β cell, the presence of Ftp indicates that the β cell is a mature β cell, as detailed herein above. Accordingly, where the effect of the test compound on an individual β cell is analysed, the absence of Fltp expression within such a cell prior to contacting with the test compound and the subsequent presence of Fltp expression within such a cell after contacting with the test compound indicates that the test compound is suitable for differentiating immature progenitor β cells into mature β cells. Similarly, if all the cells originally present in the cell population employed in the screening assay were immature β cells (i.e. 100% immature β cells without any mature β cells), this starting population would have lacked Fltp expression completely. In those cases, the presence of Flp after contacting with the test compound indicates that the cell population now comprises mature β cells, as these cells now express the novel biomarker Fltp. Therefore, the presence of Fltp in these cell populations after contacting with the test compound is indicative of a compound suitable for differentiating immature progenitor β cells into mature β cells.

Determining the presence or absence of Fltp can be accomplished in several ways, as described above.

In those cases where the starting call population already contains mature β cells, said starting cell population already expresses Fltp, i.e. Fltp is already present in the cell population. Accordingly, it is required that the expression level of Fltp is determined after contacting with the test compound, instead of simply determining the presence thereof. The expression level of Fltp after contacting with the test compound is then compared with the expression level of Fltp prior to contacting with the test compound and an increase in said expression level after contacting with the test compound is indicative of a compound suitable for differentiating immature progenitor β cells into mature β cells.

The term "expression level", as used herein, refers to a value of expression of a particular molecule in a sample of interest. The expression level corresponds to the number of copies of the expression product of the corresponding gene, either on a nucleic acid level (e.g. mRNA) or on the protein level. Methods for determining the expression level of a molecule include the methods described herein above for determining the presence or absence of a molecule on the nucleic acid level or on the amino acid level, such as e.g. hybridization assays, nucleic acid amplification assays, immunohistochemical methods but also e.g. Western blotting or polyacrylamide gel electrophoresis in conjunction with protein staining techniques such as Coomassie Brilliant blue or silver-staining.

The term "increased expression level", as used herein, refers to a higher expression level of the biomarker of interest, i.e. Fltp, in the cells after treatment with the test compound as compared to the expression level observed in a control sample. Such a control sample can be e.g. the cell population prior to contacting with the test compound or a cell population that is of the same origin, and that is identical in its characteristics to the cell population used in the assay but not treated with the test compound. It will be appreciated that for the control sample to be identical in its characteristics to the cell population used in the assay, said control sample is not further cultured under conditions that could change these characteristics, e.g. by inducing differentiation of the cells.

For example, a starting cell population may be divided and one part is used for determining the expression level of Fltp prior to treatment and the second part is used in this method of the invention. Determining the Fltp expression level in the control sample may be carried out prior to performing the present method of the invention, such that the determined values may be used as a reference at later times whenever a cell population is screened in accordance with the method of the present invention; or may be determined in parallel each time a cell population is screened in accordance with the method of the present invention. Such a reference value may also be determined only once and stored as a standard for all future tests.

Preferably, the term "increased expression level" relates to a statistically significant higher expression level of Fltp after treatment as compared to the expression level observed in the control sample. A statistically significant difference is for example when the amount of Fltp expression differs by at least 2σ, i.e. two-times the standard deviation from the expression level obtained in the control sample, wherein the control sample is derived in repeated determination from multiple samples. More preferably, the expression level of Fltp is considered to be increased if it is at least 10% higher after contacting with the test compound as compared to the expression level observed in the control sample, such as for example at least 20% higher, at least 30% higher, at least 40% higher, at least 50% higher, at least 75% higher, at least 100% higher (i.e. twice as high), at least 200% higher, at least 300% higher, at least 500% higher etc. Preferably, the effect of the test compound on the expression level of Fltp is determined after treatment with said test compound for at least about 5 minutes, such as for at least about 10 minutes, more preferably at least about 30 minutes, such as e.g. at least about 1 hour, even more preferably at least about 2 hours, such as e.g. at least about 3 hours, at least about 4 hours, at least about 5 hours, at least about 6 hours, even more preferably at least about 12 hours and most preferably at least about 24 hours.

The term "about", as used herein, encompasses the explicitly recited amounts as well as deviations therefrom of ±15%. More preferably, a deviation of ±10%, and most preferably of +5% is encompassed by the term "about".

It will be appreciated that similar considerations apply in those cases where the starting cell population contains cells other than β cells but that are suspected to, or known to, express Fltp, such as e.g. α-, PP-, δ-, and ε-cells. Also in those cases, Fltp is already present in the starting cell population. In these cases, it will have to be ensured that the presence or increased expression of Fltp after contacting with the test compound is determined in β cells but not in the other cell types or in the overall population. Means and methods to determine the expression of Fltp specifically in β cells are well known in the art. For example, using immunohistological stainings for Fltp as well as cell-specific additional markers, or by sorting cells using e.g. FACS, it can be determined whether a change of Fltp expression (from absent to present or from present to an increased amount of expression) indeed occurs in the β cells of the cell population. The present invention also relates to a method of identifying a compound suitable for preventing the de-differentiation of mature β cells, the method comprising: (a) culturing a cell population comprising mature β cells in the presence of a test compound, wherein the cells are cultured under conditions that induce the de-differentiation of said mature β cells; and (b) subsequently determining the expression level of the biomarker Flattop (Fltp) in the β cells cultured in step (a), wherein an expression level of Fltp determined in step (b) that is substantially identical to the expression level of Fltp in the cell population comprising mature β cells prior to the culture in step (a) is indicative of a compound suitable for preventing the de-differentiation of mature β cells.

This embodiment relates to a screening assay for the identification of (a) compound(s) capable of preventing the de-differentiating of mature β cells, thereby maintaining mature β cells in culture. The novel biomarker Fltp is used as a biomarker to detect the maturation state of the β cells.

All definitions and preferred embodiments provided herein with regard to the use of the biomarker Fltp, the method for distinguishing mature from immature β cells and the method of identifying a compound suitable for differentiating immature progenitor β cells into mature β cells apply mutatis mutandis also to this screening method of the invention.

In accordance with this method of the invention, a compound is screened for that is capable of preventing the de-differentiation of mature β cells, i.e. a compound that maintains mature β cells in culture as mature cells.

In a first step, a cell population comprising mature β cells is cultured in the presence of a test compound. Cell culture conditions are chosen that would normally, i.e. in the absence of the test compound, induce the de-differentiation of said mature β cells.

General cell culture conditions as well as suitable cell culture media are well known in the art (e.g. Cooper 2000 "Tools of Cell Biology"; Turksen, 2004 "Animal cell culture"). Preferred conditions and media are detailed below.

It is preferred in any of the cell culture conditions described herein that the medium is exchanged (i.e. refreshed) at appropriate intervals that can be determined by the skilled person without further ado, such as e.g. every four days, more preferably every three days, such as e.g. every two days and most preferably the medium is exchanged for fresh cell culture medium every 24 hours.

Suitable cell culture media include, without being limiting, RPMI-1640 (e.g. Biochrom), Dulbecco's MEM (e.g. FG 1445, Biochrom), Basal Iscove Medium (e.g. F0465, Biochrom), MCDB 153 Basal Medium (e.g. F8105, Biochrom AG), William's Medium E (e.g. F 1115, Biochrom) containing additives including, without being limiting, FCS Gold (e.g. A15-151, PAA Laboratories GmbH), L-glutamine (e.g. M11-004, PAA Laboratories GmbH), antibiotic/antimycotic (e.g. A5955, Sigma-Aldrich GmbH), gentamycin (e.g. A2712, Biochrom), insulin (e.g. I9278, Sigma-Aldrich GmbH) and/or additional additives known in the art. Particularly preferred culture media are, for example, RPMI 1640 with 1 to 10% FBS (heat inactivated 30 min 56° C.) and 1× Pen/Strep (corresponding to 100 units/ml of penicillin and 100 µg/ml of streptomycin); or RPMI 1640 or DMEM:F12 (1:1) with 5% FCS (heat inactivated 30 min 56° C.), 2 mM L-Glutamin, 1× Pen/Strep, 1 mM Sodium pyrovate, 0.1 mM-Mercaptoethanol, Ix non-essential amino acids. Most preferably, the cells are cultured in islet culture medium. 500 ml of islet culture medium consists of RPMI 1640, 1 to 10% FCS and 5 ml Pen/Strep (100×).

Preferably, the cells or islets are cultured at 37° C. It is also preferred that the cells are cultured at 37° C. until the cells have formed a confluent monolayer covering the surface of the culture dish. Typically, this takes between 2 to 4 days. The cells are then detached using protease treatment, such as e.g. TrypLE (e.g. Gibco, 12563) and are then re-plated at a diluted density of between 1:2 to 1:5 with islet culture medium (consisting of RPMI 1640, 1 to 10% FCS and 1× Pen/Strep) and cultured again until a confluent monolayer covering the surface of the culture dish has grown, and so on (see above).

The term "conditions that induce the de-differentiation of said mature β cells" refers to all cell culture conditions that result in the loss of the maturation state of the mature β cells in said cell population. Such cell culture conditions include, without being limiting, any of the above recited culture media with reduced amounts of serum as compared to standard media, such as e.g. the islet culture medium described above; without exogenous cytokines and without hormones. Preferably, the medium contains less than 1% serum, such as e.g. less than 0.9% serum, more preferably less than 0.8% serum and even more preferably less than 0.5% serum.

More preferably, such a medium would consist of only islet culture medium consisting of RPMI 1640, less than 1% FCS as well as 1× Pen/Strep and additives selected from amino acids, antibiotics and antimycotics. Alternatively, the de-differentiation can be induced by culturing the cells in the presence of reduced amounts of oxygen, such as e.g. 5% of oxygen. As a further alternative, compounds that activate the hedgehog signaling pathway may be added to the cell culture medium, in order to induce de-differentiation. Such compounds are well known in the art and include, without being limiting, ligands such as e.g. Shh, Ihh and Dhh as well as agonists, such as e.g. SAG (smoothened agonist). Furthermore, depletion of FoxO1 or Pdx1 or Foxa2 or any other 1 cell specific transcription factor or of β cell maintaining cytokines may also be employed in order to induce de-differentiation (Landsman, Parent et al. 2011, Pan and Wright 2011, Talchai, Xuan et al. 2012, Puri, Akiyama et al. 2013, Gao, McKenna et al. 2014). Such a depletion can be achieved without further ado, e.g. by using RNA interference or depleting antibodies.

It will be appreciated that in the latter two alternatives, cells culture conditions comprising serum, preferably between 1 to 10% of serum, can be employed.

It is well known in the art how to test whether the cell culture conditions induce the de-differentiation of mature β cells. For example, the loss of maturation, i.e. the de-differentiation, can be detected by the loss of markers of mature cells, such as Fltp, either alone or in combination with other maturation markers, such as e.g. Ucn3, as detailed above. In addition, the down-regulation of genes specifically expressed in mature β cells and the up-regulation of genes specifically expressed in immature progenitor β cells can be analysed, as detailed herein above, to confirm a de-differentiation of the cells.

The cell population comprising mature β cells may be a primary cell population, such as isolated endocrine cells, obtained from pancreas, or parts thereof such as e.g. the islets of Langertans. Moreover, the cell population may also be a tissue preparation, such as for example (an) isolated, intact islet(s) of Langerhans. Further, this screening assay of the present invention may also be carried out in vivo in a suitable non-human animal model. Preferably, said non-human animal model is a mammalian animal, such as e.g. a rodent, preferably a mouse, a rat or a rabbit; a pig, a dog, a cat or a non-human primate. For example, de-differentiation has been described in animal models (Talchai, Xuan et al. 2012). Accordingly, a test compound could be screened, or an identified lead compound could be verified, in such a model. Most preferably, this screening method of the present invention is an in vitro method.

The cell population may comprise any amount of mature β cells, as long as mature β cells are present in detectable amounts. Preferably, the cell population comprises at least 5% mature β cells, such as at least 10% mature β cells, more preferably at least 20% mature β cells, even more preferably at least 30%, such as at least 40%, at least 50%, at least 60%, at least 70% or even more preferably at least 80% mature β cells. For example, when explant cultures are directly used as the cell population, the cell population typically comprises about 80% mature β cells. It is also preferred that the cell population comprises at least 90% mature β cells, such as at least 95% mature β cells, at least 98% mature β cells and most preferably, the cell population comprises 100% mature β cells, i.e. all of the β cells in the cell population are mature β cells and no immature progenitor β cells are present in detectable amounts. Such a degree of purity may e.g. be obtained by sorting the cell population in order to enrich for mature β cells, for example by using FACS sorting.

In those cases where the cell population does not comprise 100% mature β cells, it is preferred that the remaining cells are selected from immature progenitor β cells that have not yet differentiated or have de-differentiated, as well as other cells naturally present in tissues comprising β cells, such as e.g. the pancreas. Such other cells include e.g. ductal cells, acinar cells, or other endocrine cells of the islet of Langerhans, such as e.g. α-, PP-, δ-, and ε-cells, and fibroblasts. Typically, however, when using primary islet cell preparations, such non-endocrine cells disappear during culture and represent less than 1% of the total cells of the cell population. More preferably, the cell population does not comprise any α-, PP-, δ-, and ε-cells. Most preferably, the cell population consists of mature β cells, i.e. all of the cells in the cell population are mature β cells and no other cells are present.

Means and methods of enriching a cell population to the desired degree of purity have been described herein above.

In accordance with this method of the invention, this cell population is cultured under de-differentiating conditions and in the presence of a test compound.

Any of the compounds recited herein above can be assayed as a test compound in accordance with this method of the present invention of identifying a compound suitable for preventing the de-differentiation of mature β cells.

In a second step, the expression level of the biomarker Fltp is determined in the β cells cultured in step (a). The methods described herein above can also be employed with regard to this embodiment. In addition, the considerations concerning the determination of Fltp expression levels in mixed populations detailed herein above with regard to the method of identifying a compound suitable for differentiating immature progenitor β cells into mature β cells apply mutatis mutandis to this method of identifying a compound suitable for preventing the de-differentiation of mature β cells.

The expression level of Fltp determined in the second step of this method of the invention is then compared to the expression level of Ftp in the cell population comprising mature β cells prior to the culture in step (a). i.e. to control values of Fltp expression. As detailed above for the method of identifying a compound suitable for differentiating immature progenitor β cells into mature β cells, several possibilities exist in this regard. For example, the expression level of Ftp can be determined in the cell population, or a part thereof, directly prior to carrying out the cultivation step (a). Alternatively, a starting cell population may be divided and one part is used for determining the expression level of Fltp prior to treatment and the second part is used in step (a) of this method of the invention. Determining this control expression level of Ftp may be carried out prior to performing the present method of the invention, such that the determined values may be used as a reference at later times whenever a cell population is screened in accordance with the method of the present invention; or may be determined in parallel each time a cell population is screened in accordance with the method of the present invention. Such a control value may also be determined only once and stored as a standard for all future tests. As detailed herein above with regard to the method of identifying a compound suitable for differentiating immature progenitor β cells into mature β cells, said control value is obtained from a sample that needs to be identical in its characteristics to the cell population used in the assay. Accordingly, it is understood that said control sample is not further cultured under conditions that change these characteristics. The preferred time points of determining the expression level of Ftp described above apply mutatis mutandis also to this method.

If this step of comparison of the treated cell population with the untreated cell population shows that the expression level of Fltp is substantially identical, then this finding indicates that the compound is suitable for preventing the de-differentiating of mature β cells.

In accordance with all embodiments of the present invention, the expression level of Fltp is considered to be "substantially identical", if the expression level between the two samples differs by less than 10%, preferably by less than 5%, more preferably by less than 4%, such as by less than 3%, such as by less than 2%, and more preferably by less than 1%. Even more preferably, the expression level between the two samples differs by less than 0.5% and most preferably, by less than 0.1%. Even more preferably, the expression level between the two samples differs only by deviations caused by the limits of accuracy of established detection methods, in which case the expression levels are considered to be identical.

As discussed herein above, recent findings have shown that β cell de-differentiation contributes to β cell failure in type 2 diabetes. Accordingly, this method of the present invention enables for the identification of novel lead compounds that could prove useful in the treatment type 2 diabetes.

In a preferred embodiment of this method of the invention, the method comprises providing a cell population comprising mature β cells and
(a) culturing one portion of said cell population comprising mature β cells in the presence of a test compound, wherein the cells are cultured under conditions that induce the de-differentiation of said cells; and
(b) culturing a second portion of said cell population comprising mature β cells in the absence of a test compound, wherein the cells are cultured under conditions that induce the de-differentiation of said cells; and
(b) subsequently determining the expression level of the biomarker Flattop (Fltp) in
  (i) the cells cultured in (a), and
  (ii) the cells cultured in (b);
wherein an increased expression level of Fltp in the cells cultured in step (a) as compared to the expression level of Fltp in the cells cultured in step (b) is indicative of a compound suitable for preventing the de-differentiating of mature β cells.

In another preferred embodiment of the method of identifying a compound suitable for differentiating immature progenitor β cells into mature β cells or the method of identifying a compound suitable for preventing the de-differentiating of mature β cells, the test compound is a compound that activates planar cell polarity (PCP).

The conserved planar cell polarity (PCP) pathway regulates the orientation of cells and organelles within the plane of a tissue and thus critically determines the function of mature cells in the context of an organ ((Seifert and Mlodzik 2007, Wang and Nathans 2007, Wallingford 2012). Activation of the non-canonical Wnt/PCP signaling pathway triggers the asymmetric localization of core PCP molecules and causes cytoskeletal rearrangements to provide three-dimensional (3D) tissue polarity information for cells (Wallingford and Mitchell 2011). The core PCP pathway components Van Gogh (Vangl), Flamingo/Cadherin EGF LAG seven-pass G-type receptor (Fmi/Celsr). Frizzled (Fzd), Dishevelled (Dvl), and Prickle (Pk) are conserved during evolution (Wallingford and Mitchell 2011).

Activation of the Wnt/PCP signaling pathway can be achieved via stimulation of the Wnt receptors (Frizzled (Frz) receptors) and co-receptors (Niehrs 2012), such as Ror1, ROR2, RYK, MUSK, PTK7, Syndecan or Glypican, via either naturally occurring ligands, small molecule compounds and/or antibodies having an agonistic effect on these receptors. Accordingly, compounds that activate planar cell polarity (PCP) can be divided into ligands, intracellular mediators and core PCP components. For example, Wnt5a and Wnt11 as well as the atypical cadherins Fat and Dachsous are naturally occurring ligands that act via Wnt receptors and co-receptors. In addition, anti-Ror1- and anti-Ror2-antibodies are known in the art that can act as activators. Antibodies against Wnt5a, Wnt11 and Ror1/2 are commercially available, for example from R&D and other suppliers. Dishevelled (Dvi) and Prickle (Pk) are intracellular mediators, while Van Gogh (Vangl1/2) and Flamingo/Cadherin EGF LAG seven-pass G-type receptor (Fmi/Celsr1, 2 and 3) are core PCP components. All these compounds are well known in the art.

Moreover, the Wnt/PCP pathway also activates intracellular molecules such as small Rho GTPases, DAAM, RHOA, RACI, JNK, ROCK1 and ROCK2 (Seifert and Mlodzik 2007, Wallingford and Mitchell 2011, Niehrs 2012, Ezan and Montcouquiol 2013, Matis and Axelrod 2013). Accordingly, agonists of such intracellular PCP activators can also be employed as test compounds in the methods of the invention.

In addition, the term "a compound that activates planar cell polarity (PCP)" also refers to activators and inhibitors of components of this pathway, i.e. compounds that indirectly activate the Wnt/PCP signaling pathway by modulating the activity of one of its components. For example, it is known in the art that the PCP signaling pathway and the Hippo signaling pathway, which integrates physical signaling to regulate cell growth, are interconnected via Fat (Lawrence and Casal 2013). Accordingly, compounds that activate the Hippo signaling pathway might activate downstream signaling molecules of the PCP pathway. For example, the polarity regulating transcription factor Foxa2, which is regulated by Hippo signaling (Sawada, Nishizaki et al. 2005), is known to directly target Flattop (Weedon, Cebola et al. 2014), showing that Fltp activation can also be induced via indirect transcription factors that mediate e.g. polarity, PCP and Hippo signaling.

In a more preferred embodiment of the method of the invention of identifying a compound suitable for differentiating immature progenitor β cells into mature β cells or the method of the invention of identifying a compound suitable for preventing the de-differentiating of mature β cells, the compound that activates planar cell polarity (PCP) is an activator of the non-canonical Wnt/PCP pathway.

The term "activator", as used herein, is defined as a compound enhancing the activity of a target molecule, preferably by performing one or more of the following effects: (i) the transcription of the gene encoding the protein to be activated is enhanced, (ii) the translation of the mRNA encoding the protein to be activated is enhanced, (iii) the protein performs its biochemical function with enhanced efficiency in the presence of the activator, and (iv) the protein performs its cellular function with enhanced efficiency in the presence of the activator. Accordingly, the term "activator" encompasses both molecules that have a directly activating effect on the specific pathway but also molecules that are indirectly activating, e.g. by interacting for example with molecules that negatively regulate (e.g. suppress) said pathway.

Compounds suitable to achieve the effect described in (i) include compounds modulating the transcriptional machinery and/or its interaction with the promoter of said gene and/or with expression control elements remote from the promoter such as enhancers. Compounds suitable to achieve the effect described in (ii) comprise compounds modulating the translational machinery. Compounds suitable to achieve the effect described in (iii) modulate the molecular functions of the protein to be activated. Compounds suitable to achieve the effect described in (iv) include compounds which do not necessarily bind directly to the target protein, but still modulate their activity, for example by binding to and/or modulating the function or expression of members of a pathway which comprises the target protein. These members are preferably upstream of the protein to be activated within said pathway.

Such compounds include, without being limiting, all of the above recited compounds, such as e.g. small molecules, antisense nucleic acid molecules, siRNA, shRNA, miRNA, antibodies, aptamers, ribozymes or peptides such as soluble peptides.

Preferably, the level of activity of the non-canonical Wnt/PCP pathway in the presence of an activator is 10% more than the activity of the non-canonical Wnt/PCP pathway in the absence of the activator, more preferred, the level of activity is 25% more, such as 50% more. Yet more preferred are activators enhancing the level of activity of the non-canonical Wnt/PCP pathway to 75%, 80%, 90% or 100% more than the activity of the non-canonical Wnt/PCP pathway in the absence of the activator.

The term "non-canonical Wnt/PCP pathway" is well known in the art and has been described ((Seifert and Mlodzik 2007, Wallingford and Mitchell 2011, Niehrs 2012, Ezan and Montcouquiol 2013, Matis and Axelrod 2013). Non-canonical Wnt/PCP pathway ligands, including, for example Wnt5a and Wnt11, bind to a Wnt/PCP receptor and a co-receptor including, for example. Frz 1, 2, 3, 6, or Ror1/2, causing a signal to be transduced to proteins including, for example, small GTPases, Cdc42, RhoA, Inturned, Fuzzy, and in particular Flattop. This results in the activation of PI3K, JNK, RHOA, ROCK1/2 and other kinases, which then leads to cytoskeletal arrangements.

Accordingly, the term "activator of the non-canonical Wnt/PCP pathway" refers to an activator of any one of the above recited molecules that form part of this signalling pathway. Preferably, the activator of the non-canonical Wnt/PCP pathway is selected from the group consisting of an activator of Wnt5a, an activator of Wnt11, other Wnt ligands activating the PCP pathway, ligands that activate the co-receptors ROR1,2, RYK, MUSK, PTK7, Syndecan or Glypican, as well as antibodies or alternative binding molecules, such as those described herein above, or small molecules that act agonistic on Wnt receptors and co-receptors.

The present invention further relates to a method of differentiating immature progenitor β cells into mature β cells, the method comprising: inducing the expression of Fltp in a cell population comprising immature progenitor β cells.

The definitions and preferred embodiments provided herein above, in particular with regard to immature progenitor β cells, mature β cells, cell populations comprising immature progenitor β cells and differentiation apply mutatis mutandis to this method of the present invention.

In accordance with this method, immature progenitor β cells are differentiated into mature β cells. This method may be performed in vivo or in vitro. Preferably, the method is an in vitro method.

In accordance with this embodiment, it is particularly preferred that the immature progenitor β cells are obtained from embryonic or pluripotent stem or progenitor cells.

β cell differentiation is achieved, in accordance with this method of the invention, by inducing the expression of Fltp in said cells. Means of inducing the expression of Fltp are not particularly limited. For example, Fltp expression can be induced by culturing immature progenitor β cells in the presence of an activator of the non-canonical Wnt/PCP pathway, as Ftp has been found in accordance with the present invention to be a downstream effector gene of this pathway. Compounds that induce the expression of Fltp are also referred to herein as "activators of Fltp expression".

In addition, expression of Fltp can be induced by culturing immature progenitor β cells at a high density, such as e.g. 90% confluency or cell densities known to trigger contact inhibition and polarization. By growing immature progenitor β cells at such high densities, the cell-cell contacts, induced polarization and contact inhibition between these cells lead to maturation of the cells.

Mature β cells obtained in accordance with this embodiment of the invention are particularly useful for therapeutic approaches, such as e.g. for β cell replacement therapy.

In a preferred embodiment of this method of differentiating immature progenitor β cells into mature β cells, the expression of Fltp in the cells is induced by culturing the cells in the presence of a compound selected from the group consisting of Wnt5a, Wnt11, Wnt3a, at least one activator of the co-receptors ROR1,2, RYK, MUSK, PTK7, Syndecan and Glypican and/or a compound identified by the method of the invention of identifying a compound suitable for differentiating immature progenitor β cells into mature β cells.

Wnt5a is well known in the art and has been described (Yang 2012, Baarsma, Konigshoff et al. 2013). Wnt5a for use in cell culture can be obtained commercially, e.g. from R&D System. Preferred amounts of Wnt5a to be employed are between about 50 and about 200 ng/ml, more preferably between about 70 and about 150 ng/ml, such as for example between about 90 and about 120 ng/ml and most preferably the amount is about 100 ng/ml.

Wnt11 is well known in the art and has been described (Baarsma, Konigshoff et al. 2013). Wnt11 for use in cell culture can be obtained commercially, e.g. from R&D System. Preferred amounts of Wnt11 to be employed are between about 50 and about 200 ng/ml, more preferably between about 70 and about 150 ng/ml, such as for example between about 90 and about 120 ng/ml and most preferably the amount is about 100 ng/ml.

Wnt3a is well known in the art and has been described (Baarsma, Konigshoff et al. 2013). Wnt3a for use in cell culture can be obtained commercially, e.g. from R&D Preferred amounts of Wnt3a to be employed are between about 50 and about 200 ng/ml, more preferably between about 70 and about 150 ng/ml, such as for example between about 90 and about 120 ng/ml and most preferably the amount is about 100 ng/ml.

The term "activator of the co-receptors ROR1,2, RYK, MUSK, PTK7, Syndecan and Glypican" encompasses any activator of these co-receptors, i.e. it includes direct and indirect activators. Preferably, an activator of one of these co-receptors is a ligand of the respective co-receptor to be activated. Ligands that activate the co-receptors ROR1,2, RYK, MUSK, PTK7, Syndecan and Glypican for use in cell culture are well known and can be obtained commercially, e.g. from R&D. Preferred amounts of the ligands that activate the co-receptors ROR1,2, RYK, MUSK, PTK7, Syndecan and/or Glypican to be employed are between 50 and about 200 ng/ml, more preferably between about 70 and about 150 ng/ml, such as for example between about 90 and about 120 ng/ml and most preferably the amount is about 100 ng/ml.

The present invention further relates to a method of preventing de-differentiating of mature β cells, the method comprising inducing or maintaining the expression of Fltp in mature β cells.

The definitions and preferred embodiments provided herein above, in particular with regard to mature β cells, de-differentiation as well as the induction of Fltp expression apply mutatis mutandis to this method of the present invention.

In accordance with this method, the de-differentiation of mature β cells is prevented, i.e. the cells are maintained in a mature, functional state. This method may be performed in vivo or in vitro. Preferably, the method is an in vitro method. In the latter case, the method comprises: culturing mature β cells in vitro under conditions suitable to induce or maintain the expression of Fltp in the cells.

Means of inducing the expression of Fltp have been defined herein above. It will be appreciated that these means lead to the maintenance of Fltp expression in those cases where Fltp is already expressed.

In a preferred embodiment of the method of preventing de-differentiating of mature β cells, the expression of Fltp in the cells is induced by culturing the cells in the presence of a compound selected from Wnt5a, Wnt11, Wnt3a, an activator of at least one of the co-receptors ROR1,2, RYK, MUSK, PTK7, Syndecan and/or Glypican and/or a compound identified by the method of the invention of identifying a compound suitable for preventing the de-differentiating of mature β cells.

These compounds have been defined herein above.

The present invention further relates to a kit for distinguishing mature β cells from immature progenitor β cells, the kit comprising: (a) means for determining the presence or absence of the biomarker Flattop (Fltp), and (b) instructions how to use the kit.

Whereas the term "kit" in its broadest sense does not require the presence of any other compounds, vials, containers and the like other than the recited components, the term "comprising", in the context of the kit of the invention, denotes that further components can be present in the kit. Non-limiting examples of such further components include preservatives, buffers for storage, enzymes etc.

Where several components in accordance with (a) are comprised in the kit, the various components of the kit may be packaged in one or more containers such as one or more vials. Consequently, the various components of the kit may be present in isolation or combination. The containers or vials may, in addition to the components, comprise preservatives or buffers for storage. In addition, the kit contains instructions for use.

"Means for determining the presence or amount of the biomarker Fltp" are well known in the art and include, without being limiting, antibodies specifically binding (i.e. without cross-reacting with unrelated markers) to Fltp in accordance with the present invention; nucleic acid probes for the detection of Ftp on the nucleic acid level, such as for example nucleic acid probes specifically hybridising with parts or full-length nucleic acid molecules (DNA as well as RNA) encoding Fltp; sequencing primers for the analysis and detection of specific sequences of the DNA encoding Fltp, e.g. sequences containing mutations known to interfere with the expression of Fltp; or amplification primers for amplifying transcribed nucleic acid molecules of Fltp.

Also encompassed by this embodiment is that the kit comprises further means for determining the presence or amount of biomarkers or reference markers different from the biomarker of the present invention, i.e. Fltp.

Such biomarkers different from Fltp include, without being limiting, additional β cell maturation markers, such as for example Urocortin 3 (Blum, Hrvatin et al. 2012), as well as general β cell markers, such as Nkx6.1, Insulin, Pdx1 or any other β cell specific marker.

The term "reference marker", as used herein, refers to a marker that is present in β cells at substantially constant levels. In other words, the expression level of a reference marker should not differ (apart from deviations caused by the limits of accuracy of established detection methods) between β cells of different maturation levels. Due to the essentially unchanged amounts of such reference markers in different β cell populations, they may be employed to normalise values of biomarker amounts, e.g. by comparison between the expression levels of said non-changing reference marker with the expression level of the biomarker of interest. Often, housekeeping genes are used as reference markers. Examples of reference markers include, without being limiting, GAPDH, RPLP0, PGK1, HSP90AB1, cyclophilin, actin, HPRT, RN18s and many more. Further examples are described in literature (Velculescu, Madden et al. 1999, Eisenberg and Levanon 2003).

If the kit comprises such additional means for determining the presence or amount of biomarkers or reference markers different from Fltp in accordance with the present invention, it is preferred that at most 10.000 such additional markers are comprised in the kit of the invention. More preferably, at most 5.000, such as for example at most 2.000 and more preferably at most 1.000 additional nucleic markers are comprised in the kit of the invention. More preferably, at most 800, such as for example at most 600, more preferable at most 400, such as for example at most 300, at most 200, at most 100 and more preferably at most 80 additional markers are comprised in the kit of the invention. Even more preferably, at most 50, such as for example at most 40, more preferable at most 30, such as for example at most 20, at most 10, at most 9, at most 8, at most 7, at most 6, at most 5, at most 4, at most 3, at most 2 and yet more preferably at most 1 additional marker(s) is/are comprised in the kit of the invention. Also preferred is that the kit of the invention only comprises means for determining the presence or amount of Fltp.

The present invention additionally relates to a pharmaceutical composition for use in treating or preventing diabetes, wherein the pharmaceutical composition comprises (an) activator(s) of Fltp expression. Furthermore, the present invention relates to a method of treating or preventing diabetes, the method comprising administering a pharmaceutical composition comprising (an) activator(s) of Fltp expression to a subject in need thereof.

In accordance with the present invention, the term "pharmaceutical composition" relates to a composition for administration to a patient, preferably a human patient. The pharmaceutical composition of the invention comprises the compounds recited above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include sodium chloride solutions, phosphate buffered sodium chloride solutions, water, emulsions, such as oil/water emulsions, various types of wetting agents, sterile solutions, organic solvents etc. Preferably the carrier is a parenteral carrier, more preferably a solution that is isotonic with the blood of the recipient. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or further immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

Compositions comprising such carriers can be formulated by well-known conventional methods. Generally, the formulations are prepared by contacting the components of the pharmaceutical composition uniformly and intimately with liquid carriers or finely divided solid carriers or both.

Then, if necessary, the product is shaped into the desired formulation.

The components of the pharmaceutical composition to be used for therapeutic administration must be sterile. Sterility can for example be accomplished by filtration through sterile filtration membranes (e.g., 0.2 micron membranes).

These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The pharmaceutical composition may be for administration once or for a regular administration over a prolonged period of time. Generally, the administration of the pharmaceutical composition should be in the range of for example 10 µg/kg of body weight to 2 g/kg of body weight for a single dose. However, a more preferred dosage might be in the range of 100 µg/kg to 1.5 g/kg of body weight, even more preferably 1 mg/kg to 1 g/kg of body weight and even more preferably 5 mg/kg to 500 mg/kg of body weight for a single dose. The length of treatment needed to observe changes and the interval following treatment for responses to occur vary depending on the desired effect. The particular amounts may be determined by conventional tests which are well known to the person skilled in the art.

Administration of pharmaceutical compositions of the invention may be effected by different ways, e.g., by parenteral (e.g. including intravenous, intramuscular, intraperitoneal, intrasternal, subcutaneous and intraarticular injection as well as infusion), intradermal, intranasal or intrabronchial administration.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic water-for-injection. Preservatives and other additives may also be present such as, for example, antimicrobials, anti-oxidants, chelating agents, and inert gases and the like. The pharmaceutical composition may comprise further agents depending on the intended use of the pharmaceutical composition. Since the pharmaceutical preparation of the present invention relies on the above mentioned compounds, it is preferred that these mentioned further agents are only used as a supplement, i.e. at a reduced dose as compared to the recommended dose when used as the only drug, so as to e.g. reduce side effects conferred by the further agents.

A definition of the term "activator of Fltp expression", used interchangeably with the term "inducer of Fltp expression", has been provided herein above and applies mutatis mutandis also to the pharmaceutical composition of the present invention.

It is well known in the art that one of the results of gluco-lipotoxicity is that β cells die and the architecture of the islet of Langerhans changes due to inflammation. In addition to stopping inflammation, the restoration of the tissue architecture is therefore a promising approach to regenerate β cell functionality in the islet of Langerhans. Activators of Fltp expression, as shown herein, provide a valuable tool to restore tissue polarity and enhance the maturation of β cells, thereby restoring the functionality of the islet of Langerhans.

In a preferred embodiment of the pharmaceutical composition of the invention, the activator of Fltp expression is selected from the group consisting of Wnt5a, Wnt11, Wnt3a, an activator of at least one of the co-receptors ROR1,2, RYK, MUSK, PTK7, Syndecan and Glypican and/or a compound identified by the method of the invention of identifying a compound suitable for differentiating immature progenitor β cells into mature β cells. These compounds have been defined herein above.

Unless otherwise defined, all technical and scientific terms used herein have the same meaning as commonly understood by one of ordinary skill in the art to which this invention pertains. In case of conflict, the present specification, including definitions, will control.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 5 and 7 is clearly and unambiguously envisaged in view of the claim structure. The same applies for example to the combination of claims 5, 7 and 8, etc.

The figures show:

FIG. 1: Fltp reporter expression correlates with post-natal β cell maturation and shows heterogeneity in all endocrine lineages.

(A) Representative images of single immunofluorescence stainings of pancreatic tissue for Fltp reporter and Nkx6.1 on postnatal day 1 (P1) as well as of 12 weeks old $Fltp^{ZV/+}$ animals. (B) Quantitative analysis of Fltp reporter expression in β cells during β cell maturation period in $Fltp^{ZV/+}$ mice. Values are mean±SEM (standard error of the mean); n=2 for P1, 3, 11, and n=9 for 12 weeks; ***$P<0.001$ in Fltp reporter and Nkx6.1 positive β-cells of P1 vs. 12 weeks old animals. The percentage of Fltp reporter expressing β cells increase from 45% (P1) over 70% (P11) to 80% (12 weeks). (C) Representative images of single immunofluorescence stainings of 4',6-diamidino-2-phenylindole (DAPI), Fltp reporter, and one endocrine hormone on adult pancreatic tissue. Hormones are arranged from upper to lower row as indicated (glucagon, insulin, somatostatin, and pancreatic polypeptide). (D) Quantitative analysis of Fltp reporter expression reveals heterogeneity in Fltp reporter expression in all endocrine cell types (α=47.4%, β=81.1%, δ=49.3%, PP=47.0%). Values are mean±SEM; n>30 islets. Nuclear reporter of Fltp expression (Fltp) is marked by GFP antibody (A,C).

Figure 2:
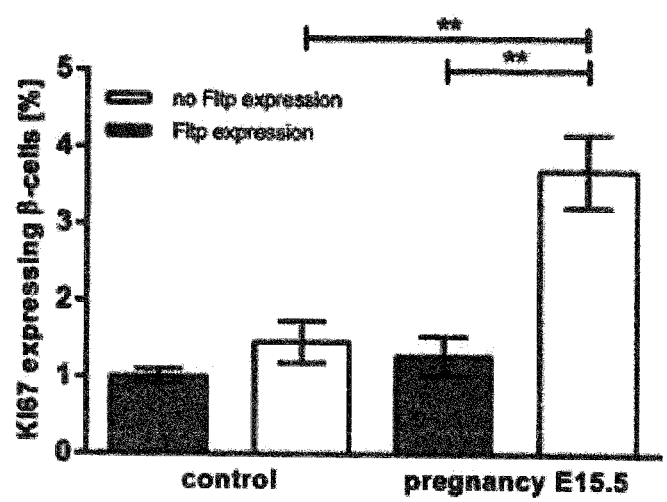
Figure 2:
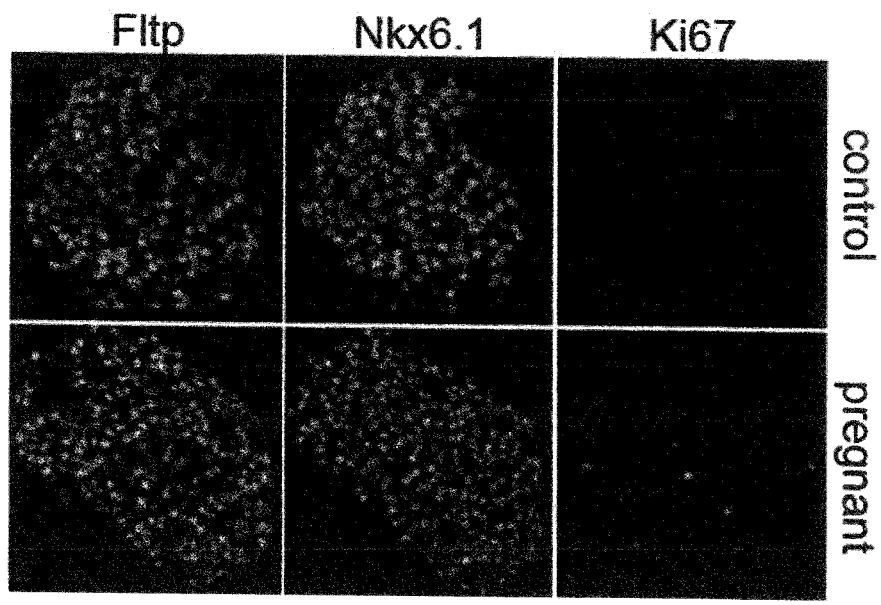
Figure 2:
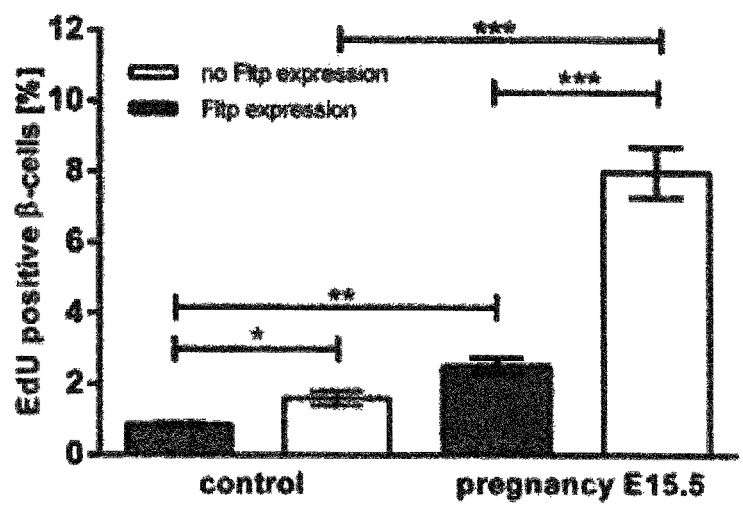
Figure 2:
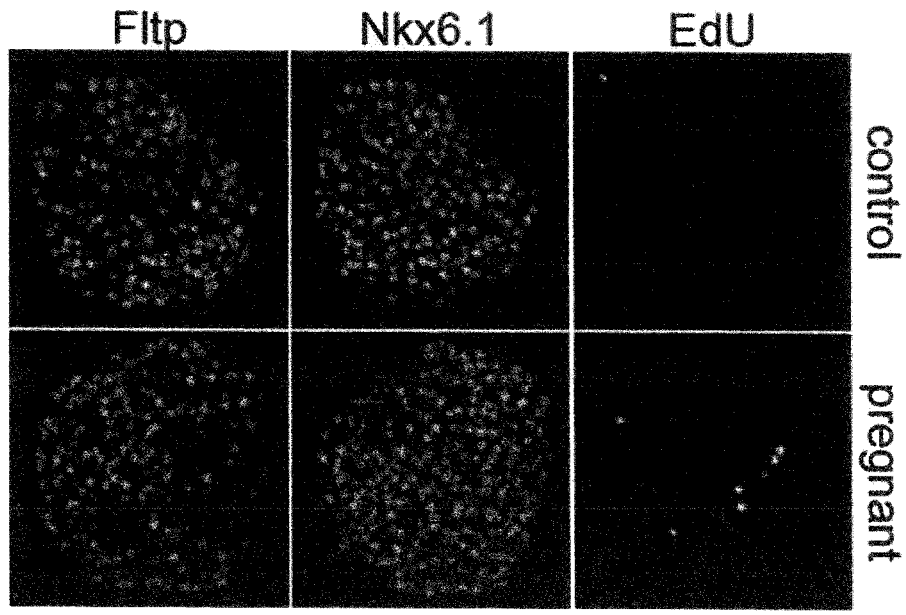
Figure 2:
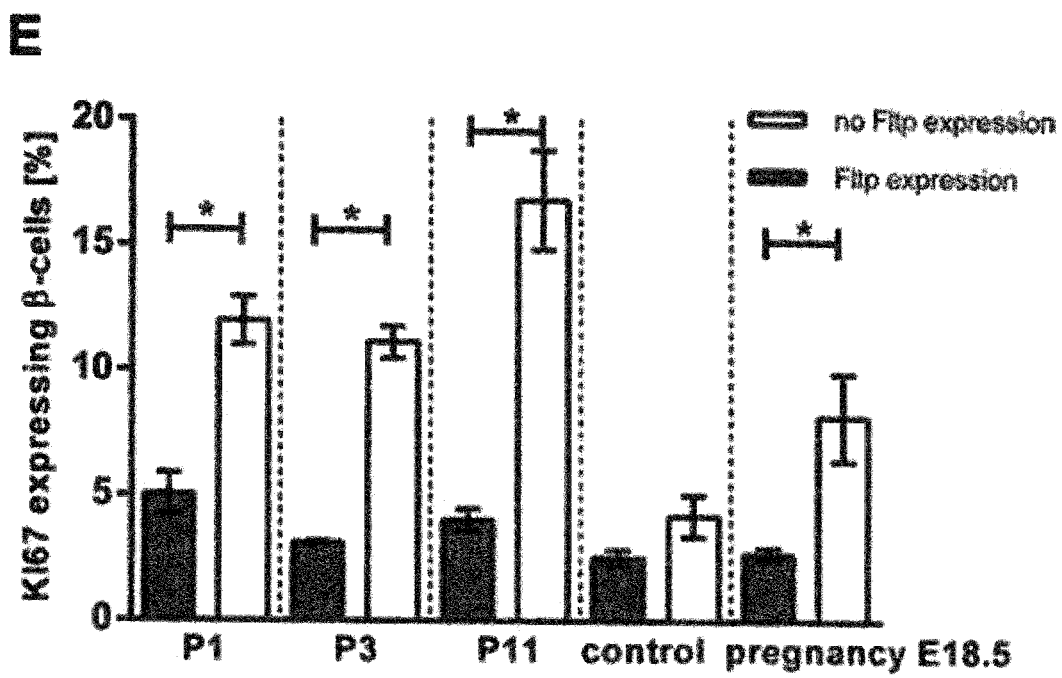
Figure 2:
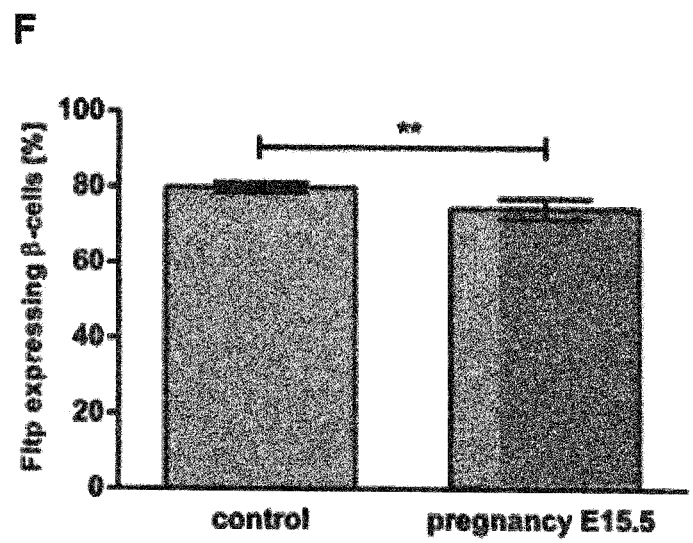

FIG. 2: β cell subpopulations exhibit differences in proliferative capacity in vivo.

(A) Quantitative analysis of Ki67 expression in β cells upon metabolic demand (pregnancy) in $Fltp^{ZV/+}$ mice. Values are mean±SEM; n=4 for control and pregnant mice embryonic day 15.5 (E15.5); $P<0.01$ in Ki67 expression in β cells which lack Fltp reporter expression vs. Fltp reporter expressing β cells in pregnant (E15.5) mice. (B) Representative images of single immunofluorescence stainings of Fltp reporter, Nkx6.1 and Ki67 on adult pancreatic tissue of the control group and pregnant mice E15.5. (C) Quantitative analysis of β cell proliferation upon metabolic demand (pregnancy) after 24 h in vivo pulse labeling using EdU in $Fltp^{ZV/+}$ mice. Values are mean±SEM; n=5 for control and pregnant mice; *$P<0.001$ in EdU marked β cells of pregnant mice (E15.5) which lack Flip reporter expression vs. Flip reporter expressing β cells of pregnant mice and vs. Fltp reporter negative β cells in control group. *$P<0.01$ in EdU marked β cells of pregnant mice (E15.5) expressing Fltp reporter vs. Fltp reporter expressing β cells of control mice. *$P<0.05$ in EdU marked β cells of control mice which lack Fltp reporter expression vs. Fltp reporter expressing β cells of control mice. (D) Representative images of single immunofluorescence stainings of Fltp reporter, Nkx6.1, and EdU on adult pancreatic tissue of the control group and pregnant group at E15.5. (E) Quantitative analysis of Ki67 expression in β cell upon metabolic demand (pregnancy) in $Fltp^{ZV/+}$ mice. Values are mean±SEM; n=2 for P1, 3, 11 and n=4 for control and pregnant mice (E18.5); *$P<0.05$ in Ki67 expression in β cells which lack Fltp reporter expression vs. Fltp reporter expressing β cells in P1, P3, P11 and pregnant (E18.5) mice. (F) Qualitative analysis of Fltp reporter expression in β cells upon metabolic demand (pregnancy E15.5). Values are mean±SEM, n=5 for control and pregnant group; **$P<0.01$ between percentage of Fltp reporter expressing β-cells compared to Fltp reporter negative β cells. Nuclear reporter of Fltp expression (Fltp) is marked by GFP antibody (B,D).

Figure 3:
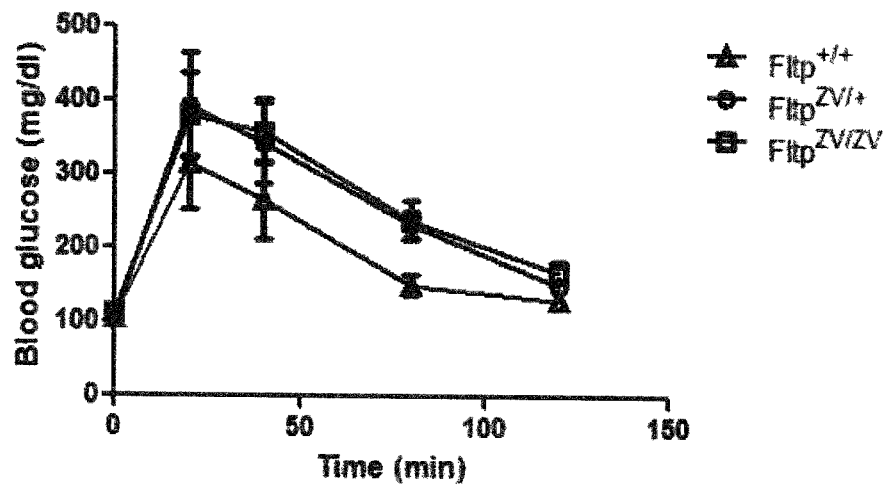
Figure 3:
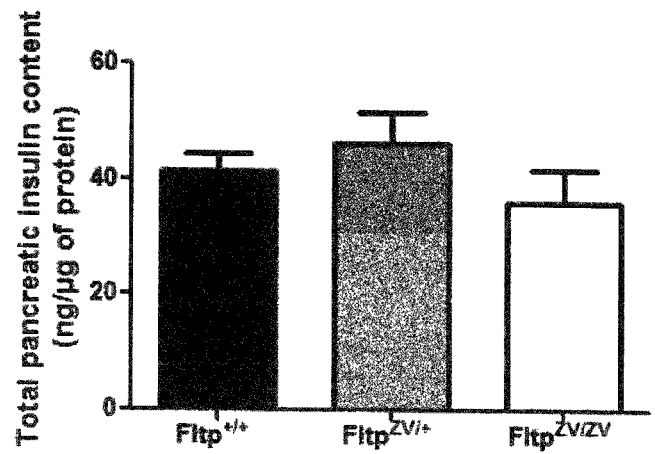
Figure 3:
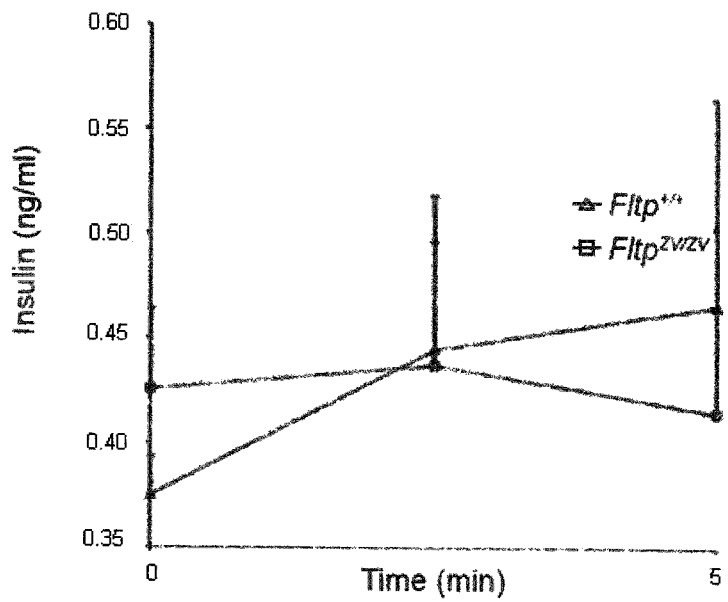
Figure 3:
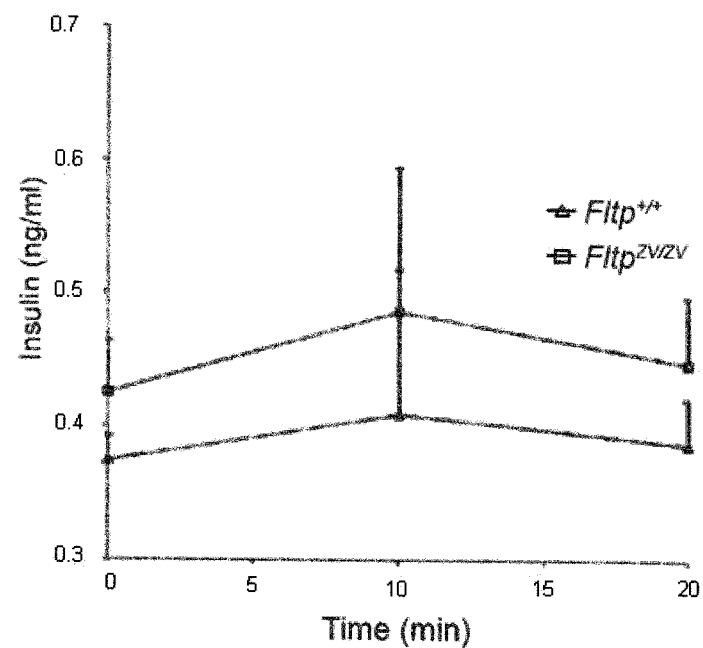

FIG. 3: $Fltp^{ZV/ZV}$ β cells show $1^{st}$ phase insulin secretion defects in vivo.

(A) $Fltp^{ZV/+}$ as well as $Fltp^{ZV/ZV}$ do not reveal altered glucose tolerance compared to $Fltp^{+/+}$. The ability of $Fltp^{ZV/+}$, $Fltp^{ZV/ZV}$ and $Fltp^{+/+}$ to handle a glucose load was assessed by using a standard GTT. Fasted male mice were injected i.p. with glucose (2 g/kg of body weight), and blood glucose levels were measured at 0, 15, 30, 60, and 120 min after glucose injection. (B) Quantitative analysis of total pancreatic insulin content in $Fltp^{+/+}$, $Fltp^{ZV/+}$ and $Fltp^{ZV/ZV}$ mice shows no major difference (n=5 per genotype). Values are mean±SEM. (C) Quantitative analysis of first phase insulin secretion reveals differences between $Fltp^{ZV/ZV}$ and $Fltp^{+/+}$ (n=4 mice per genotype). Values are mean±SEM. (D) Quantitative analysis of second phase insulin secretion shows no major difference. Values are mean±SEM.

Figure 4:
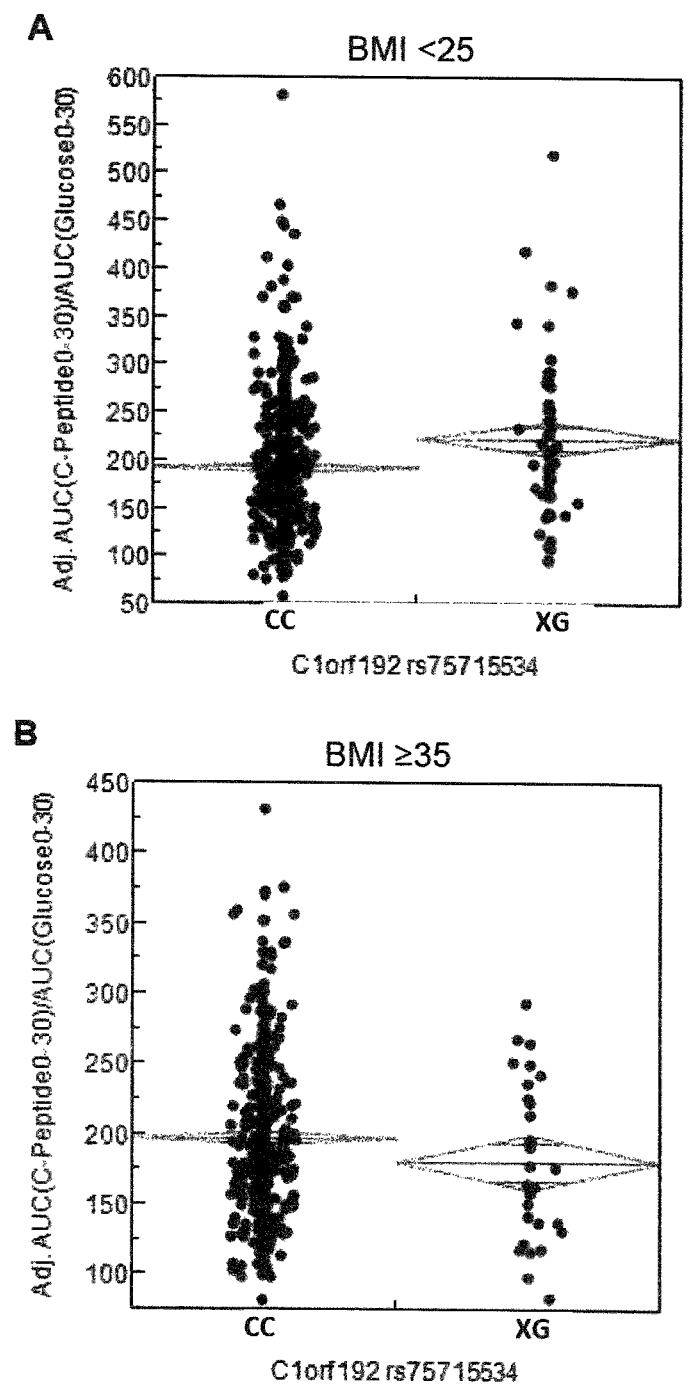

FIG. 4: FLTP intronic SNP rs7515334 significantly associates with insulin secretion defects in human.

(A) Depending on the metabolic status, the minor C1ORF192 allele rs7515334 associates with increase insulin secretion (BMI<25) and decreased insulin secretion (BMI>35) (B). Insulin secretion index adjusted for gender, age, and OGTT-derived insulin sensitivity. Genotype tested in the dominant inheritance model with XG=CG+GG. Bonferroni-corrected α-level: $p<0.0073$.

Figure 5:
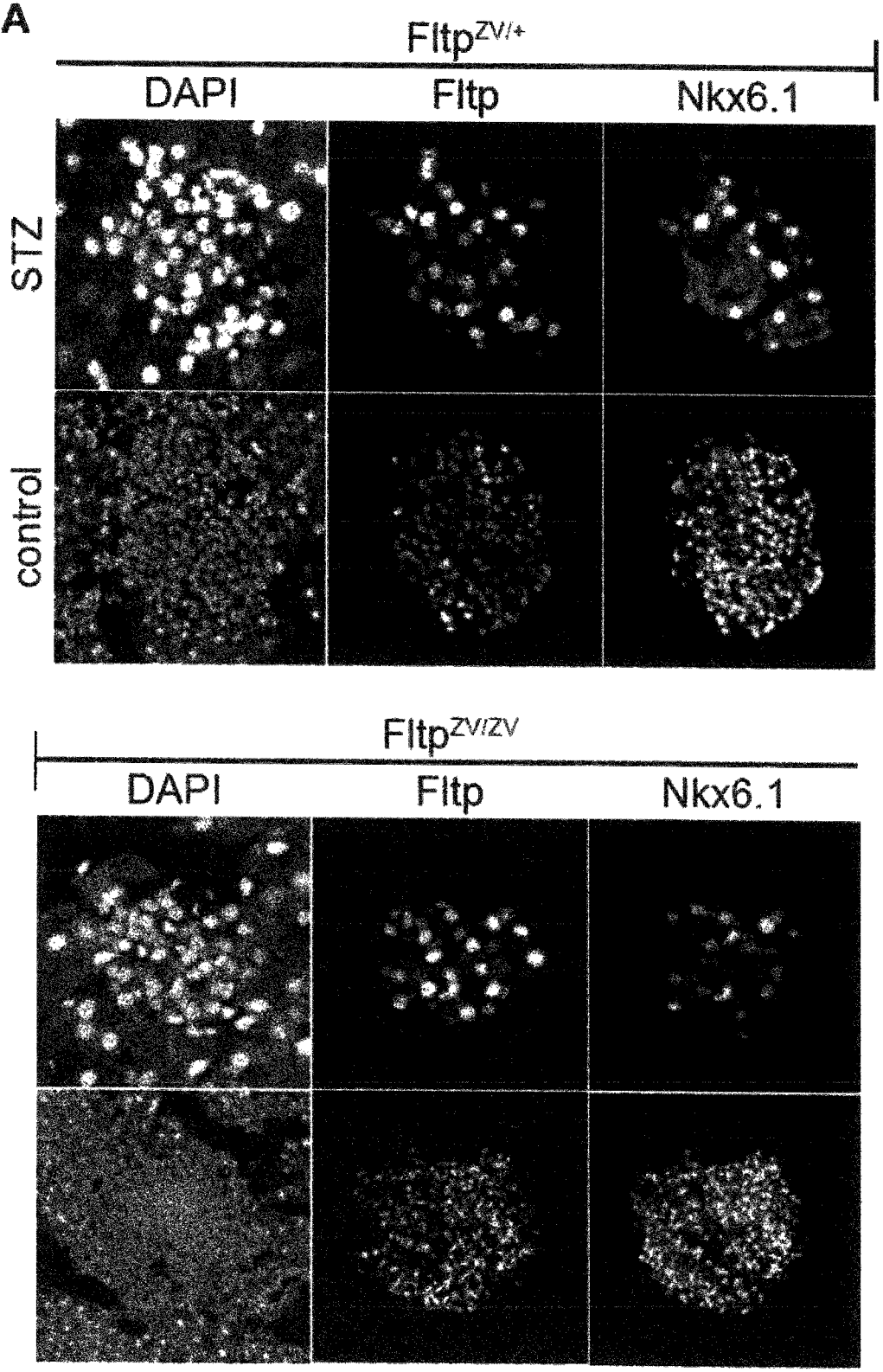
Figure 5:
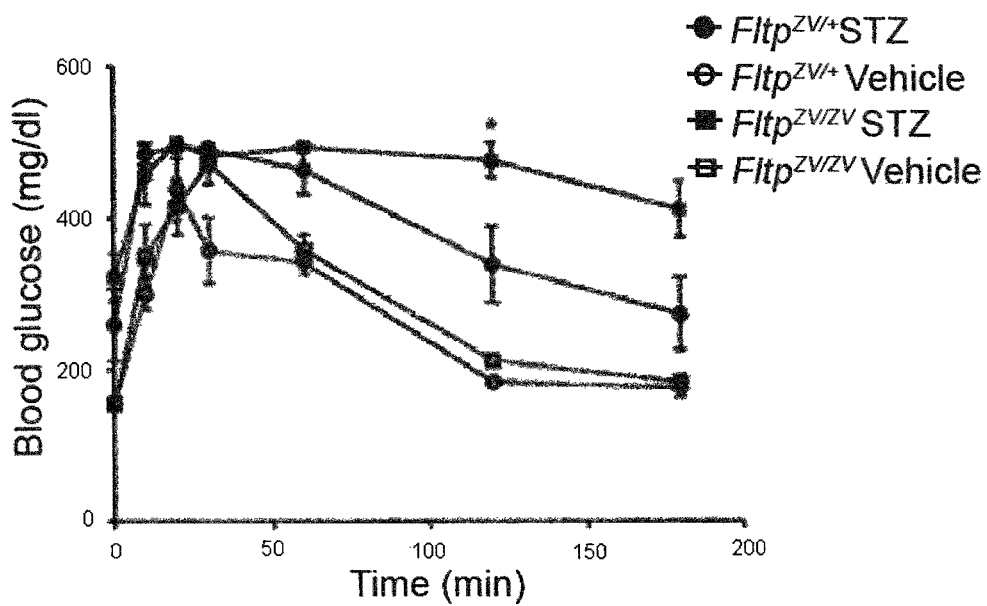
Figure 5:
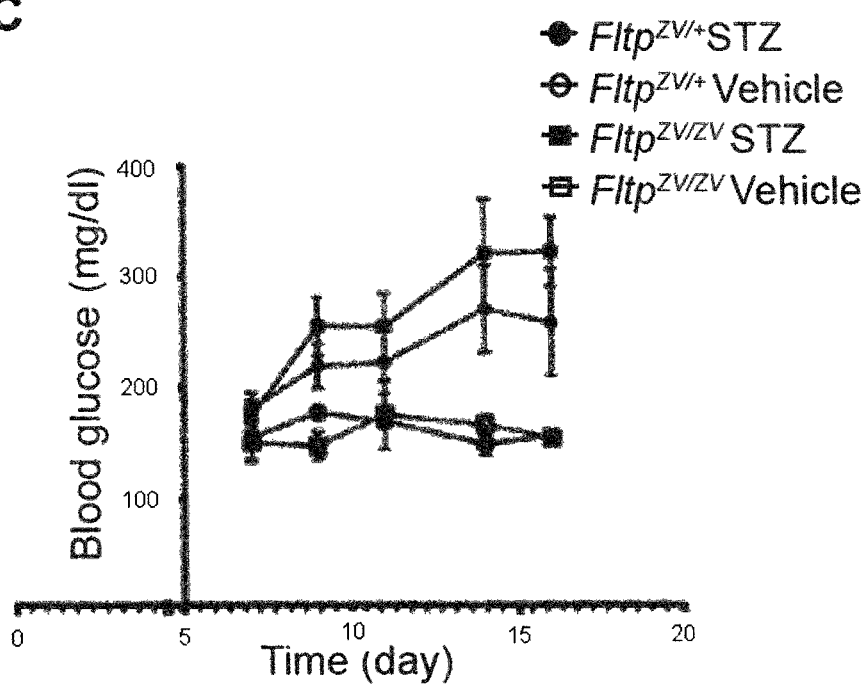

FIG. 5: $Fltp^{ZV/ZV}$ mice reveal altered susceptibility to STZ induced β cell death.

(A) Representative images of a single immunofluorescence stainings of DAPI, Fltp reporter and Nkx6.1 on adult pancreatic tissue from $Fltp^{ZV/+}$ mice treated with streptozotocin (STZ), $Fltp^{ZV/+}$ vehicle (citrate buffer) (control), $Fltp^{ZV/ZV}$ mice treated with STZ, and $Fltp^{ZV/ZV}$ vehicle (control). (B) After an overnight fast (16 h), $Fltp^{ZV/+}$ and $Fltp^{ZV/ZV}$ both treated with STZ and their respective controls, mice were injected i.p. with glucose (2 g/kg of body weight) and blood glucose levels were measured at 0, 15, 30, 60, and 120 min after injection. $Fltp^{ZV/ZV}$ mice reveal an enhanced susceptibility to STZ induced β cell damage and develop insulin resistance at an earlier time point compared to $Fltp^{ZV/+}$. Values are mean±SEM; n=4 for STZ mice and n=4 for control mice. *$P<0.05$ vs $Fltp^{ZV/+}$. (C) Whole-blood glucose concentration in $Fltp^{ZV/+}$ and $Fltp^{ZV/ZV}$ both treated with STZ-induced diabetic mice (40 mg/kg, 5 days) and their respective control mice. Nuclear reporter of Fltp expression (Fltp) is marked by GFP antibody (A).

Figure 6:
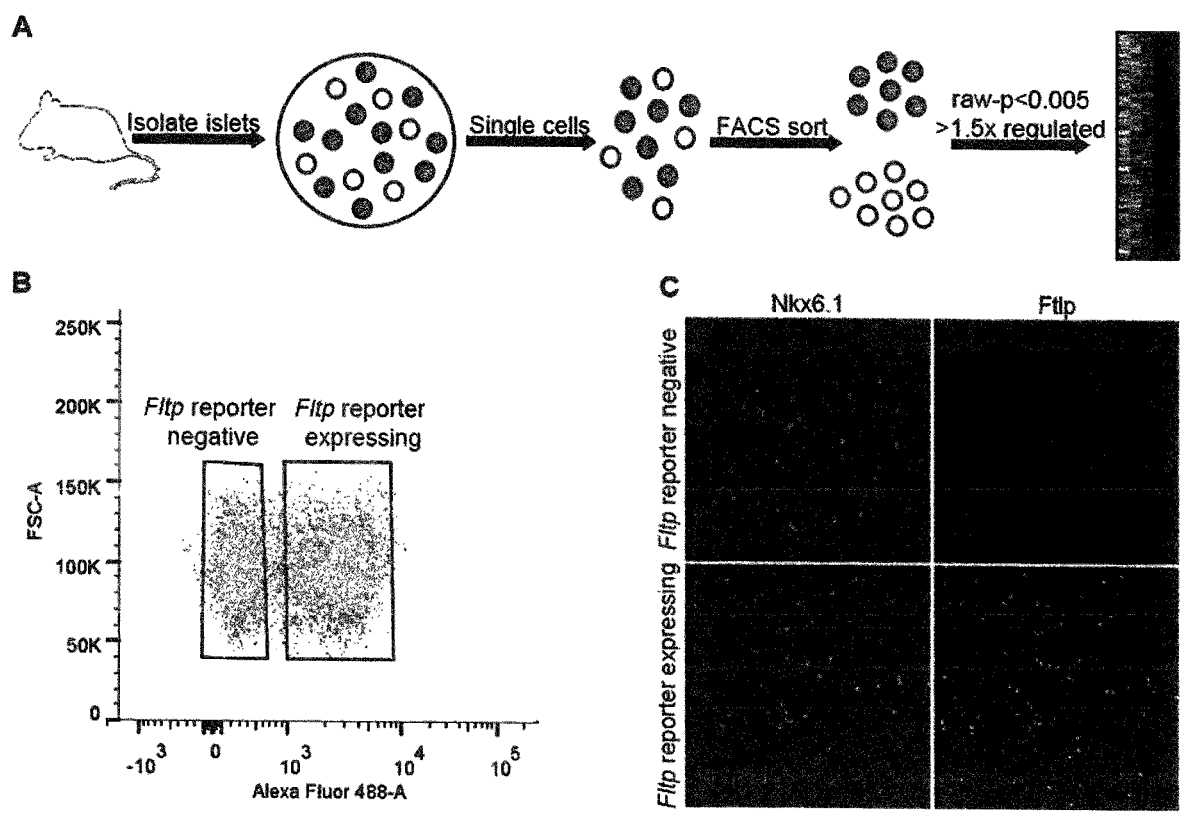
Figure 6:
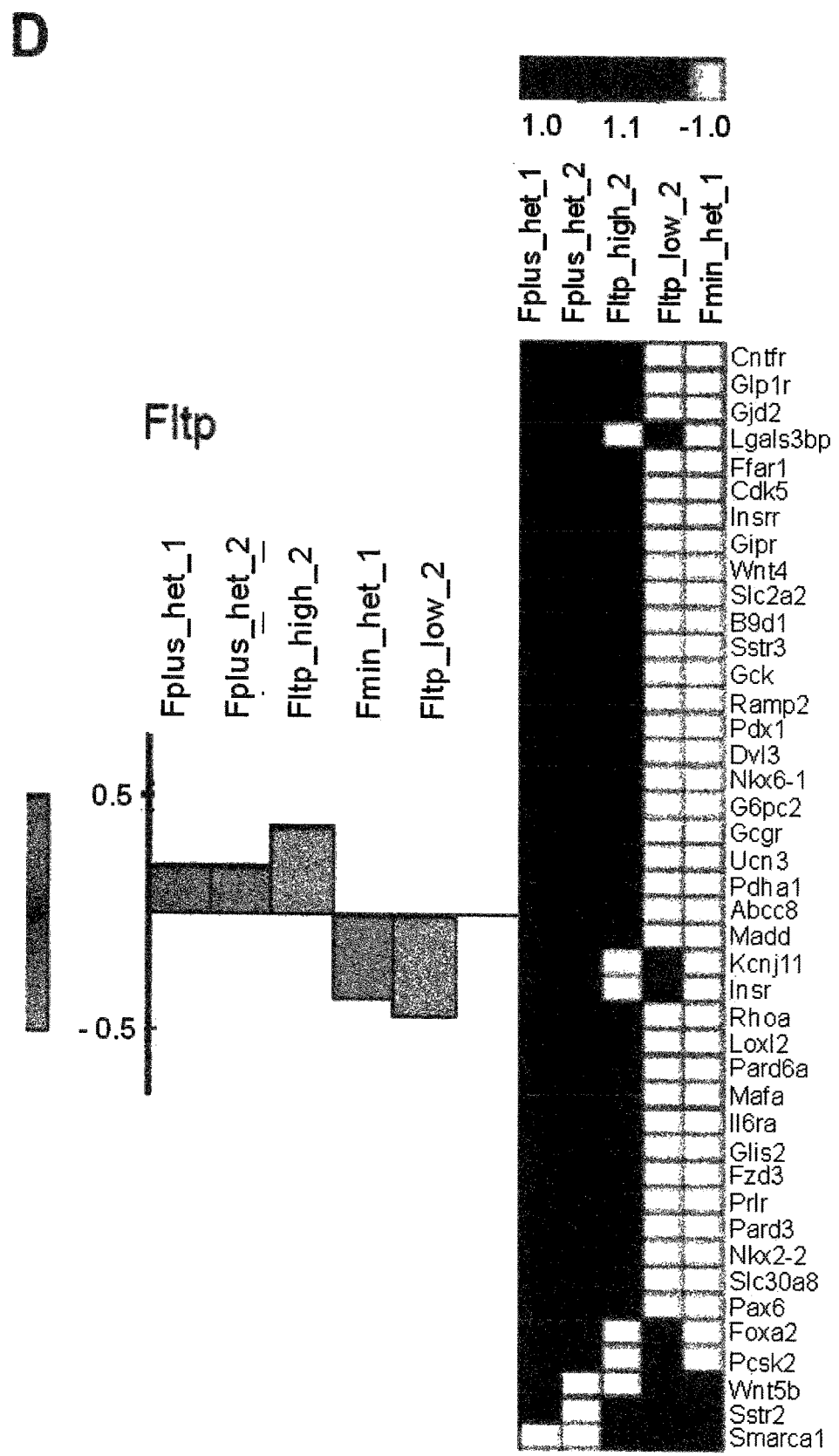
Figure 6:
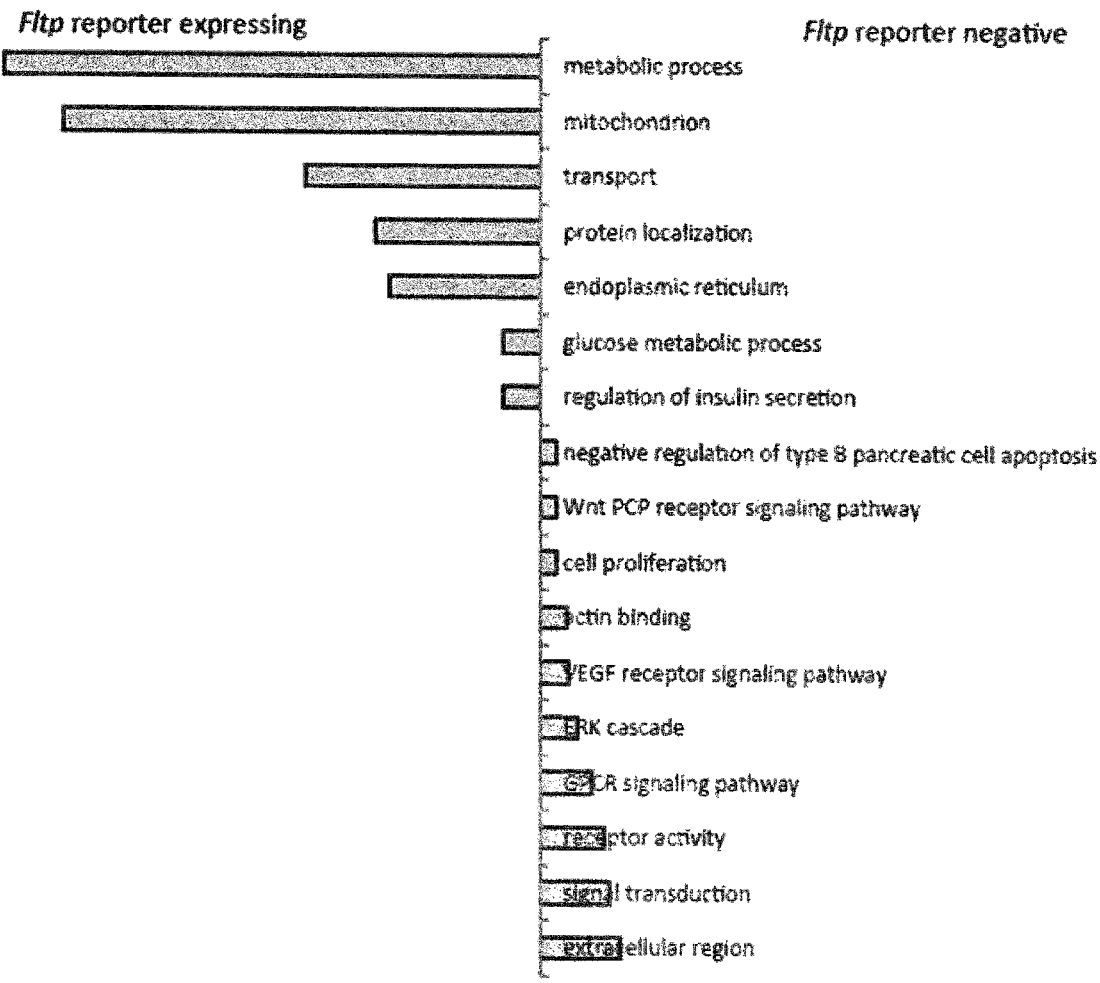

FIG. 6: Fltp reporter negative and positive islet subpopulations show distinct gene expression differences.

(A) Schematic overview of experimental approach starting from islet isolation to Fluorescent activated cell sorting (FACS) to gene expression analysis using microarray. (B) FACS plot of endocrine subpopulations with side scatter (SSC) on y-axis and emission of 488 nm fluorescence on x-axis from isolated mouse islets of Fltp$^{ZV/+}$ mouse (12 weeks old). (C) Representative images of single immunofluorescence stainings of Nkx6.1 and Fltp reporter on sorted Fltp reporter negative cells and Fltp reporter expressing cells. (D) Microarray analysis of Fltp mRNA expression in FACS sorted samples; two dimensional heat map of microarray transcriptional gene profile containing genes which are differential regulated and important in endocrine cell function, polarity, signaling and cell cycle; P<0.05 and 1.5× regulated, 3 samples left are Fltp reporter expressing samples and 2 samples right are Fltp reporter negative samples. (E) GO-term enrichments after analysis with Geps of Genomatix®; bars represent significance by P-value. Nuclear reporter of Ftp expression (Fltp) is marked by GFP antibody (C).

Figure 7:
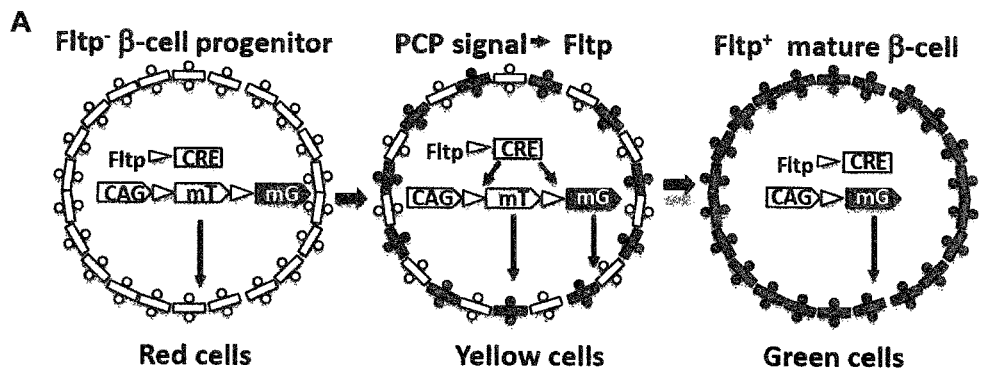
Figure 7:
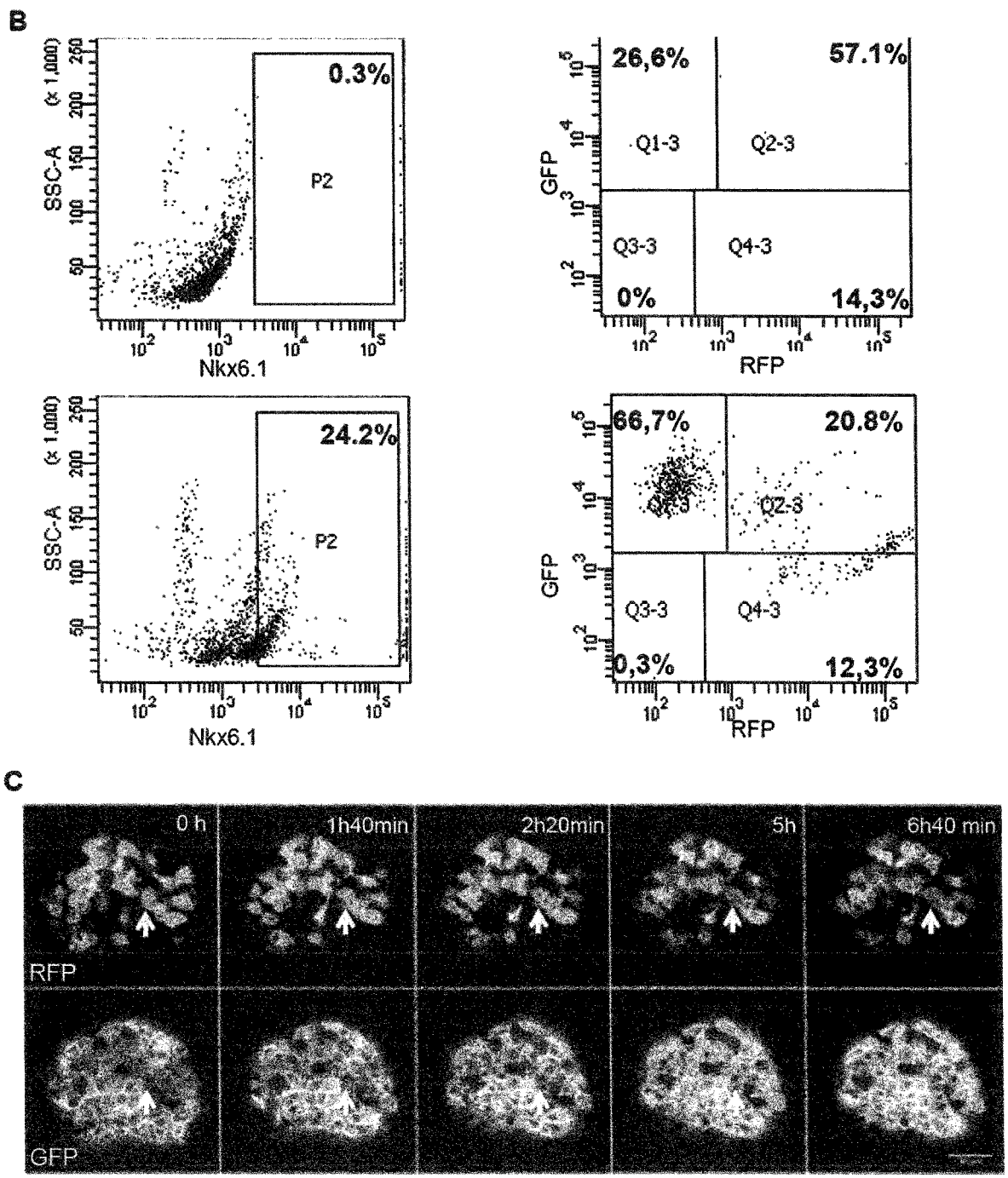

FIG. 7: Genetic lineage tracing reveals that Fltp negative progenitors give rise to Fltp expressing mature β cells (A) Scheme of the Fltp$^{T2A-iCre/+}$-mTmG$^{+/-}$ model. In this model all cells express membrane bond tomato (mT) except for the Fltp$^{T2A-iCre}$ expressing cells which express membrane bound GFP (mG). When a Fltp negative cell starts to activate the Fltp promoter the cells switch through a yellow state (mG and mT expression) into the green state (mG expression). (B) Fluorescent activated cell sorting plot of islets from Fltp$^{T2A-iCre/+}$-mTmG$^{+/-}$ model. Nkx6.1 staining control (up) and Nkx6.1 stained cells (down). GFP and RFP expression are shown on the right (66.7% of Nkx6.1+ cell are GFP expressing cells, 12.3% are RFP positive and 20% are GPF and RFP positive). (C) Representative images from live imaging experiment of islet isolated from Fltp$^{T2A-iCre/+}$-mTmG$^{+/-}$ which shows the conversion of a mT expressing cell into mG and mT expressing state (white arrow).

Figure 8:
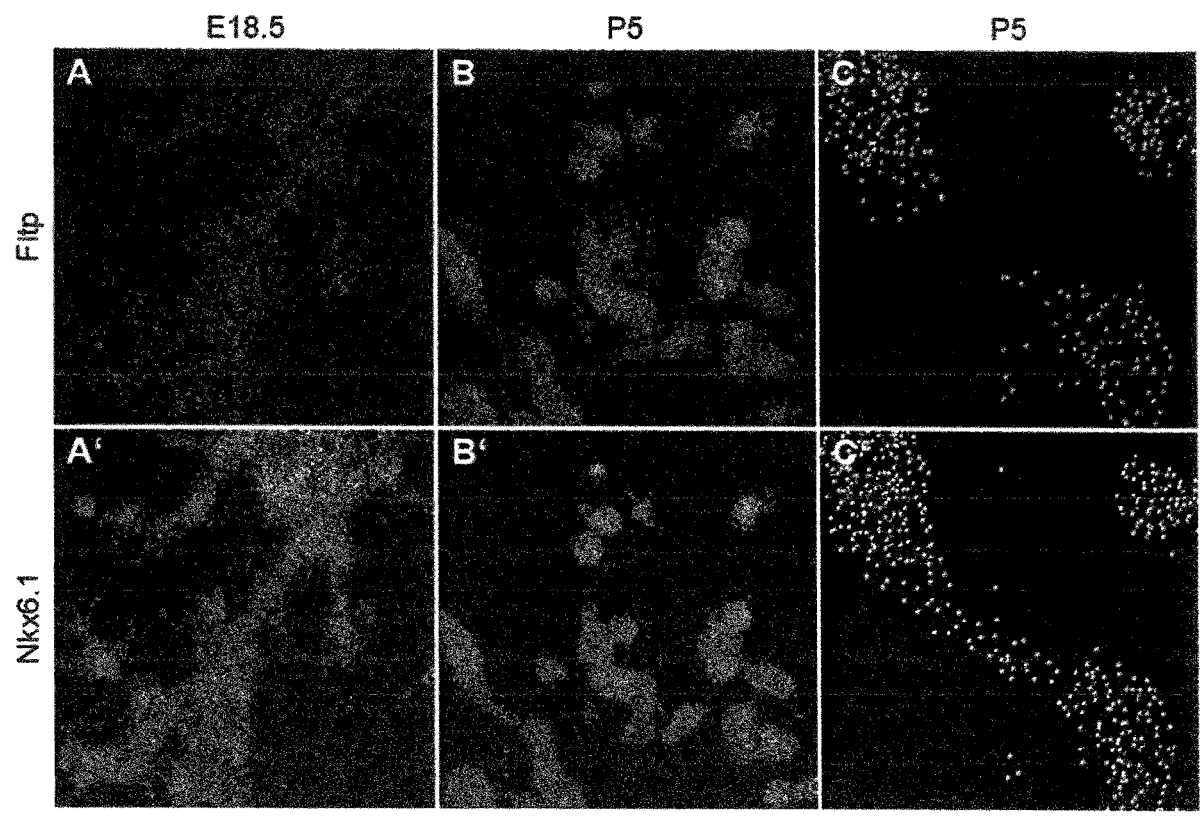

FIG. 8: Fltp expression correlates with islet neogenesis and post-natal β cell maturation.

(A-C') Qualitative analysis of Fltp::H2B-Venus reporter activity in whole-mount stained and BABB cleared pancreata and analyzed by LSM analysis at E18.5 and P5. Fltp reporter activity is detected by anti-GFP antibodies. High magnification images of compacted islets and cord-like structures (C-C'). Fltp reporter activity strongly increases while islets form and become compacted 3D structures, but is still undetectable in cord-like structures.

Figure 9:
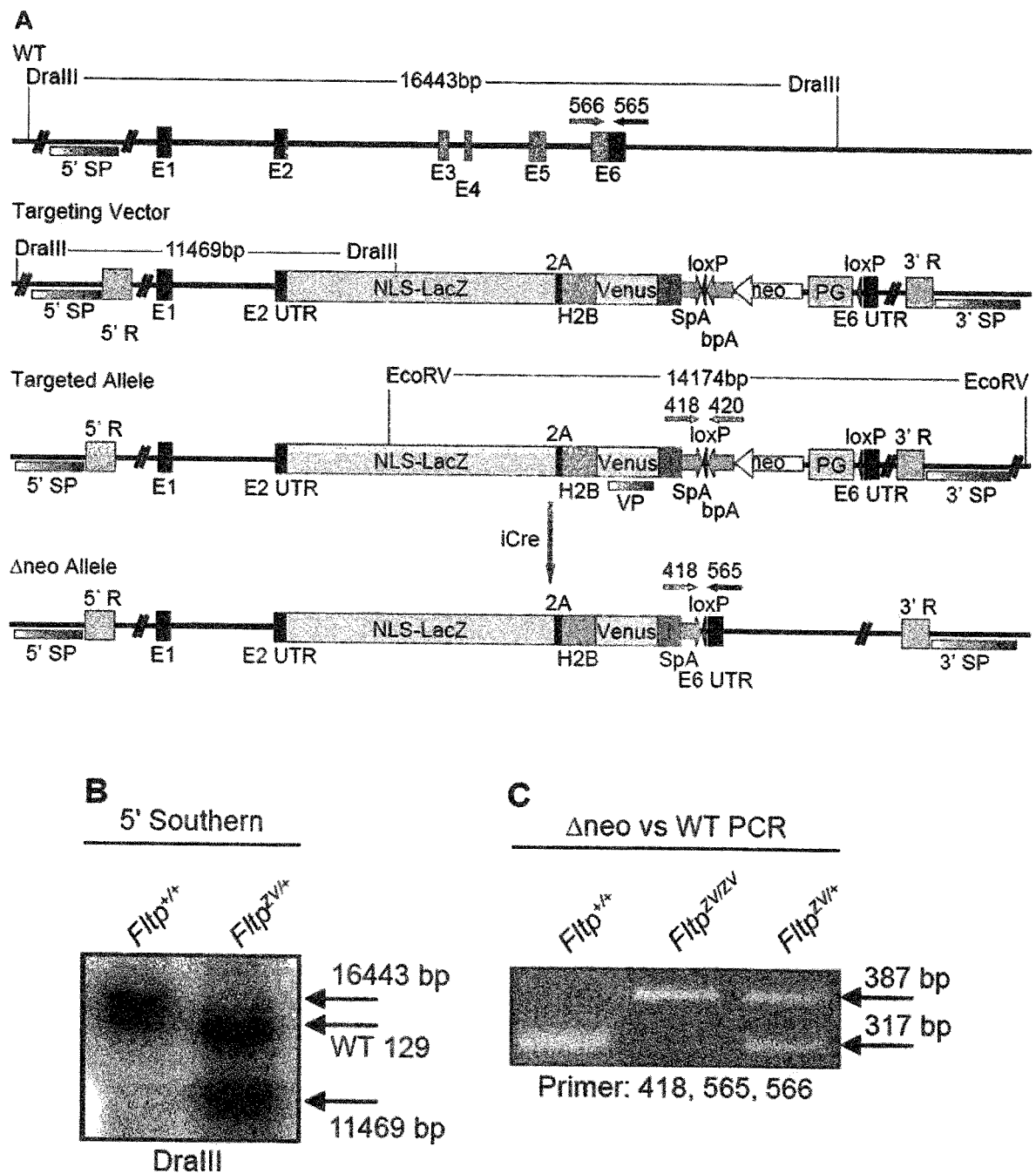
Figure 9:
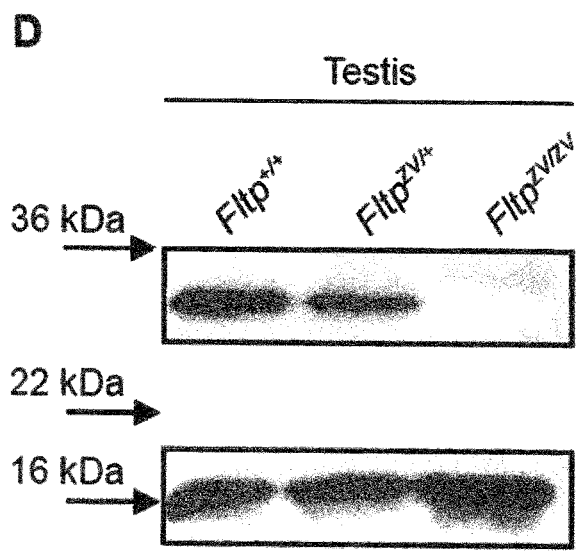

FIG. 9: Fltp$^{ZV/ZV}$ animals are Fltp null mutations.

(A) The Fltp$^{ZV}$ targeting strategy deletes the whole open reading frame ranging from exon 2 (E2) till E6 (Primers for genotyping: 5'-AGCCATACCACATTTGTAGAGG-3', 5'-CAGCATGGCATAGATCTGGAC-3', 5'-GAGGCTGACTGGGAACAATC-3'). The external 5'- as well as the 3'-Southern probe are indicated. Restriction enzyme sites for DraIII and EcoRV are shown. Homology regions for recombination of the targeting construct are indicated as 5'- and 3'-Retrieval (5'- and 3'-R). The figure is on scale. (B) Southern blot of WT embryonic stem (ES) cells versus Fltp$^{ZV/+}$ ES cells digested with DraII and hybridized with the external 5' Southern probe showing the BI6 (16443 bp) and 129 WT allele as well as the BI6 targeted allele (11469 bp). Notice the shift of the WT band due to restriction length polymorphism. (C) Genotyping PCR to discriminate between WT, Fltp$^{ZV/+}$, and Fltp$^{ZV/ZV}$ (Primers used: 418. 565, and 566; WT band (317 bp); targeted Δneo band (387 bp)). (D) Western blot shows the absence of Ftp protein in testis lysate of Fltp$^{ZV/ZV}$ animals. Fltp protein band is detectable at around 25 kDa (calculated weight 20 kDa). Abbreviations: NLS-LacZ: nuclear localization signal-beta-galactosidase; 2A: viral T2A sequence; H2B: histon-2B; Venus: yellow fluorescent reporter gene; SpA: Simian Virus 40 polyadenylation signal; loxP: site of Cre mediate recombination; bpA: bovine Growth Hormone polyadenylation signal; neo: neomycin resistance cassette; PG: phosphoglycerate kinase; UTR: untranslated region; SP: Southern probe; VP: Venus probe.

Figure 10:
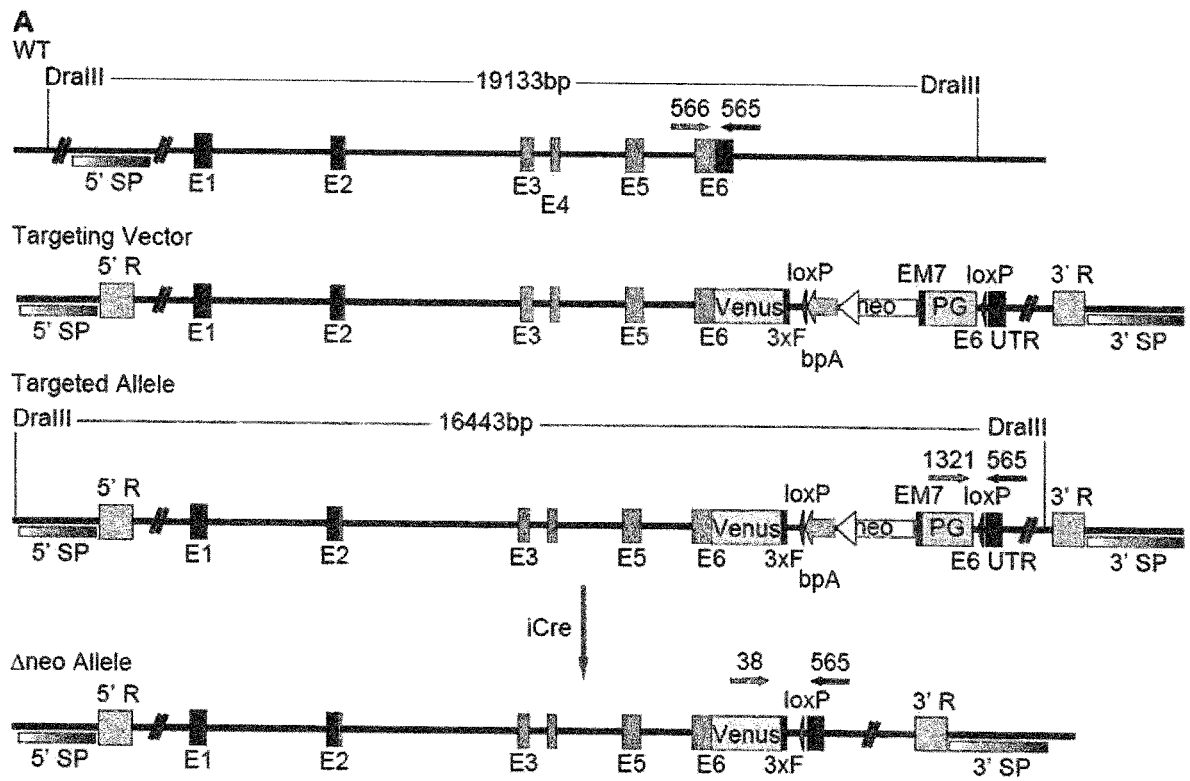
Figure 10:
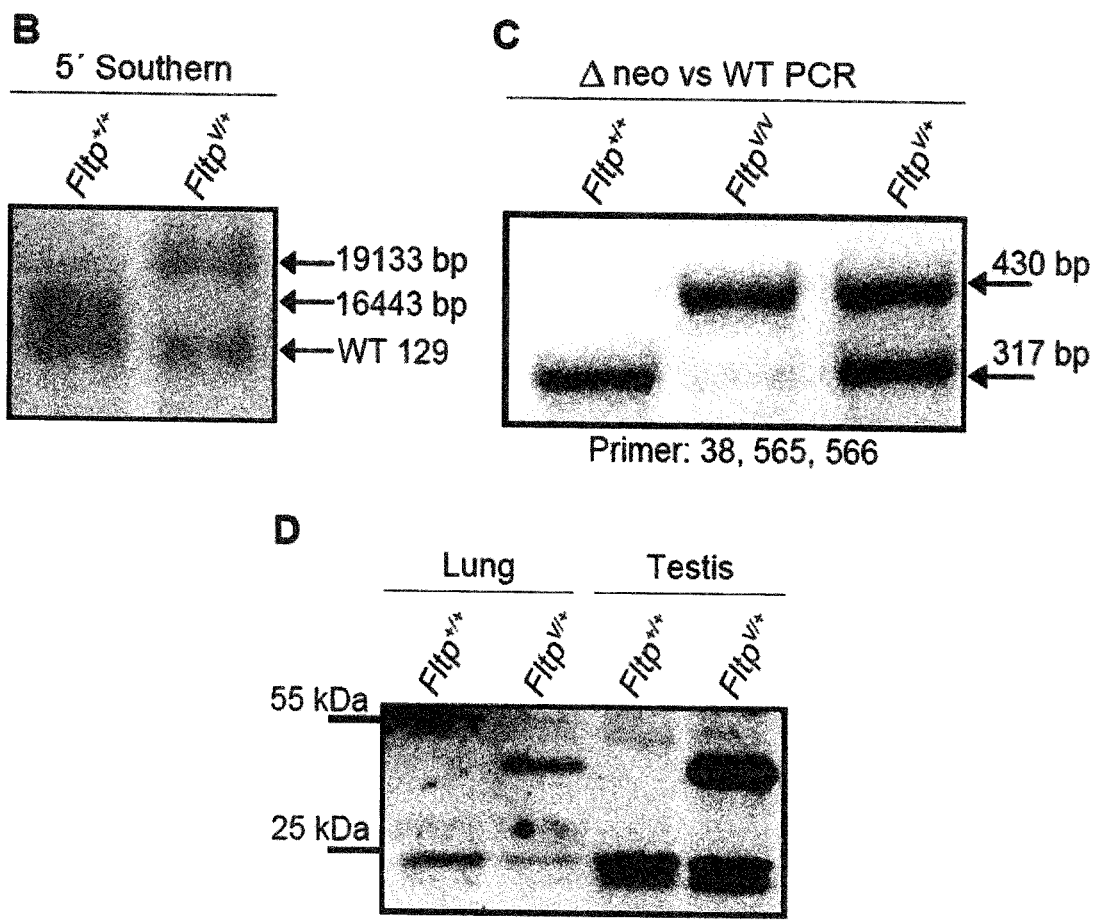

FIG. 10: Generation a validation of the Fltp::Venus Fusion mouse line.

(A) The Fltp::Venus-Fusion targeting strategy fuses the open reading frame of Fltp to the fluorescent reporter gene Venus and the 3×FLAG tag (Primers for genotyping: 5'-CAGCATGGCATAGATCTGGAC-3', 5'-GAGGCTGACTGGGAACAATC-3', 5'-CAAGATCCGCCACAACATCG-3'). The external 5'- as well as the 3'Southern-probe are indicated. Restriction enzyme sites for DraIII are shown. Homology regions for recombination of the targeting construct are indicated as 5'- and 3'-Retrieval (5'- and 3'-R). (B) Southern blot analysis of targeted mouse ES cells (129Sv-/-C57BI/6; IGD 3.2; Hitz et al., 2007). Genomic DNA was digested with DraIII and hybridized with the 5' Fltp external probe resulting in bands of 16443 bp (calculated size) for WT (Fltp$^{+/+}$) and 19133 bp for Fltp::Venus Neo (Fltp$^{V/+}$) allele. (C) Genotyping PCR to discriminate between WT, Fltp$^{V/+}$, and Fltp$^{V/V}$ (Primers for genotyping: 5'-CAGCATGGCATAGATCTGGAC-3', 5'-GAGGCTGACTGGGAACAATC-3', 5'-CAAGATCCGCCACAACATCG-3). WT band (317 bp); targeted Δneo band (430 bp)). (D) Western blot analysis of lung and testis lysates of 2 months old male WTor Fltp$^{V/+}$ animals using anti-Fltp antibody to detect endogenous Fltp (24 kDa) as well as the Fltp::Venus fusion protein (50 kDa). Abbreviations: E1-6: exon 1-6; Venus: yellow fluorescent reporter gene; bpA: bovine Growth Hormone polyadenylation signal; EM7: bacterial promoter; loxP: site of Cre mediate recombination; neo: neomycin resistance cassette; PG: phospho-glycerate kinase; UTR: untranslated region; SP: Southern probe; VP: Venus probe; 3×F: 3×FLAG tag.

Figure 11:
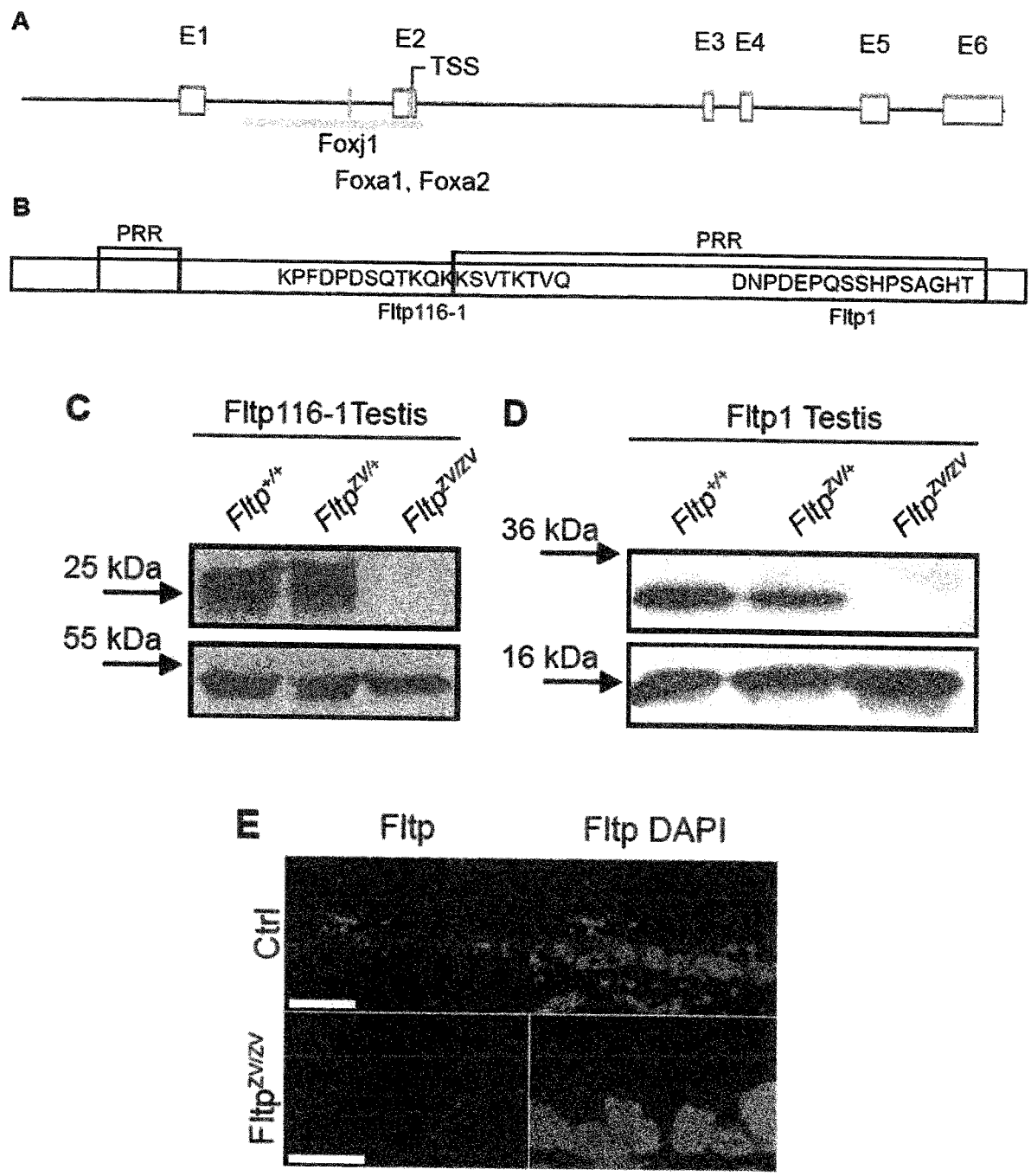

FIG. 11: Fltp with active Foxa2 binding sites in its promoter, antibody binding sites and its conservation among species.

(A) Fltp shows Foxj1, Foxa1, and Foxa2 binding sites in its promoter (bar under the schematic gene). (B) Scheme of Ftp protein showing the two predicted proline rich repeats (PRRs) and the peptide sequences of the Ftp116-1 antibody as well as the Ftp1 antibody. (C, D) Western blot showing the specificity of the Fltp116-1 (C) as well as the Fltp1 (D) antibody in testis lysate of WT, Fltp$^{ZV/+}$, and Fltp$^{ZV/ZV}$ animals. Fltp protein band is detectable at around 25 kDa (calculated weight 20 kDa). (E) Immunohistochemistry on cryosections combined with LSM analysis to show that the Fltp116-1 antibody is specific. Ftp is localized at the apical plasma membrane and along cilia in multi-ciliated lung epithelial cells of WT (Ctrt) adult animals, but no Fltp immunoreactivity is detected in Fltp$^{ZV/ZV}$ lungs. Abbreviations: exon1-6 (E1-E6); TSS: transcriptional start site). Nuclei are marked by 4',6-Diamidin-2-phenylindol (DAPI), Fltp by Fltp116-1. Scale bars; 10 μm.

Figure 12:
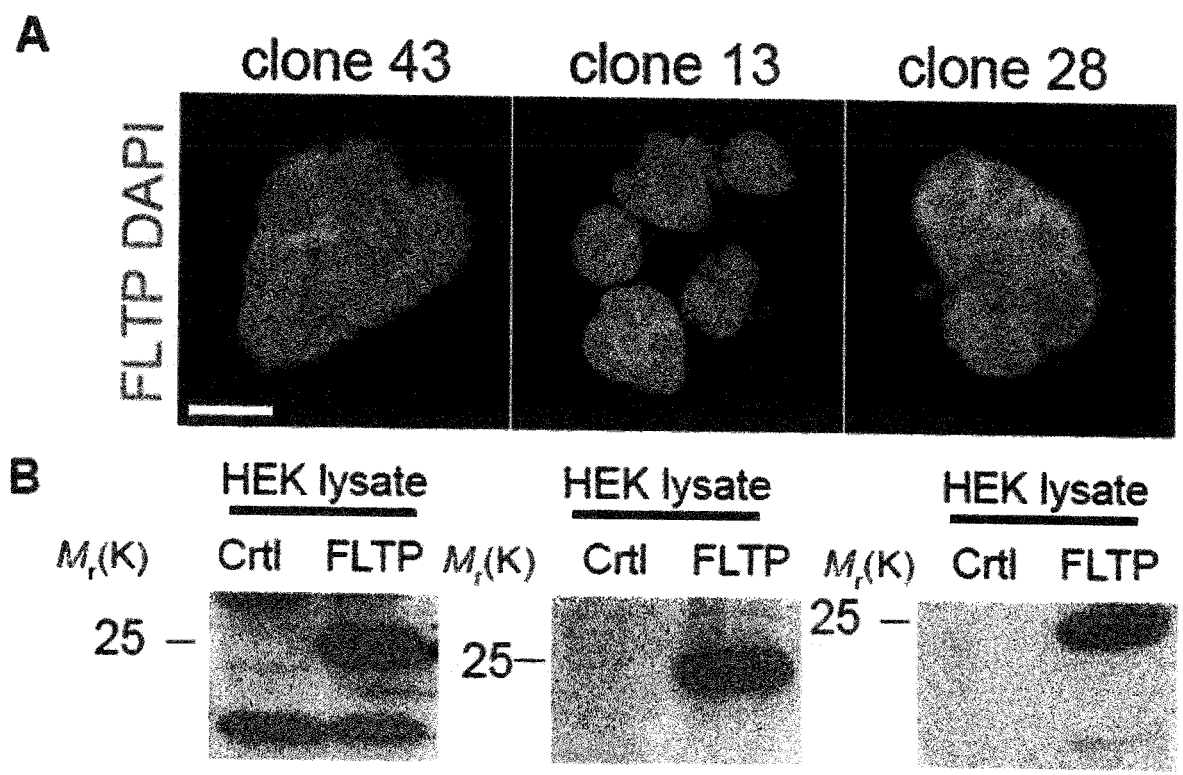

FIG. 12: monoclonal antibodies against human FLTP (A) Laser scanning microscopy (LSM) of EndoC-β H1 human β-cells stained with different monoclonal antibodies (clones #13, #28 and #43) against human FLTP. As negative control human embryonic stem cells (hESCs) were used (not shown). (B) Western Blot of Strep Flag-tagged human FLTP transiently transfected in HEK293T and detected by monoclonal antibodies (clones #13, #28 and #43). Non-transfected HEK293T cells lysate were used as negative control.

Figure 13:
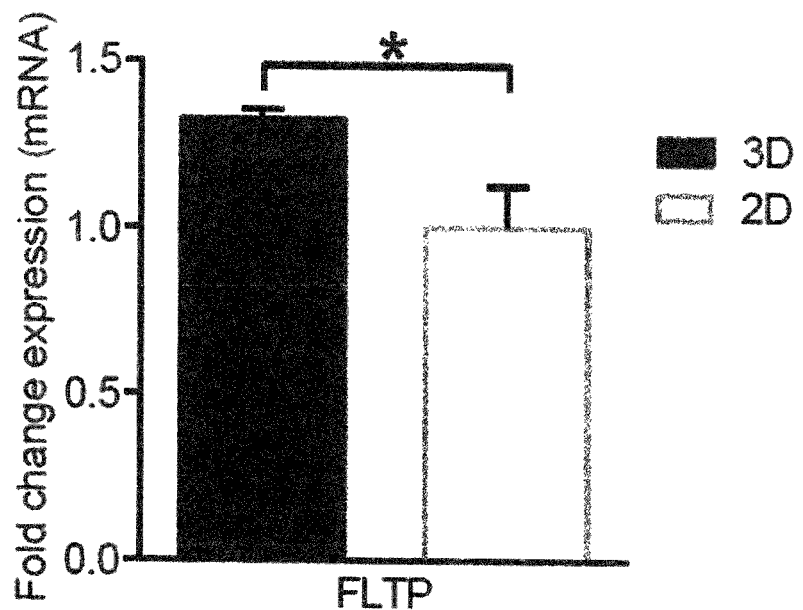

FIG. 13: FLTP mRNA expression in EndoC-β H1 human β-cells

Significant increase of human FLTP mRNA expression levels cultured under 3D vs 2D conditions in EndoC-β H1 cells is shown.

Figure 14:
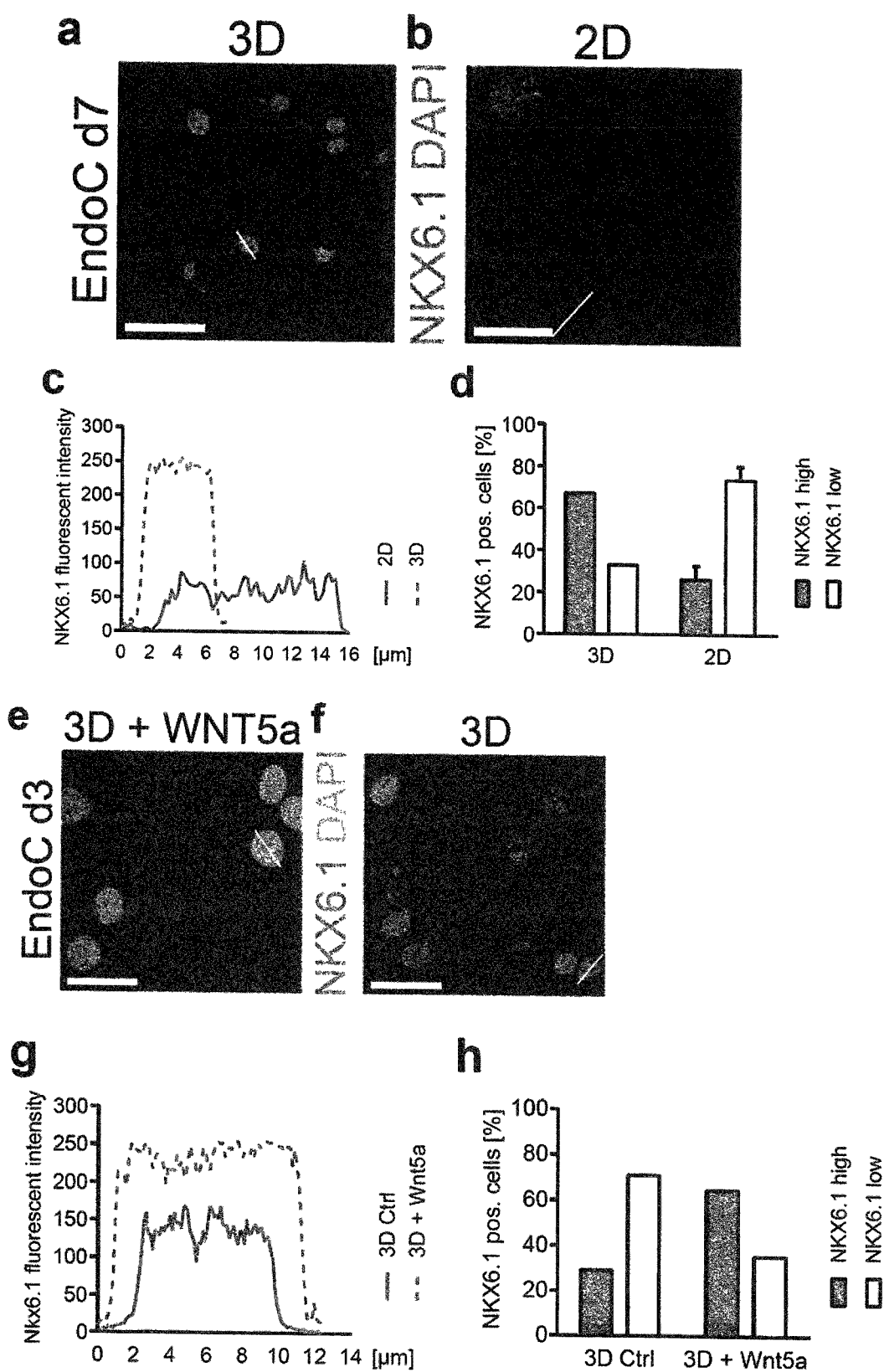
Figure 14:
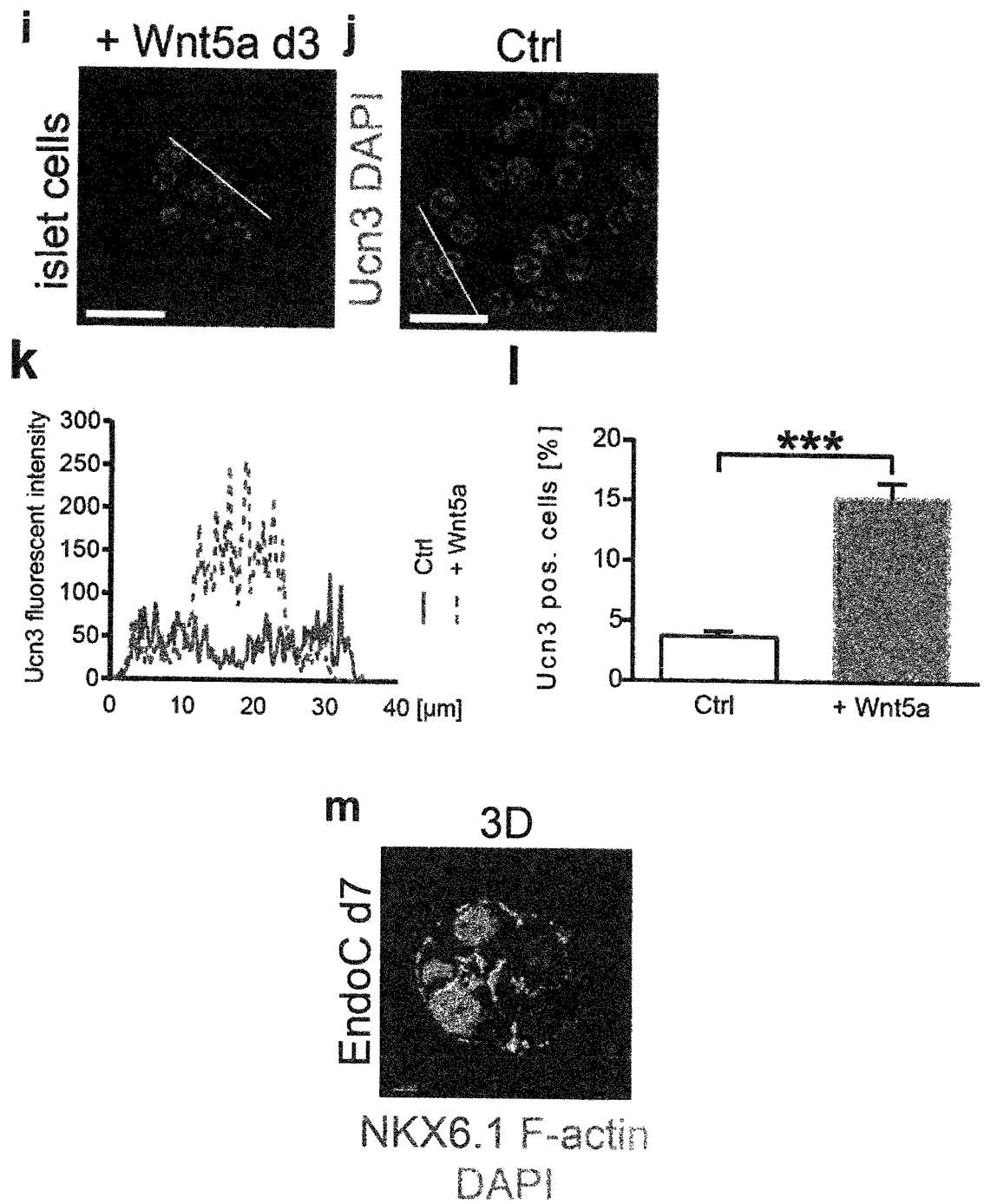

FIG. 14: 3D polarization and Wnt/PCP pathway activation in murine and human β-cells (a,b) Laser scanning microscopy (LSM) of EndoC-β H1 human β-cells cultured in Matrigel (3D) show higher expression of β-cell and maturation marker NKX6.1 compare to 2D conditions (b). For quantification see d (3D: n=2; 2D: n=2). (c.g) Diagram showing the fluorescent intensity of Nkx6.1 in one single cell in 3D compared to 2D (c) and in 3D treated with Wnt5a and 3D without Wnt5a treatment (g). White lines indicate the measured region of interest (ROI) (i.e. in a,b for c; e, f for g). (e,f) LSM of EndoC-β H1 cells cultured Matrigel (3D) and treated with WNT5a show higher expression of NKX6.1 than under 3D conditions (f). For quantification see h (WNT: n=1; control: n=4). (i,j) LSM of isolated islets of P5 WT animals either treated with (i) or without (j) Wnt5a for 3 days showing significant increase in Ucn3 maturation marker staining. For quantification see I (Wnt5a treated: n=3; untreated: n=3). (k) Diagram showing the fluorescent intensity of Ucn3 of the re-aggregated islets+Wnt5a and without Wnt5a treatment. White lines in (i,j) indicate the measured ROI. (m) LSM picture of EndoC-β H1 cells at day 7 showing compacted 3D pseudo-islets. (n) FLTP mRNA expression level in EndoC-βH1 cells cultured under 3D and 2D conditions. Counting criteria for d,h are: The NKX6.1 fluorescent intensity of a certain number of cells of several independent experiments were counted in 2D and 3D and the median fluorescent intensity was calculated with IMARIS. The median fluorescent intensity was used as a threshold. All cells with higher intensity were counted as NKX6.1 high, all cells with lower intensity were counted as NKX6.1 low cells. For FIG. 14d (3D: 300 NKX6.1+ cells; 2D: 221 Nkx6.1*cells) were counted. For FIG. 14h (WNT: 110 Nkx6.1+ cells; control: 550 Nkx6.1+ cells) were counted. Scale bars, 20 μm (a,b,e,f), 10 μm (m).

Figure 15:
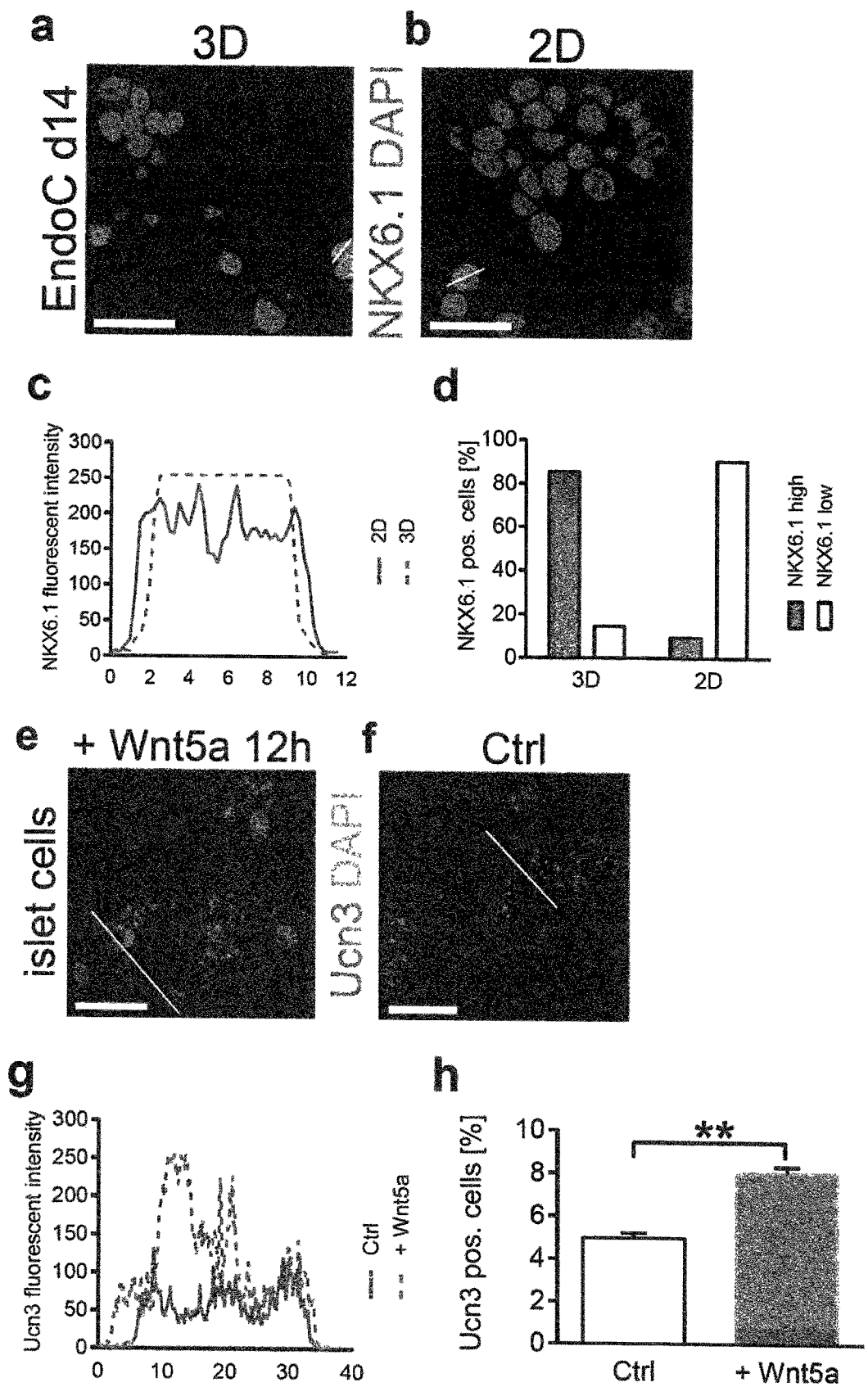

FIG. 15: 3D polarization and Wnt/PCP pathway activation in murine and human β-cells (additional data)

(a,b) LSM of EndoC-β H1 cells cultured in Matrigel (3D) show higher expression of β-cell and maturation marker NKX6.1 than under 2D (b). For quantification see d (3D: n=1; 2D: n=1). (c,) Diagram showing the fluorescent intensity of Nkx6.1 in one single cell in 3D and in 2D. White lines in a,b show the measured region of interest (ROI). (e,f) LSM of isolated islets of P5 WT animals revealed a higher amount of maturation marker Ucn3 protein in islets treated with Wnt5a for 12 h (e) compared to non-treated islets (f). For quantification see h (islets+Wnt5a: n=3; untreated islets: n=3). (g) Diagram showing the fluorescent intensity of Ucn3 of the re-aggregated islets+Wnt5a and without Wnt5a. White lines in (e,f) indicate the measured ROI. Counting criteria of c are: The NKX6.1 fluorescent intensity of a certain number of cells of several independent experiments were counted in 2D and 3D and the median fluorescent intensity was calculated with IMARIS. The median fluorescent intensity was used as a threshold. All cells with higher intensity were counted as NKX6.1 high, all cells with lower intensity were counted as NKX6.1 low cells. For FIG. 15d (3D: 571 NKX6.1+ cells; 2D: 265 Nkx6.1+ cells) were counted. For FIG. 15h (islets+Wnt5a: 680 cells; untreated islets: 877 cells) were counted. Scale bars, 20 μm (a,b,e,f).

The examples illustrate the invention:

EXAMPLE 1: MATERIALS AND METHODS

Animal Studies

Mice were kept in the animal facility under optimal conditions in a 12-h light cycle. Food and water were given ad libitum. Animal experiments were carried out according to the German animal care and ethics legislation and were approved by the local government authorities.

Eight-week-old Fltp$^{ZV/+}$ females were paired to C57BL/6J males and separated from the males after the appearance of the vaginal plug indicating day 0 of pregnancy. Pregnant females were euthanized on day 15.5 of pregnancy (E 15.5) and the pancreas removed.

Glucose tolerance test (GTT) and insulin secretion test (IST) were carried out in 12 weeks-old mice after a 12 h fast. Briefly, a single dose of glucose was intraperitoneally administrated (2 g/kg body weight) to the mice and blood glucose level was measured using Freestyle Lite glucometer (Abbot Laboratory, USA), at 0, 15, 30, 60 and 120 minutes following glucose loading, by cutting off the tip of tail and squeezing it gently. For plasma insulin detection, blood sample were taken at 0, 2.5, 5, 10 and 20 minutes following glucose loading (Andrikopoulos, Blair et al. 2008, Ayala, Samuel et al. 2010). Plasma insulin was determined by using Ultra-sensitive mouse insulin ELISA kit (Chrystal Chem, USA) according to the manufacturer's instructions.

For Streptozotocin (STZ)-mediated diabetes induction, freshly prepared STZ (Sigma Aldrich, Germany) in 50 nM sodium citrate (pH 4.5) was injected intraperitoneally (40 mg/kg) daily for 5 days. Blood glucose level was measured every 2 days using Freestyle Lite glucometer (Abbot Laboratory). On day 16 after the first STZ injection, GTT was carried out as described and mice were euthanized.

Generation of Animal Models

A Flattop-Venus fusion protein was generated by homologous recombination in mouse embryonic stem (ES) cells by removing the translational stop codon in exon 6 and directly fusing the Venus fluorescent protein to the open-reading frame of Flattop. From these ES cells a knock-in mouse was generated by germ line transmission of the targeted ES cells. These mice express the Flattop-Venus fusion protein in all tissues where Flattop is expressed in equal amounts to the wild-type Flattop protein. This Flattop-Venus fusion reporter has the advantage that it is expressed in physiological amount, shows normal protein turnover and shows normal subcellular localization.

Antibody Generation

To be able to analyse the Fltp protein in more detail, two different polyclonal rabbit antibodies were raised against a central and C-terminal epitope (FIG. 11). The specificity of these antibodies was confirmed in western blot analysis and immunocytochemistry on lysates and cells in which the Flip gene was either over-expressed or knocked-out (FIG. 11). To be able to analyse the human FLTP protein in more detail, three different monoclonal rat antibodies were raised against a central and C-terminal epitope (FIG. 12). The specificity of these antibodies was confirmed in western blot analysis and immunocytochemistry on lysates and cells in which the Strep-Flag tagged human FLTP cDNA was over-expressed (FIG. 12). These antibodies can be used as primary antibodies to detect the protein in tissues or cell cultures and using secondary antibodies either conjugated to horseradish peroxidase, alkaline phosphatase or fluorescent dyes.

Total Pancreatic Insulin Content

After 12 h starving, the animals were euthanized and the pancreas rapidly removed. Pancreas was placed into 5 ml 0.2 M HCl in 70% Ethanol, homogenized and incubated over night at −20° C. Subsequently, the homogenized pancreas was again mixed with 0.2 M HCl in 70% Ethanol and incubated over night at −20° C. After centrifugation at 1000 g for 15 minutes the supernatant was diluted (1:2) with 1 M Tris pH 7.5 and then analyzed. Insulin detection was performed by using Ultra sensitive mouse insulin ELISA kit (Chrystal Chem, USA) according to the manufacturer's instructions. Total pancreatic protein content was estimated by Bradford assay (Harlow and Lane 2006). Total pancreatic insulin content is stated as insulin (ng)/total pancreatic protein (µg).

LacZ Staining and Immunohistochemistry

Whole mount organ staining was performed as previously described (Huber, Kania et al. 2005). For whole mount imaging, embryos were cleared using BABB (1 part benzyl alcohol, 2 parts benzyl benzoate). For immunohistochemistry staining, pancreas samples were fixed in 4% formalin, cryoprotected by incubation in sucrose gradient for 1 h each (5%, 15%, 30%) and embedded in Optimum Cutting Temperature (OCT). Cells sorted on glass slide were fixed with 2% PFA Nuclear staining was performed with DAPI (Life Technology, Germany). For histological assessment of islet β-cell proliferation, mice were injected with EdU Solution (100 µg/g of body weight) 24 h prior to being sacrificed. EdU staining was performed using the Click-iT® Staining Kit (Life Technology) according to the manufacturer's instructions. Cryosection imaging was performed using Leica Confocal SP5 microscope. For quantification purposes, stained cells were counted manually on every tenth section (14-15 m thick frozen section). Quantification of whole mount organ staining was performed by using IMARIS software (Bitplane, Switzerland).

Islet Isolation, FACS Analysis and Gene Profiling

Islet isolation was carried out by collagenase P (Roche, Germany) digestion and centrifugation using Optiprep density gradient (Sigma). Isolated islets were handpicked two times under the microscope. After 1 to 3 h of culture, islets were washed with PBS and incubate with 0.25% Trypsin-EDTA (Invitrogen) to obtain single cell suspensions. Single cells were sorted using FACS-Aria III (BD Bioscience). The results were analyzed by using Flow Jo software. Total RNA was extracted using miRNeasy micro kit (Qiagen, Germany), amplified with the Ovation PicoSL WTA System V2 in combination with the Encore Biotin Module (Nugen, USA). Amplified cDNA was hybridized on Affymetrix Mouse Gene ST 1.0 arrays containing about 28,000 probe sets. Staining (Fluidics script FS450_0007) and scanning was done according to the Affymetrix expression protocol including minor modifications as suggested in the Encore Biotion protocol. Expression console (v.1.3.0.187, Affymetrix) was used for quality control and to obtain annotated normalized RNA gene-level data (standard settings including median polish and sketch-quantile normalization). Statistical analyses were performed by utilizing the statistical programming environment R (R Development Core Team) implemented in CARMAweb. Genewise testing for differential expression was done employing the (paired) limma t-test and Benjamini-Hochberg multiple testing correction (FDR<10%). Heatmaps were generated with CARMAweb and cluster dendrograms with the R script hclust. GO term and pathway enrichments were done for 1.5× regulated genes and a P-value<0.005 using the GePS module in the Genomatix Software Suite v3.1 (Genomatix, Munich, Germany).

For lineage tracing studies, islet from eight-week-old Fltp$^{T2A-iCre}$-mTmG were isolated as described above. For FACS analysis islet were incubate with 0.25% Trypsin-EDTA (Invitrogen) to obtain single cell suspensions and intarcellular staining for Nkx6.1 was performed. For live imaging experiment isolated islets from Fltp$^{T2A-iCre}$-mTmG were cultured in matrigel and imaging was performed using Leica Confocal SP5 microscope.

Antibodies

Primary antibodies used for immunofluorescence: Goat anti-Nkx6.1 (R&D system, Germany, AF5857 1:200): chicken anti-GFP (Aves Labs, USA. GFP-1020 1:800): guinea pig anti-glucagon (Millipore, 4031-01F, 1:500); goat anti-somatostatin (Santa Cruz, USA, sc-7819, 1:300); rabbit anti-insulin (Thermo Scientific, USA, PA-18001, 1:300); guinea pig anti-insulin (Thermo Scientific, USA, PA-26938, 1:300); goat anti-Pancreatic Polypeptide (PP) (Abcam, USA, ab77192, 1:300); rabbit anti-Ki-67 (Abcam, ab15580, 1:200); rabbit anti-Urocortin 3 (Phoenix Pharmaceuticals. USA, H-019-29, 1:300); Alexa Fluor 546 phalloidin (Invitrogen,Germany, A22283, 1:200).

Secondary antibodies used for indirect fluorescence staining (dilution1:800 for all): Goat anti-chicken Alexa Fluor 488 (Dianova, Canada, 103-545-155); donkey anti-goat Alexa Fluor 488 (Invitrogen, Germany, A11055); donkey anti-mouse Alexa Fluor 555 (Invitrogen, A31570); donkey anti-goat Alexa Fluor 555 (Invitrogen, A21432); donkey anti-rabbit Alexa Fluor 555 (Invitrogen, A31572); donkey anti-goat Alexa Fluor 594 (Invitrogen, A11058); donkey anti-mouse Alexa Fluor 594 (Invitrogen, A21203); donkey anti-guinea-pig Alexa Fluor 649 (Dianova, 706-495-148). Nuclear staining was performed with DAPI (Life Technology, Germany). EdU staining was performed using the Click-iT® Staining Kit (Life Technology) according to the manufacturer's instructions.

Statistical Analysis

Statistical analysis was performed using GraphPad Prism 6 Software (GraphPad Software, USA). Student's t-test was used for direct comparisons between two groups. A p value of <0.05 was considered as statistically significant. Data is expressed as means±SEM/SD.

EXAMPLE 2: THE EXPRESSION OF THE PLANAR CELL POLARITY (PCP) EFFECTOR GENE FLTP STRONGLY INCREASES DURING POST-NATAL β CELL MATURATION AND SHOWS HETEROGENEOUS LEVELS IN ADULT ENDOCRINE CELLS

Three-dimensional (3D) and self-organized tissue architecture is required for organ formation and function (Eiraku, Takata et al. 2011, Sasai 2013). To determine whether the acquisition of tissue polarity during islet neogenesis impacts on β cell function and maturation, tissue polarity establishment was analyzed on the molecular level by using the Fltp::H2B-Venus reporter mice. The Fltp reporter activity accurately reflects planar cell polarity (PCP) activity in the inner ear and lung, tissues that depend on Fltp function as a modulator of the actin and MT cytoskeleton dynamics. Fltp reporter activity was first analyzed at embryonic day (E) 18.5 when β cells are still organized in cord-like structures and vividly aggregate to form 3D sphere-like mini-organs. For this purpose, whole pancreata were isolated, the tissue was cleared and laser-scanning confocal microscopy (LSM) analysis was used to acquire the entire 3D tissue distribution of Nkx6.1$^+$ β cells (FIG. 8). Interestingly, Fltp reporter expression was confined to β cells that were found in compacted islets, but was not detectable in β cells that were still organized in cord-like structures. Additionally, it seemed that high levels of Nkx6.1 also induced Fltp reporter activity, but only in already formed islet structures. Together these results confirmed that Ftp reporter activity is switched on during planar cell polarity acquisition comparable to the inner ear and the lung.

To further investigate the expression of this PCP effector gene during post-natal β cell maturation (Blum, Hrvatin et al. 2012), Fltp::H2B-Venus reporter expression was analyzed in pancreatic sections shortly after birth (FIG. 1A). At postnatal day 1 (P1), Fltp reporter activity was detected in less than 50% of Nkx6.1$^+$ β cells. Reporter activity rapidly increased in up to 70% of β cells while they matured in newly formed islets during the first ten days of life. In adult mice, Fltp reporter activity was detected in approximately 80% of β cells and around 50% of other endocrine cell populations (FIG. 1C). These results show that all endocrine cells express heterogeneous levels of PCP reporter activity. Additionally, the reporter activation during islet neogenesis and compaction likely reflects the changes in physical properties of the islet cell niche and might have a functional impact on all islet cells.

EXAMPLE 3: FLTP NEGATIVE β CELLS SHOW INCREASED PROLIFERATIVE CAPACITY ESPECIALLY DURING β CELL EXPANSION PERIODS

For the further study, the focus was on the biological relevance of the PCP-related heterogeneity for β cells. Therefore, first the proliferation rate of Fltp reporter negative and Fltp reporter expressing β cells during homeostasis, as well as during pregnancy-induced and postnatal β cell expansion periods was compared. Strikingly, the Fltp reporter negative Nkx6.1$^+$ cells at P1, P3 and P11 showed an up to four-fold higher replication rate when compared to Fltp reporter expressing Nkx6.1$^+$ β cells, as measured by Ki67 immunoreactivity in pancreatic cryosections (FIG. 2E). A similar up to 4-fold difference in the proliferation rate of these two β cell subpopulations was observed during pregnancy (FIGS. 2A and 2E). The concomitant and significant decrease of Fltp reporter positive cells from 80% to 70% (FIG. 2F) indicates that mainly the Fltp reporter negative cells proliferate and contributed to β cell expansion during pregnancy. Even in adult mice fed ad libitum, a physiological state where β cells are in homeostasis and refractory to proliferation, Fltp reporter negative β cells still showed an increased replication capacity (FIG. 2C). These proliferation studies were confirmed by EdU-pulse labeling during β cell homeostasis and expansion (FIG. 2C). Thus collectively these data illustrate that the two subpopulations of β cells show markedly different proliferative capacity depending on environmental conditions and cell polarity status.

EXAMPLE 4: LOSS OF MOUSE FLTP AND AN INTRONIC SNP IN HUMAN FLTP ASSOCIATES WITH INSULIN SECRETION DEFECTS

It is well established that β cells are functionally coupled and that insulin secretion depends on the actin and MT cytoskeleton (Kalwat and Thurmond 2013). To analyze if the PCP effector protein Fltp is necessary for adult β cell function, a glucose tolerance test was performed using intra-peritoneal glucose stimulation (ipGTT) in adult males on a chow diet (FIG. 3A). Only a slight but not significant delay in glucose clearance was observed in Fltp$^{ZV/ZV}$ and Fltp$^{ZV/+}$ mice, when compared to Fltp$^{+/+}$ littermates. Also, no significant difference in total pancreatic insulin content was observed between Fltp$^{+/+}$, Fltp$^{ZV/+}$ and Fltp$^{ZV/ZV}$ mice (FIG. 3B). Interestingly, 1$^{st}$ (FIG. 3C), but not 2$^{nd}$ phase insulin secretion (FIG. 3D) seems to be delayed in homozygous mutants when compared to Fltp$^{+/+}$ littermates, suggesting that the PCP activity and Fltp function is necessary for glucose-induced insulin secretion of β cells.

To seek first evidence whether the human orthologue gene C1Orf192 is also associated with metabolic traits and 10+SNPs were screened for genetic association in a cohort of 2100 human pre-diabetic and diabetic subjects. Interestingly, this revealed that the intronic SNP rs75715534 with a minor allele frequency of 0.2 significantly associated with increased insulin secretion on lean subjects (BMI<25), whereas the same SNP associated with decreased insulin secretion in obese subjects (BMI>35) (FIGS. 4A and B). These results suggest that human FLTP differentially reacts to metabolic demand and is generally important for glucose-induced insulin secretion. Together these data suggest that Fltp-dependent cytoskeletal rearrangements established during planar cell polarity are important for glucose-induced insulin secretion of β cells.

Association Analysis

Subjects.

The study population consisted of 2,228 Caucasians at risk for type 2 diabetes (family history of type 2 diabetes, body mass index (BMI)>27 kg/m$^2$, impaired fasting glycaemia, and/or previous gestational diabetes) recruited from the ongoing Tubingen Family study for type 2 diabetes (1). All participants underwent assessment of medical history, smoking status, and alcohol consumption habits; the subjects furthermore agreed to undergo physical examination, routine blood tests, and oral glucose tolerance tests (OGTTs). Only individuals with complete phenotypic and genotypic data sets and documented absence of medication known to influence glucose tolerance, insulin sensitivity, or insulin secretion were included. All study participants gave informed written consent to the study which adhered to the Declaration of Helsinki.

The study protocol was approved by the OGTT and laboratory measurements. A standardized 75-g OGTT was performed following a 10-hovernight fast. For the determination of plasma glucose, insulin, and C-peptide levels, venous blood samples were drawn at baseline and at timepoints 30, 60, 90, and 120 min of the OGTT (Stefan, Machicao et al. 2005). Plasma glucose levels (in mmol/L) were measured with a bedside glucose analyser (glucose oxidase method, Yellow Springs Instruments, Yellow Springs, Ohio, USA). Plasma insulin and C-peptide levels (in pmol/L both) were determined by commercial chemiluminescence assays for ADVIA Centaur (Siemens Medical Solutions, Fernwald, Germany). BMI was calculated as weight divided by squared height (in kg/m$^2$). OGTT-derived insulin sensitivity was estimated as proposed earlier (Matsuda and DeFronzo 1999): 10,000/[c(Glc0)*c(Ins0)*c(Glc-mean)*c(Insmean)]½ (with c=concentration. Glc=glucose, and Ins=insulin). OGTT-derived insulin secretion was estimated as area under the curve (AUC) Cpep0-30/AUC Glc0-30 according to the formula: [c(Cpep0)+c(Cpep30)]/[c(Glc0)+c(Glc30)] (with Cpep=C-peptide). Ethics Committee of the Eberhard Karls University Tubingen.

Selection of Tagging SNPs and Genotyping.

Based on publicly available data from the 1000 Genomes Project (http://browser.1000 genomes.org/index.html), we analysed in silico a genomic area on human chromosome 1q23.3 spanning the C1orf192 gene (3.143 kb, five exons, four introns, located on the reverse strand) and 2 kb of the gene's 5'-flanking region. Within the analysed C1orf192 locus, 36 SNPs were found. Using the tagger analysis tool of Haploview (see the Wordl Wide Web at broadinstitute.org/ scientific-community/science/programs/medical-and-population-genetics/haploview/haploview), seven tagging SNPs were identified that cover all the other common SNPs (minor allele frequency≥0.01) with an $r^2$≥0.8. These SNPs were rs17399583 (C/T), rs11584714 (C/G), and rs57835711 (C/G) in the 5'-flanking region, rs114482063 (A/T) and rs182840301 (C/A) in intron 1, and rs16832872 (G/A) and rs75715534 (C/G) in intron 3. For genotyping, DNA was isolated from whole blood using a commercial kit (Nucleo-Spin, Macherey & Nagel, Düren, Germany). The tagging SNPs were genotyped using the mass spectrometry system massARRAY from Sequenom and the manufacturer's iPLEX software (Sequenom, Hamburg, Germany). The call rates were ≥96.1%. The mass spectrometric results were validated in 50 randomly selected subjects by bidirectional sequencing, and both methods gave 100% identical results.

Statistical Analyses.

Continuous variables with non-normal distribution were loge-transformed prior to statistical analysis. Multiple linear regression analysis was performed using the least-squares method. In the regression models, insulin secretion was chosen as outcome variable, the SNP genotype (in the dominant inheritance model) as independent variable and gender, age, BMI, and insulin sensitivity as confounding variables. SNP-BMI interaction effects on insulin secretion were tested by analysis of covariance (ANCOVA) with gender, age, and insulin sensitivity as confounding variables. When testing all seven tagging SNPs in parallel, a Bonferroni-corrected p-value<0.0073 was considered statistically significant. For all analyses, the statistical software JMP 8.0 (SAS Institute, Cary, N.C., USA) was used.

EXAMPLE 5: LOSS OF FLTP MAKES β CELLS MORE SUSCEPTIBLE TO STREPTOZOTOCIN TREATMENT

To further test the requirement of PCP and Fltp in the context of β cell survival and regeneration, a multiple low-dose streptozotocin (STZ) model was employed (Kolb 1987). Streptozotocin is a naturally occurring chemical that is particularly toxic to β cells. For this purpose STZ was injected on five consecutive days and blood glucose regulation was measured every $2^{nd}$ day thereafter in Fltp$^{ZV/+}$ and Fltp$^{ZV/ZV}$ cohorts (FIG. 5C). This revealed that blood glucose control and β cell function gradually decreased in a Fltp-dose dependent manner until day 16 after the first injection. An ipGTT performed at day 16 after the first STZ injection revealed that Fltp$^{ZV/ZV}$ mice were significantly more glucose intolerant when compared to Fltp$^{ZV/+}$ littermates (FIG. 5B). The gradual loss of β cells was confirmed by immunohistochemistry on pancreatic sections from vehicle and STZ-treated animals (FIG. 5A), which at the stage analyzed did not show any signs of β cell regeneration. Thus, loss of Fltp and planar polarization in β cells increases the vulnerability to STZ.

EXAMPLE 6: MOLECULAR PROFILING REVEALS INCREASED MATURATION STATE OF FLTP REPORTER EXPRESSING β CELLS

The data presented so far clearly indicated that Fltp-mediated planar polarization subdivided β cells into proliferative and into more mature β cells. To better understand these PCP-mediated differences on the molecular level, use was made of the Fltp::H2B-Venus reporter. Adult islets were purified from animals under physiological homeostatic conditions and the Fltp reporter negative and Fltp reporter expressing endocrine subpopulations were isolated using fluorescent activated cell sorting (FACS; FIGS. 6A&B). The purity of the Fltp reporter negative and Fltp reporter expressing endocrine cell populations were controlled by cytospins and reached almost 100% for the Venus fluorescent marker and approx. 80% of both populations were β cells (marked by Nkx6.1) (FIG. 6C).

The Fltp reporter negative and Fltp reporter expressing endocrine subpopulations showed markedly different levels of mRNA expression after cDNA amplification and expression profiling using Affymetrix gene arrays (FIG. 6D). 1887 genes are up- and 1800 genes are more than 1.5-fold significantly (p<0.005) down-regulated. Strikingly, unbiased gene ontology (GO) term analysis revealed that the Ftp reporter negative population shows a significant enrichment of genes that associate with cell proliferation, actin binding, Wnt/PCP-, TGF receptor-, G-protein coupled receptor-, ERK-signaling transduction, whereas the Fltp reporter expressing population shows significant enrichment of genes that are important for mature beta cell function, such as genes involved in metabolic processes, glucose metabolism, mitochondria and insulin secretion (FIG. 6E).

Taken together, the molecular profiling of Fltp reporter negative and Fltp reporter expressing endocrine populations clearly revealed that Fltp reporter negative cells constitute a population of low polarized more naïve progenitor cells, whereas the Fltp reporter negative cells are highly polarized, more mature and express higher levels of glycolysis enzymes, polarity markers and signaling receptors for major β cell regulatory pathways.

EXAMPLE 7: FLTP REPORTER NEGATIVE β CELL PROGENITORS DIRECTLY GIVE RISE TO FLTP REPORTER EXPRESSING MATURE BETA CELLS

To directly test whether Fltp reporter negative β cells are progenitors of Fltp reporter expressing β cells, a Cre recombinase/loxP-mediated genetic lineage tracing approach was used. To this end, the previously established Fltp-T2A-iCre mouse line (Lange, Gegg et al. 2012) was crossed to the mTmG reporter mouse line (Muzumdar, Tasic et al. 2007). Upon Fltp promoter-driven Cre expression, the membrane Tomato (mT) fluorescent reporter gene switches to membrane GFP (mG), which is irreversible and therefore allows cell fate analysis.

Islets of these crossings were isolated and cultured in vitro. To establish the culture conditions, it is first tested if β cells depend on Wnt/PCP signaling to maintain Ftp reporter expression. Therefore, islets were cultured in absence or presence of ligands of the canonical Wnt/β-catenin (Wnt3a) and non-canonical Wnt/PCP pathway (Wnt5a). These experiments indicated that Fltp-reporter gene expression indeed depend on Wnt/PCP, but not canonical Wnt signaling. Using these culture conditions in combination with live single cell imaging will allow us to follow new born Fltp-Cre expressing mT and mG expressing cells over a time-course of two to four days. Single-cell tracking over this time period and later fixation and staining for the β cell marker Nkx6.1 clearly revealed that mT expressing cells (Ftp negative) cells give rise to mG expressing cells (Fltp expression), suggesting that adult islets contain a Fltp negative low polarized and highly proliferative progenitor population, which can give rise to Wnt/PCP-dependent highly polarized and less proliferative Fltp expressing mature 1 cell population.

EXAMPLE 8: NKX6.1 EXPRESSING 1 CELL PROGENITORS FORM CORD-LIKE STRUCTURES WHICH LATER ARRANGE IN ISLETS OF LANGERHANS

Analysis of Nkx6.1 expressing β cells in whole-mount stained and BABB cleared pancreata at E18.5 show cord-like structures. During post-natal maturation period they become compacted 3D structures. The Fltp reporter is absent in b cells located in cord-like structures compared to islets. Together with the increased Fltp reporter expression during maturation (FIG. 1B) and the change in morphology of cord-like structures to islets indicate that Fltp expression is connected with islets formation.

EXAMPLE 9: KNOCK-IN/KNOCK-OUT OF LACZ AND H2B-VENUS INTO THE FLTP LOCUS

To explore Fltp expression and function in vivo, a Fltp$^{ZV}$ knock-in/knock-out allele was generated where the entire ORF was replaced by a multicistronic lacZ-Venus reporter cassette. This contained a nuclear localization signal (NLS)-tagged β-Galactosidase (lacZ reporter gene followed by an intervening viral Thosea Asigma 2A-peptide (T2A) for co-translational cleavage and a very bright Histone 2B(H2B)-Venus fluorescent reporter gene. Southern and western blot analysis confirmed the targeted homologous recombination and generation of a null allele. The knock-in/knock-out construct was designed as shown in FIG. 9. 5' and 3' HR for the Fltp gene were amplified by PCR (449 fwd 5' HR AscI: 5'-NNNGGCGCGCCAGTCAGGAAGTG-GAAGAGAAGAACACAG-3': 450 rev 5' HR HindIII, SpeI: 5'-NNNAAGCTTACTAGTGTGGTG-GAGTGCCTGTCTACATGTG-3'; 451 fwd 3' HR HindIII: 5'-NNNAAGCTTCACGACAGT-CAAAGCTGCAATAGAAC-3'; 452 rev 3' HR BamHI: 5'-NNNGGATCCGGTAATTTGGCAAT-TATAGAACTCAGGC-3') using a C57BL/6J BAC clone (RP23-333P11) as template. These two PCR products were subcloned into the pL254 vector (Liao, Uetzmann et al. 2009) using AscI and BamHI. The resulting vector was digested with HindIII, SpeI and electroporated into electro-competent EL350 bacteria containing the Fltp BAC clone to retrieve the WT sequence between PCR homology arms resulting in the Fltp retrieval vector. For cloning of the knock-in/knock-out cassette in pBKS-5' and 3' HR for the knock-in into the ATG of exon two of Fltp were generated by PCR (453 fwd 5' HR SacII: 5'-NNNCCGCGGAGCA-GACTTAACTATGTTGGGGAAACAGC-3'; 454 rev 5' HR SalI, NotI: 5'-NNNGTCGACGCGGCCGCTGTTTA-CACTTGTTGCCTGGCAACTG-3'; 455 fwd 3' HR SalI: 5'-NNNGTCGACGGTCCTAGTCTAGCTGAGGTCCA-GATC-3'; 456 rev 3' HR KpnI: 5'-NNNGGTAC-CATGCTGTGGGAGTCACTGACATTCTTG-3) using the previously mentioned BAC as a template and subcloned into pBKS-using the introduced restriction sites, resulting in pBKS-Fltp-HomArms. The first step to generate the targeting vector was to construct the pBKS-H2B-Venus-intron-SV40 pA plasmid by subcloning an oligonucleotide for the H2B (histone 2B) that introduces a 5' NotI and a perfect Kozak sequence (025: 5'-NNNGCGGCCGCGCCAC-CATGCCAGAGCCAGCG-3') and a 3' XbaI site (026: 5'-NNNTCTAGACTTAGCGCTGGTGTACTTGGT-GATGG-3'). This PCR product was ligated into pBKS-(both cut with NotI, XbaI) resulting in pBKS-H2B. The next step was to introduce the Venus reporter gene (yellow fluorescent protein) also via PCR with the forward (fwd) primer containing an XbaI site (013: 5'-NNNTCTAGAATGGT-GAGCAAGGGCGAGGAGCTGTTC-3') and a reverse (rev) primer containing a SpeI site (014: 5'-NN-NACTAGTTTACTTGTACAGCTCGTC-CATGCCGAGAG-3'). This PCR and the vector pBKS-H2B were digested with XbaI and SpeI and ligated resulting in pBKS-H2B-Venus. To complete the construct an intron-SV40 pA oligonucleotide was generated by using the fwd primer containing SpeI (011: 5'-NN-NACTAGTAGGTAAGTGTACCCAATTCGCCCTATAG-3') and the rev primer containing BamHI (012: 5'-NNNG-GATCCACGCGTTAAGATACATTGATGAGTTTGGAC-3'). This oligonucleotide was subcloned into pBKS-H2B-Venus by cutting both with SpeI and BamHI resulting in the pBKS-H2B-Venus-intron-SV40 pA plasmid. The next step was to introduce the loxP flanked neomycin (neo) resistance cassette by digesting the PL-452 vector (Liu, Jenkins et al. 2003) with SalI and BamHI. The digested vector was ligated into the pBKS-H2B-Venus-intron-SV40 pA plasmid opened by cutting with SalI and BamHI resulting in pBKS-H2B-Venus-intron-SV40 pA-loxP-bGHpA-neo-EM7-PGK-loxP (pBKS-H2B-Venus-neo). For following cloning steps it was necessary to destroy the MluI site located in the SV40 pA by cutting with MluI, filling up the 5' overhang with Klenow polymerase and religating the vector. The T2A sequence from Thosea asigna virus was introduced into the NotI site of pBKS-H2B-Venus-neo by annealing the following oligos 2A_fwd (5'-GGCCGCACGCGTTT-GAAGGTAGAGGCTCTTTACTAA-CATGCGGCGACGTTGAGGAAAAC CCAGGACC-3) and 2A_rev (5'-GGCCTGGTCCTGGGTTTTCCT-CAACGTCGCCGCATGTTAGTAAAGAGCCTC-TACCTTCAA ACGCGTGC-3), which created a NotI compatible overhang resulting in pBKS-2A-H2B-Venus-neo. To clone the NLS-lacZ (nuclear localisation signal-b-galactosidase fusion protein) in front of the H2B-Venus construct we amplified the NLS-lacZ by PCR out of a NLS-lacZ containing vector. We used the fwd primer 340 (5'-NNNGCGGCCGCGCCACCATGAACCTT-GAAGCTCGAAAAACAAAG-3) with a NotI site at the 5' end and the rev primer 341 (5'-NNNGGCGCGCCTTTTTGACACCAGAC-CAACTGGTAATGGTAGC-3'), containing an AscI site at the 3' end. The PCR product was digested with NotI and AscI and ligated into the NotI and MluI digested pBKS-2A-H2B-Venus- neo vector resulting in pBKS-NLS-lacZ-2A-H2B-Venus-neo. For finishing the minitargeting construct we cloned pBKS-NLS-lacZ-2A-H2B-Venus-neo into pBKS-Fltp-HomArms (both cut with NotI and SalI). The minitargeting construct was cut out by SacII and KpnI, electroporated in EL350 bacteria and introduced into PL254 via bacterial homologues recombination resulting in the final targeting construct (PL254-Fltp-NLS-lacZ-2A-H2B-Venus-intron-SV40 pA-loxP-bGHpA-neo-EM7-PGK-loxP) which was confirmed by sequencing and is ready for electroporating into embryonic stem (ES) cells (after linearization by AscI).

EXAMPLE 10: FLTP-VENUS FUSION KNOCK-IN STRATEGY AND CONFIRMATION

The knock-in construct was designed as shown in FIG. 10. The Ftp retrieval vector was generated as described in example 9.

For cloning of the knock-in cassette in pBKS-5' and 3' HR for the knock-in into the ATG of exon two of Fltp were generated by PCR with following primers: 1228 fwd 5' HR: 5'-NNNGCGGCCGCGGTTGGATTCT-GAGGCTGACTGGG-3', and 1229 rev 5' HR: 5'-NNNTCTAGACTTGGTGCTCTTACAAGGGCTCGG-3', digested with NotI and XbaI; EP1230 fwd 3' HR: 5'-NNNGAATTCGTCCTAGTCTAGCTGAGGTCCA-GATCTATG-3', and EP1231 rev 3' HR: 5'-NN-NAAGCTTGTGGGAGTCACTGACATTCTTGTTAACC-3', digested with EcoRI and HindIII using a C57BL/6J BAC clone (RP23-333P11) as template. The STOP codon of the 5' HR was excluded resulting in a fusion construct with introduced downstream sequences. The 5' and 3' HR PCR products were subcloned into pBKS- using the introduced restriction sites, resulting in a plasmid named pBKS-Fltp-Hom Arms.

To introduce the Venus fusion reporter gene and the 3×FLAG tag into the targeting construct the Venus sequence was amplified from pBKS-Venus vector (Nagai, Ibata et al. 2002) using primers 1126 fwd (5'-GCGGCCGCAGCCAC-CATGTCTAGAAT GGTGAGCAAGGGCGAG-GAGCTGTTC-3') containing an XbaI site and 1201 rev (5'-NNNACTAGTTCACTTGTCATCGT-CATCCTTGTAATCGATGTCATGATCTTTATAAT-CACCG TCATGGTCTTTGTAGTCCTTGTA-CAGCTCGTCCATGCCGAGAGTGATCC-3') containing a SpeI site and the C-terminal 3×FLAG tag sequence. The resulting open reading frame of Venus-3×FLAG was cloned in frame with Fltp sequence into the pBKS-Ftp-HomArms vector after digestion with XbaI and SpeI.

In the next step, the PGK promoter-driven neomycin resistance gene flanked by loxP sites (loxP-bGHpA-neo-EM7-PGK-loxP) was cloned from the PL-452 vector (Liu, Jenkins et al. 2003) via BamHI, EcoRI and subcloned 3' of the Venus-3×FLAG sequence resulting in the pBKS-Ftp-HomArms-Venus-3×FLAG-fusion-loxP-Neo-loxP. Subsequently, the mini-targeting cassette was cut with NotI and HindIII and introduced into the Ftp retrieval vector pL254 via bacterial homologous recombination in EL350 bacteria resulting in final targeting construct pL254-Fltp-Venus-3× FLAG-fusion-loxP-bGHpA-neo-EM7-PGK-loxP. This was confirmed by sequencing. The targeting vector was linearized with AscI and electroporated into ES cells.

EXAMPLE 11: FTP ANTIBODY EPITOPES AND BINDING SPECIFICITY

Ftp antibodies were generated as described previously (Lange, Gegg et al. 2012). To analyze the Fltp protein biochemically and cell biologically, two affinity purified polyclonal antibodies were raised in rabbit (Fftp1, Ftp116-1) against mouse Fltp using the peptide sequence: DNPDEPQSSHPSAGHT for Fftp1 and KPFDPDSQTKQKKSVTKTVQ for Fltp116-1 (Pineda, Berlin, Germany). The Fftp1 epitope lies in the PRR of the less well conserved C terminal part of the Fltp protein (FIG. 11 B). Nevertheless, the human and murine sequences are nearly completely similar. The Fltp116-1 epitope lies N terminal to the Ftp1 epitope and is less conserved in human.

Additional rat monoclonal antibodies (clone #13, #28 and #43) against the human FLTP were prepared using the peptide sequence KPHDPDSQKKLRKKSITKTVQ (FIG. 12). EndoC-β H1 were culture in adherence (2D culture) as described previously (Ravassard et al. (2011) and were stained as follows: cells were fixed for 10 min in 4% paraformaldehyde (PFA) at 37° C., washed 3× with PBS containing 0.2% Tween and 0.3% BSA (washing buffer) at room temperature (RT), and were permeabilized for 30 min on a shaker at RT. Subsequently the cells were washed again 3× with washing buffer at RT, and blocked for 1 h at RT in blocking buffer (PBS including 0.02% Tween, 10% FCS, 0.2% BSA, 3% serum). Then the primary antibody was added in blocking solution and incubated over night at 4° C. The cells were washed 3× in washing buffer, incubated with mouse IgG2b anti Rat IgG2b antibody (dilution 1:2) for 2 h at RT. Then the cells were washed 3× in washing buffer, incubated with donkey anti-mouse IgG 488 (Invitrogen, A21202) (dilution 1:800) for 2 h at RT, washed 3× in washing buffer and embedded in Elvanol for subsequent imaging. Imaging was performed with a Leica SP5 confocal microscope according to the manufacturers guidelines. The 63× glycerol objective was used. FIG. 12A shows that endogenous FLTP protein is localized in the cytoplasm of EndoC-β H1 human f-cells.

For western blotting experiments (see FIG. 12B), HEK293T cells transiently transfected with Flag-tagged FLTP Strep were used, while non-transfected HEK293T cells were used as controls. The human FLTP coding sequence was obtain by PCR using cDNA from EndoC-β H1 human β-cells. The following primers were used:

Forward (NotI)
5'-GCGGCCGCGCCACCATGGCCACTAACTACAGTGCCAAC-3'

Reverse (Eco-Rl)
5'-NNNNGAATTCTAAGGATTTGGCTGGTCTTTGGGGACC-3'.

NotI and Eco-RI restriction enzyme were used to clone human FLTP coding sequence into the pCAG Strep Flag-Tag plasmid and to generate a FLTP Strep Flag-tagged plasmid. HEK 293T were transiently transfected with FLTP Strep Flag-tagged plasmid using polyethylenimine (PEI). For Western blotting, the samples were resuspended in RIPA buffer with protein inhibitor and incubated on ice for 20 min. The cell lysates were centrifuged at 14000 rpm for 30 min at 4° C. and the supernatant containing the protein was collected. Protein concentration was determined by using the Bradford Assay. For each sample, 20 μg of protein were mixed 1:4 with 4×SDS loading buffer with dithiothreitol (DTT) and denatured at 95° C. for 5 min. Proteins were separated on denaturing SDS polyacrylamide gel (10%) at 125V for approximately 1.5 h. The protein was transferred to nitrocellulose membrane by Semi-dry Blot for 30 min at 0.44 mA and 25V. Afterwards, the membrane was incubated in Ponceau-S solution to confirm the successful transfer and washed in PBS-T (PBS+0.2% Tween) to remove the color. The membrane was blocked with 5% milk powder in PBS-T for 2 h. Subsequently, the membrane was incubated with the primary antibody in PBS-T overnight at 4° C. while rolling. After washing the membrane 3× for 10 min with PBS-T, the secondary antibody in PBS-T was added and incubated for 1 h at RT. The membrane was washed again 3× with PBS-T while shaking. The ECL (enhanced chemiluminescent solution) was prepared by mixing solution 1 and 2 at a ratio of 1:1. The membrane was rinsed with the solution before wrapping it into plastic foil and placing it into an X-ray film cassette. The membrane was exposes to a film for 10 s-5 min before the film was developed.

EXAMPLE 12: FLTP MRNA EXPRESSION IN ENDOC-β H1 HUMAN β-CELLS

To investigate FLTP mRNA expression levels in human n-cells cultured under 3D and 2D conditions, EndoC-β H1 human β-cells were cultured in Matrigel (3D) and compared to 2D conditions. EndoC-β H1 human β-cell line was culture in adherence (2D culture) as described previously (Ravassard et al. 2011). For 3D matrigel based cultures, EndoC-β H1 were cultured in Matrigel Matrix Growth Factor Reduced (BD Bioscience, Germany) diluted 1:2 in their respective medium.

For mRNA isolation, the miRNeasy Micro Kit (Qiagen) was used. First, 700 μl QIAzol Lysis Reagent was added to the cell pellet of up to 1 million cells. The sample was disrupted by pipetting and vortexing and incubated for 5 min at RT. 140 μl Chloroform was added to the sample and then vortexed for 15 s and incubated for 3 min at RT. After 15 min of centrifuging at 12,000×g at 4° C., the upper aqueous phase was collected in a new tube. 100% Ethanol was added to 1.5 times volume of the sample and mixed by pipetting. 700 μl of the sample was transferred to the RNeasy Min Elute spin column in a 2 ml collection tube and centrifuged at ≥8000×g for 15 s. The flow through was discarded. The DNase digest was performed by mixing 10 μl DNase1 and 70 μl RDD buffer and pipetting on the membrane of the column and incubated for 15 min at RT. 700 μl Buffer RWT was added to the column and centrifuged for another 15 s at ≥8000×g. The flow-through was discarded, 500 μl RPE Buffer was added and the column was centrifuged for 15 s at ≥8000×g. After discarding the flow-through, 500 μl of 80% ethanol was added and the column was centrifuged for 2 min at ≥8000×g. The flow-through and the collection tube were discarded again and the column was placed in another tube. For drying the membrane, the column was centrifuged at full speed for 5 min with open lid. Flow-through and collection tube were discarded and the column was placed in a new collection tube. The RNA was eluted by placing 14 μl RNase-free water in the center of the membrane and centrifuged at full speed for 1 min to collect the RNA. Purity and concentration of isolated RNA was determined by using nanodrop. For each sample, 1 μg of RNA was synthesized into cDNA by using the Super Script Kit (Invitrogen, Germany). 4 μl of 5× Vilo Reaction Mix and 2 μl of Super Skript Enzyme Mix was added to the RNA and filled up to 20 μl with nuclease-free water. The mixture in the Eppendorf tube was placed into a heat block with the following program: 25° C. 10 min, 42° C. 60 min 85° C. 5 min.

TaqMan qPCR was assessed according with the manufacture instruction and the following probes were used GAPdh Hs-02758991_g1 and (Fltp) C1orf192 Hs01595277_g1.

As is shown in FIG. 13, FLTP mRNA expression in EndoC-β H1 human β-cells is increased when these cells form mini-islets and cellular connections.

EXAMPLE 13: THE EXPRESSION OF FLTP CORRELATES WITH THE EXPRESSION OF OTHER MATURATION Markers and is Induced by Compaction and Addition of the Noncanonical Wnt Ligand Wnt5a To confirm that FLTP is a novel maturation marker for β cells, FLTP expression was correlated with the expression of another maturation marker, namely the maturation marker NKX6.1 in EndoC-β H1 cells (described e.g. in Ravassard et al. 2011), as well as in re-aggregated postnatal islets (Ucn3).

EndoC-β H1 human β-cell line were cultured in adherence (2D culture) as described previously (Ravassard et al. (2011)). For 3D matrigel based cultures EndoC-β H1 were cultured in Matrigel Matrix Growth Factor Reduced (BD Bioscience, Germany) diluted 1:2 in their respective medium. For analysis of WNT5a induced β-cell maturation, samples were stimulated with 400 ng/ml of WNT5a (R&D systems, Germany) for 12 h or 3 days.

Staining of EndoC-β H1 cells was performed as follows: cells were fixed for 10 min in 4% PFA at 37° C. washed 3× with PBS containing 0.2% Tween and 0.3% BSA (washing buffer) at RT, and permeabilized for 30 min on a shaker at RT. Subsequently the cells were washed again 3× with washing buffer at RT, blocked for 1 h at RT in blocking buffer (PBS including 0.02% Tween, 10% FCS, 0.2% BSA, 3% serum). Then the primary antibody was added in blocking solution and incubated over night at 4° C. The cells were washed 3× in washing buffer, incubated with the secondary antibody for 2 h at RT, washed 3× in washing buffer and embedded in Elvanol for subsequent imaging. Imaging was performed with a Leica SP5 confocal microscope according to the manufacturers guidelines. The 63× glycerol objective was used.

Murine pancreatic islets of Langerhans were isolated from 5 day old mice. After decapitation of the animals, the pancreas was dissected and supplemented with collagenase P (1 mg/ml) in HBSS (Hanks balanced salt solution) including 10% BSA (G-solution) and incubated for 15 min at 37° C. The pancreas was washed 2× in G-solution at RT and the islets were picked under the stereomicroscope (Leica). The islets were incubated in RPMI 1640 plus 5% FCS (fetal calf serum) and 1% P/S (penicillin and streptomycin). Afterwards the islets were trypsinized with 0.05% Trypsin 15 at 37° C., washed twice with PBS plus 0.3% BSA and then seeded in iBidi 8 well chambers. For immunohistochemistry the protocol mentioned above was used. Fluorescent intensity was calculated by the Leica LAS-AF (Version 2.7.3.9723) software and the graphs were plotted with Excel.

As is shown in FIGS. 14 and 15, maturation marker expression increases upon compaction of single cells to mini-islets in EndoC-β H1 cells (FIG. 14a-d; FIG. 15a-d).

Taken together, these findings of a correlation of up-regulated FLTP expression and another p cell maturation marker confirm that FLTP is a novel maturation marker for β cell maturation.

To additionally confirm that Wnt/PCP signaling is important for the induction of β-cell maturation, EndoC-β H1 and neonatal isolated islets were stimulated with the noncanonical Wnt ligand Wnt5a. As shown in FIG. 14 e-l and FIG. 15 e-h, Wnt5a stimulation of also resulted in increased expression of maturation markers.

FURTHER REFERENCES

Adams, M. D., Fields, C., Venter, J. C. (1994). "Automated DNA Sequencing and Analysis." Academic Press.
Alphey (1997). "DNA Sequencing: fom experimental methods to bioinformatics." Sorinaer Verlaa Publishing.
Andrikopoulos, S., A. R. Blair, N. Deluca, B. C. Fam and J. Proietto (2008). "Evaluating the glucose tolerance test in mice." *Am J Physiol Endocrinol Metab* 295(6): E1323-1332.
Ayala, J. E., V. T. Samuel, G. J. Morton, S. Obici, C. M. Croniger, G. I. Shulman, D. H. Wasserman and O. P. McGuinness (2010). "Standard operating procedures for describing and performing metabolic tests of glucose homeostasis in mice." *Dis Model Mech* 3(9-10): 525-534.
Baarsma, H. A., M. Konigshoff and R. Gosens (2013). "The WNT signaling pathway from ligand secretion to gene transcription: molecular mechanisms and pharmacological targets." *Pharmacol Ther* 138(1): 66-83.

Bertschinger, J., D. Grabulovski and D. Neri (2007). "Selection of single domain binding proteins by covalent DNA display." *Protein Ena Des Sel* 20(2): 57-68.

Beste, G., F. S. Schmidt, T. Stibora and A. Skerra (1999). "Small antibody-like proteins with prescribed ligand specificities derived from the lipocalin fold." *Proc Natl Acad Sci USA* 96(5): 1898-1903.

Blum, B., S. S. Hrvatin, C. Schuetz, C. Bonal, A. Rezania and D. A. Melton (2012). "Functional beta-cell maturation is marked by an increased glucose threshold and by expression of urocortin 3." *Nat Biotechnol* 30(3): 261-264.

Bonner-Weir, S. (1988). "Morphological evidence for pancreatic polarity of beta-cell within islets of Langerhans." *Diabetes* 37(5): 616-621.

Brenk, R., A. Schipani, D. James, A. Krasowski, I. H. Gilbert, J. Frearson and P. G. Wyatt (2008).

"Lessons learnt from assembling screening libraries for drug discovery for neglected diseases." *Chem Med Chem* 3(3): 435-444.

Cole, S. P. C (1985). "The EBV-Hybridoma Technique and its Application to human Lung Cancer". *Monoclonal Antibodies and Cancer Therapy* 77-96.

Cooper G. M. (2000) "Tools of cell biology." Sinauer Associates, Inc. Eberhard, D. and E. Lammert (2009). "The pancreatic beta-cell in the islet and organ community." *Curr Opin Genet Dev* 19(5): 469-475.

Eiraku, M., N. Takata, H. Ishibashi, M. Kawada, E. Sakakura, S. Okuda, K. Sekiguchi, T. Adachi and Y. Sasai (2011). "Self-organizing optic-cup morphogenesis in three-dimensional culture." *Nature* 472(7341): 51-56.

Eisenberg, E. and E. Y. Levanon (2003). "Human housekeeping genes are compact." *Trends Genet* 19(7): 362-365.

Ezan, J. and M. Montcouquiol (2013). "Revisiting planar cell polarity in the inner ear." *Semin Cell Dev Biol* 24(5): 499-506.

Feldwisch, J. and V. Tolmachev (2012). "Engineering of affibody molecules for therapy and diagnostics." *Methods Mol Biol* 899: 103-126.

Gao, T., B. McKenna, C. Li, M. Reichert, J. Nguyen, T. Singh, C. Yang, A. Pannikar, N. Doliba, T. Zhang, D. A. Stoffers, H. Edlund, F. Matschinsky, R. Stein and B. Z. Stanger (2014). "Pdx1 Maintains beta Cell Identity and Function by Repressing an alpha Cell Program." *Cell Metab* 19(2): 259-271.

Gebauer, M. and A. Skerra (2009). "Engineered protein scaffolds as next-generation antibody therapeutics." *Curr Opin Chem Biol* 13(3): 245-255.

Grabulovski, D., M. Kaspar and D. Neri (2007). "A novel, non-immunogenic Fyn SH3-derived binding protein with tumor vascular targeting properties." *J Biol Chem* 282(5): 3196-3204.

Granot, Z., A. Swisa, J. Magenheim, M. Stolovich-Rain, W. Fujimoto, E. Manduchi, T. Miki, J. K. Lennerz, C. J. Stoeckert, Jr., O. Meyuhas, S. Seino, M. A. Permutt, H. Piwnica-Worms, N. Bardeesy and Y. Dor (2009). "LKB1 regulates pancreatic beta cell size, polarity, and function." *Cell Metab* 10(4): 296-308.

Haque. K., J. Hehir, J. C. Fox, C. R. Newton and S. Little (1998). "Amplification refractory mutation system linear extension: a novel, gel-free, enzyme-linked immunoassay method for DNA genotyping." *Diagn Mol Pathol* 7(5): 248-252.

Harlow, E. and D. Lane (2006). "Bradford assay." *CSH Protoc* 2006(6).

Harlow, E. and D. Lane (1988). "Antibodies, A Laboratory Manual." Cold spring Harbor Laboratory Press.

Harlow, E. and D. Lane (1999). "Using Antibodies, A Laboratory Manual." Cold spring Harbor Laboratory Press.

Heimberg, H., A. De Vos, A. Vandercammen, E. Van Schaftingen, D. Pipeleers and F. Schuit (1993). "Heterogeneity in glucose sensitivity among pancreatic beta-cells is correlated to differences in glucose phosphorylation rather than glucose transport." *Embo J* 12(7): 2873-2879.

Holzgraben and Bechtold (2000). *Deutsche Apotheker Zeituna* 140(8): 813.

Huber, A. B., A. Kania, T. S. Tran, C. Gu, N. De Marco Garcia, I. Lieberam, D. Johnson, T. M. Jessell, D. D. Ginty and A. L. Kolodkin (2005). "Distinct roles for secreted semaphorin signaling in spinal motor axon guidance." *Neuron* 48(6): 949-964.

In't Veld, P. and M. Marichal (2010). "Microscopic anatomy of the human islet of Langerhans." *Adv Exp Med Biol* 654: 1-19.

Kakavas, K. V., A. Noulas, C. Chalkias, C. Hadjichristodoulou, I. Georgiou, E. Georgatsou and S. Bonanou (2006). "Identification of the four most common beta-globin gene mutations in Greek beta-thalassemic patients and carriers by PCR-SSCP: advantages and limitations of the method." *J Clin Lab Anal* 20(1): 1-7.

Kalwat, M. A. and D. C. Thurmond (2013). "Signaling mechanisms of glucose-induced F-actin remodeling in pancreatic islet beta cells." *Ex Mol Med* 45: e37.

Katsuta, H., C. Aguayo-Mazzucato, R. Katsuta, T. Akashi, J. Hollister-Lock, A. J. Sharma, S. Bonner-Weir and G. C. Weir (2012). "Subpopulations of GFP-marked mouse pancreatic beta-cells differ in size, granularity, and insulin secretion." *Endocrinology* 153(11): 5180-5187.

Kohler, G. and C. Milstein (1975). "Continuous cultures of fused cells secreting antibody of predefined specificity." *Nature* 256(5517): 495-497.

Kolb, H. (1987). "Mouse models of insulin dependent diabetes: low-dose streptozocin-induced diabetes and nonobese diabetic (NOD) mice." *Diabetes Metab Rev* 3(3): 751-778.

Kozbor, D. and Roder, J. C. (1983). "The Production of monoclonal antibodies from human lymphocytes." *Immunology today* 4: 72-79.

Kubinyi, H. (1992). "Hansch Analysis and related Approaches." *VCH Verla.*, Weiheim.

Landsman, L., A. Parent and M. Hebrok (2011). "Elevated Hedgehog/Gli signaling causes beta-cell dedifferentiation in mice." *Proc Natl Acad Sci USA* 108(41): 17010-17015.

Lange, A., M. Gegg, I. Burtscher, D. Bengel, E. Kremmer and H. Lickert (2012). "Fltp(T2AiCre): a new knock-in mouse line for conditional gene targeting in distinct mono- and multiciliated tissues." *Differentiation* 83(2): S105-113.

Lawrence, P. A. and J. Casal (2013). "The mechanisms of planar cell polarity, growth and the Hippo pathway: some known unknowns." *Dev Biol* 377(1): 1-8.

Liao, W. P., L. Uetzmann, I. Burtscher and H. Lickert (2009). "Generation of a mouse line expressing Sox17-driven Cre recombinase with specific activity in arteries." *Genesis* 47(7): 476-483.

Lickert, H. (2013). "Betatrophin fuels beta cell proliferation: first step toward regenerative therapy?" *Cell Metab* 18(1): 5-6.

Liu, P., N. A. Jenkins and N. G. Copeland (2003). "A highly efficient recombineering-based method for generating conditional knockout mutations." *Genome Res* 13(3): 476-484.

Masters, J. R. W. (2000). *"Animal cell culture"* Oxford University Press.

Matis, M. and J. D. Axelrod (2013). "Regulation of PCP by the Fat signaling pathway." *Genes Dev* 27(20): 2207-2220.

Melani, C., L. Rivoltini, G. Parmiani, B. Calabretta and M. P. Colombo (1991). "Inhibition of proliferation by c-myb antisense oligodeoxynucleotides in colon adenocarcinoma cell lines that express c-myb." *Cancer Res* 51(11): 2897-2901.

Meng, H., K. Hager. S. A. Rivkees and J. R. Gruen (2005). "Detection of Turner syndrome using high-throughput quantitative genotyping." *J Clin Endocrinol Metab* 90(6): 3419-3422.

Mouratou, B., G. Behar, L. Paillard-Laurance, S. Colinet and F. Pecorari (2012). "Ribosome display for the selection of Sac7d scaffolds." *Methods Mol Biol* 805: 315-331.

Murray, G. I. (2007). "An overview of laser microdissection technologies." *Acta Histochem* 109(3): 171-176.

Muzumdar, M. D., B. Tasic, K. Miyamichi, L. Li and L. Luo (2007). "A global double-fluorescent Cre reporter mouse." *Genesis* 45(9): 593-605.

Nagai, T., K. Ibata, E. S. Park, M. Kubota, K. Mikoshiba and A. Miyawaki (2002). "A variant of yellow fluorescent protein with fast and efficient maturation for cell-biological applications." *Nat Biotechnol* 20(1): 87-90.

Newton, C. R., A. Graham, L. E. Heptinstall, S. J. Powell, C. Summers, N. Kalsheker, J. C. Smith and A. F. Markham (1989). "Analysis of any point mutation in DNA. The amplification refractory mutation system (ARMS)." *Nucleic Acids Res* 17(7): 2503-2516.

Niehrs, C. (2012). "The complex world of WNT receptor signalling." *Nat Rev Mol Cell Biol* 13(12): 767-779.

Pagliuca, F. W. and D. A. Melton (2013). "How to make a functional beta-cell." *Development* 140(12): 2472-2483.

Pan, F. C. and C. Wright (2011). "Pancreas organogenesis: from bud to plexus to gland." *Dev yn* 240(3): 530-565.

Pissard, S., L. T. Huynh. J. Martin and M. Goossens (2002). "HFE genotyping by amplification refractory mutation system-denaturing HPLC." *Clin Chem* 48(5): 769-772.

Puri, S., H. Akiyama and M. Hebrok (2013). "VHL-mediated disruption of Sox9 activity compromises beta-cell identity and results in diabetes mellitus." *Genes Dev* 27(23): 2563-2575.

Quinn. R. J., A. R. Carroll, N. B. Pham, P. Baron, M. E. Palframan, L. Suraweera. G. K. Pierens and S. Muresan (2008). "Developing a drug-like natural product library." *J Nat Prod* 71(3): 464-468.

Ramon, D., M. Braden, S. Adams, F. M. Marincola and L. Wang (2003). "Pyrosequencing trade mark: A one-step method for high resolution HLA typing." *J Transl Med* 1(1): 9.

Ravassard, P., Y. Hazhouz, S. Pechberty, E. Bricout-Neveu. M. Armanet, P. Czernichow and R. Scharfmann (2011). "A genetically engineered human pancreatic beta cell line exhibiting glucose-inducible insulin secretion." *J Clin Invest* 121(9): 3589-3597.

Salomon, D. and P. Meda (1986). "Heterogeneity and contact-dependent regulation of hormone secretion by individual B cells." *Exo Cell Res* 162(2): 507-520.

Sasai, Y. (2013). "Cytosystems dynamics in self-organization of tissue architecture." *Nature* 493(7432): 318-326.

Sawada, A., Y. Nishizaki, H. Sato, Y. Yada, R. Nakayama, S. Yamamoto, N. Nishioka, H. Kondoh and H. Sasaki (2005). "Tead proteins activate the Foxa2 enhancer in the node in cooperation with a second factor." *Development* 132(21): 4719-4729.

Schier, R. and J. D. Marks (1996). "Efficient in vitro affinity maturation of phage antibodies using BIAcore guided selections." *Hum Antibodies Hybridomas* 7(3): 97-105.

Schlatter, D., S. Brack, D. W. Banner, S. Batey, J. Benz, J. Bertschinger, W. Huber, C. Joseph, A. Rufer, A. van der Klooster, M. Weber, D. Grabulovski and M. Hennig (2012). "Generation, characterization and structural data of chymase binding proteins based on the human Fyn kinase SH3 domain." *MAbs* 4(4): 497-508.

Seifert, J. R. and M. Mlodzik (2007). "Frizzled/PCP signalling: a conserved mechanism regulating cell polarity and directed motility." *Nat Rev Genet* 8(2): 126-138.

Smukler, S. R., M. E. Amtfield, R. Razavi, G. Bikopoulos, P. Karpowicz, R. Seaberg, F. Dai. S. Lee, R. Ahrens, P. E. Fraser, M. B. Wheeler and D. van der Kooy (2011). "The adult mouse and human pancreas contain rare multipotent stem cells that express insulin." *Cell Stem Cell* 8(3): 281-293.

Steemers, F. J., W. Chang, G. Lee. D. L. Barker, R. Shen and K. L. Gunderson (2006). "Whole-genome genotyping with the single-base extension assay." *Nat Methods* 3(1): 31-33.

Stefan, Y., P. Meda, M. Neufeld and L. Orci (1987). "Stimulation of insulin secretion reveals heterogeneity of pancreatic B cells in vivo." *J Clin Invest* 80(1): 175-183.

Talchai, C., S. Xuan, H. V. Lin, L. Sussel and D. Accili (2012). "Pancreatic beta cell dedifferentiation as a mechanism of diabetic beta cell failure." *Cell* 150(6): 1223-1234.

Tung, J. W., K. Heydari, R. Tirouvanziam, B. Sahaf, D. R. Parks, L. A. Herzenberg and L. A. Herzenberg (2007). "Modern flow cytometry: a practical approach." *Clin Lab Med* 27(3): 453-468.

Turksen, K. (2004). "Adult Stem cells." Humana Press Inc., Totowa.

Velculescu, V. E., S. L. Madden, L. Zhang, A. E. Lash, J. Yu, C. Rago, A. Lal, C. J. Wang, G. A. Beaudry, K. M. Ciriello. B. P. Cook. M. R. Dufault, A. T. Ferguson, Y. Gao, T. C. He, H. Hermeking, S. K. Hiraldo, P. M. Hwang, M. A. Lopez, H. F. Luderer, B. Mathews, J. M. Petroziello, K. Polyak, L. Zawel. K. W. Kinzler and et al. (1999). "Analysis of human transcriptomes." *Nat Genet* 23(4): 387-388.

Wallingford, J. B. (2012). "Planar cell polarity and the developmental control of cell behavior in vertebrate embryos." *Annu Rev Cell Dev Biol* 28: 627-653.

Wallingford, J. B. and B. Mitchell (2011). "Strange as it may seem: the many links between Wnt signaling, planar cell polarity, and cilia." *Genes Dev* 25(3): 201-213.

Wang, Y. and J. Nathans (2007). "Tissue/planar cell polarity in vertebrates: new insights and new questions." *Development* 134(4): 647-658.

Weedon, M. N., I. Cebola, A. M. Patch, S. E. Flanagan, E. De Franco, R. Caswell, S. A. Rodriguez-Segui, C. Shaw-Smith, C. H. Cho, H. Lango Allen, J. A. Houghton, C. L. Roth, R. Chen, K. Hussain, P. Marsh, L. Vallier, A. Murray, S. Ellard, J. Ferrer and A. T. Hattersley (2014). "Recessive mutations in a distal PTF1A enhancer cause isolated pancreatic agenesis." *Nat Genet* 46(1): 61-64.

Weidle, U. H., J. Auer. U. Brinkmann, G. Georges and G. Tiefenthaler (2013). "The emerging role of new protein scaffold-based agents for treatment of cancer." *Cancer Genomics Proteomics* 10(4): 155-168.

Yang, Y. (2012). "Wnt signaling in development and disease." *Cell Biosci* 2(1): 14.

The invention claimed is:

1. A method of identifying a compound suitable for differentiating immature progenitor β cells into mature β cells, the method comprising:
   (a) contacting a cell population comprising immature progenitor β cells with a test compound; and
   (b) subsequently determining the presence or expression level of the biomarker Flattop (Fltp) in the β cells comprised in the cell population;

wherein the presence of Fltp, or an increased expression level of Fltp, in the β cells comprised in the cell population after the contacting with the test compound is indicative of a compound suitable for differentiating immature progenitor β cells into mature β cells, and wherein
   (i) an Fltp fusion protein comprising a detectable moiety is used for determining the presence, absence, or expression level of Fltp, and wherein the expression of Fltp leads to concomitant expression of the detectable moiety; or
   (ii) a detectable Fltp reporter protein is used for determining the presence, absence, or expression level of Fltp, and wherein the expression of the detectable reporter protein is under the control of the Fltp promoter.

2. The method according to claim 1, wherein the test compound is a compound that activates planar cell polarity (PCP).

3. The method according to claim 2, wherein the compound that activates planar cell polarity (PCP) is an activator of the non-canonical Wnt/PCP pathway.

4. The method of claim 1, wherein
a) the detectable moiety is selected from a Tag, a luminescent marker, a fluorescent marker, fluorescent proteins, or an enzymatic marker; or
b) the reporter protein is selected from a luminescent marker, a fluorescent marker, fluorescent proteins, or an enzymatic marker.

5. The method of claim 4, wherein
I) in the detectable moiety
  a) the tag is His-tag, FLAG-tag, TAP-tag, or myc-tag;
  b) the luminescent or fluorescent marker is luciferase, bacterial luciferase (luxAB), *Photinus* luciferase, or *Renilla* luciferase;
  c) fluorescent protein is green fluorescent protein (GFP), enhanced GFP (EGFP), yellow fluorescent protein (YFP), improved Venus fluorescent protein, red fluorescent protein (RFP), cyan fluorescent protein (CFP), coral-derived photoproteins, DSRed, HcRed, AmCyan, ZsGreen, ZsYellow, or AsRed;
  d) the enzymatic marker is β-galactosidase, CAT, ß-glucuronidase, ß-xylosidase, XylE (catechol dioxygenase), TreA (trehalase), alkaline phosphatase, or secreted alkaline phosphatase; or
  e) the Fltp fusion protein is a Flattop-Venus fusion protein generated by directly fusing the Venus fluorescent protein to the open reading-frame of Flattop; and
II) in the reporter protein
  a) the luminescent or fluorescent marker is luciferase, bacterial luciferase (luxAB), *Photinus* luciferase, or *Renilla* luciferase;
  b) fluorescent protein is green fluorescent protein (GFP), enhanced GFP (EGFP), yellow fluorescent protein (YFP), improved Venus fluorescent protein, red fluorescent protein (RFP), cyan fluorescent protein (CFP), coral-derived photoproteins, DSRed, HcRed, AmCyan, ZsGreen, ZsYellow, or AsRed; or
  c) the enzymatic marker is β-galactosidase, CAT, ß-glucuronidase, ß-xylosidase, XylE (catechol dioxygenase), TreA (trehalase), alkaline phosphatase, or secreted alkaline phosphatase.

6. The method of claim 1, wherein the reporter protein is expressed
a) instead of Fltp expression; or
b) in addition to Fltp expression.

7. A method of identifying a compound suitable for preventing the de-differentiation of mature β cells, the method comprising:
(a) culturing a cell population comprising mature β cells in the presence of a test compound, wherein the cells are cultured under conditions that induce the de-differentiation of said mature β cells; and
(b) subsequently determining the expression level of the biomarker Flattop (Fltp) in the β cells cultured in step (a), wherein an expression level of Fltp determined in step (b) that is substantially identical to the expression level of Fltp in the cell population comprising mature β cells prior to the culture in step (a) is indicative of a compound suitable for preventing the de-differentiation of mature β cells,
wherein
(i) an Fltp fusion protein comprising a detectable moiety is used for determining the expression level of Fltp, and wherein the expression of Fltp leads to concomitant expression of the detectable moiety; or
(ii) a detectable Fltp reporter protein is used for determining the expression level of Fltp, and wherein the expression of the detectable reporter protein is under the control of the Fltp promoter.

8. The method according to claim 7, wherein the test compound is a compound that activates planar cell polarity (PCP).

9. The method according to claim 8, wherein the compound that activates planar cell polarity (PCP) is an activator of the non-canonical Wnt/PCP pathway.

10. The method of claim 7, wherein
a) the detectable moiety is selected from a Tag, a luminescent marker, a fluorescent marker, fluorescent proteins, or an enzymatic marker; or
b) the reporter protein is selected from a luminescent marker, a fluorescent marker, fluorescent proteins, or an enzymatic marker.

11. The method of claim 10, wherein
I) in the detectable moiety
  a) the tag is His-tag, FLAG-tag, TAP-tag, or myc-tag;
  b) the luminescent or fluorescent marker is luciferase, bacterial luciferase (luxAB), *Photinus* luciferase, or *Renilla* luciferase;
  c) fluorescent protein is green fluorescent protein (GFP), enhanced GFP (EGFP), yellow fluorescent protein (YFP), improved Venus fluorescent protein, red fluorescent protein (RFP), cyan fluorescent protein (CFP), coral-derived photoproteins, DSRed, HcRed, AmCyan, ZsGreen, ZsYellow, or AsRed;
  d) the enzymatic marker is β-galactosidase, CAT, ß-glucuronidase, ß-xylosidase, XylE (catechol dioxygenase), TreA (trehalase), alkaline phosphatase, or secreted alkaline phosphatase; or
  e) the Fltp fusion protein is a Flattop-Venus fusion protein generated by directly fusing the Venus fluorescent protein to the open reading-frame of Flattop; and
II) in the reporter protein
  a) the luminescent or fluorescent marker is luciferase, bacterial luciferase (luxAB), *Photinus* luciferase, or *Renilla* luciferase;
  b) fluorescent protein is green fluorescent protein (GFP), enhanced GFP (EGFP), yellow fluorescent protein (YFP), improved Venus fluorescent protein, red fluorescent protein (RFP), cyan fluorescent protein (CFP), coral-derived photoproteins, DSRed, HcRed, AmCyan, ZsGreen, ZsYellow, or AsRed; or
  c) the enzymatic marker is β-galactosidase, CAT, ß-glucuronidase, ß-xylosidase, XylE (catechol dioxygenase), TreA (trehalase), alkaline phosphatase, or secreted alkaline phosphatase.

12. The method of claim 7, wherein the reporter protein is expressed
a) instead of Fltp expression; or
b) in addition to Fltp expression.

13. A method for distinguishing mature β cells from immature progenitor β cells, the method comprising:
determining the presence or absence of the biomarker Flattop (Fltp) in a β cell, comprising subjecting the β cell to a process that detects the presence or absence of a Fltp protein or nucleic acid in the β cell;
wherein the presence of the Fltp protein or nucleic acid in the cell indicates that the cell is a mature β cell and wherein the absence of the Fltp protein or nucleic acid in the cell indicates that the cell is an immature progenitor β cell; and
separating the immature progenitor β cells from the mature β cells, wherein
- (i) an Fltp fusion protein comprising a detectable moiety is used for determining the presence or absence of Fltp, and wherein the expression of Fltp leads to concomitant expression of the detectable moiety; or
- (ii) a detectable Fltp reporter protein is used for determining the presence, absence, or expression level of Fltp, and wherein the expression of the detectable reporter protein is under the control of the Fltp promoter.

14. The method according to claim 13, wherein the presence or absence of an Fltp protein or nucleic acid is determined (i) on the nucleic acid level, (ii) on the amino acid level, or (iii) a combination thereof.

15. The method of claim 13, further comprising inducing the expression of Fltp in the cell population comprising immature progenitor cells, wherein the expression of Fltp in the cells is induced in the presence of a compound that induces the non-canonical Wnt/PCP pathway.

16. The method of claim 15, wherein the compound that induces the non-canonical Wnt/PCP pathway is Wnt5a or Wnt4.

17. The method of claim 13, wherein
- a) the detectable moiety is selected from a Tag, a luminescent marker, a fluorescent marker, fluorescent proteins, or an enzymatic marker; or
- b) the reporter protein is selected from a luminescent marker, a fluorescent marker, fluorescent proteins, or an enzymatic marker.

18. The method of claim 17, wherein
I) in the detectable moiety
- a) the tag is His-tag, FLAG-tag, TAP-tag, or myc-tag;
- b) the luminescent or fluorescent marker is luciferase, bacterial luciferase (luxAB), *Photinus* luciferase, or *Renilla* luciferase;
- c) fluorescent protein is green fluorescent protein (GFP), enhanced GFP (EGFP), yellow fluorescent protein (YFP), improved Venus fluorescent protein, red fluorescent protein (RFP), cyan fluorescent protein (CFP), coral-derived photoproteins, DSRed, HcRed, AmCyan, ZsGreen, ZsYellow, or AsRed;
- d) the enzymatic marker is β-galactosidase, CAT, ß-glucuronidase, ß-xylosidase, XylE (catechol dioxygenase), TreA (trehalase), alkaline phosphatase, or secreted alkaline phosphatase or
- e) the Fltp fusion protein is a Flattop-Venus fusion protein generated by directly fusing the Venus fluorescent protein to the open reading-frame of Flattop; and II) in the reporter protein
- a) the luminescent or fluorescent marker is luciferase, bacterial luciferase (luxAB), *Photinus* luciferase, or *Renilla* luciferase;
- b) fluorescent protein is green fluorescent protein (GFP), enhanced GFP (EGFP), yellow fluorescent protein (YFP), improved Venus fluorescent protein, red fluorescent protein (RFP), cyan fluorescent protein (CFP), coral-derived photoproteins, DSRed, HcRed, AmCyan, ZsGreen, ZsYellow, or AsRed; or
- c) the enzymatic marker is β-galactosidase, CAT, ß-glucuronidase, ß-xylosidase, XylE (catechol dioxygenase), TreA (trehalase), alkaline phosphatase, or secreted alkaline phosphatase.

19. The method of claim 13, wherein the reporter protein is expressed
- a) instead of Fltp expression; or
- b) in addition to Fltp expression.

* * * * *

SEQUENCE LISTING

<160> NUMBER OF SEQ ID NOS: 44

<210> SEQ ID NO 1
<211> LENGTH: 800
<212> TYPE: DNA
<213> ORGANISM: Homo sapiens
<220> FEATURE:
<223> OTHER INFORMATION: Flattop (Fltp) nucleic acid

<400> SEQUENCE: 1

```
aaacagcaca agatcatggc cactaactac agtgccaacc agtatgaaaa ggctttctca    60
tccaagtatc tgcagaactg gtctcccact aagccaacaa agagagcat ctcttctcat    120
gaaggctaca ctcaaattat tgccaacgat cgtggtcatc tactgccttc tgtgccccgt    180
tccaaggcaa atccttgggg ttccttcatg ggcacctggc aaatgcctct gaagataccc    240
cctgctcggg tgaccctgac ctcccgtaca actgctggtg ctgcctccct caccaaatgg    300
atacagaaaa atcctgattt actcaaggcc tccaatgggc tgtgtcctga atcttaggc    360
aagccccatg atccagacag tcagaagaaa ctcagaaaga agtctatcac aaagactgta    420
caacaagcac gaagtccaac cataattcca agctccccag ctgccaacct caattcccca    480
gatgaactcc aaagctcaca cccctctgca ggtcatactc caggtcccca agaccagcc    540
aaatcctaag agcccacctg gaagtccacg tatgctagaa ctctgggcag ggcctaatct    600
agctgaggtc cagaaataca aacctggaac ttcatatgga ccaagtggcc acacactgaa    660
aaacccgtat agcgactcag tgaaataaac aagagccccc agtcagaact gtgaaacagg    720
gaaattttgg ggtgggagta aaagcaaatt tggaaaataa actttttttt gttgaatctt    780
ttaaaaaaaa aaaaaaaaaa                                                800
```

<210> SEQ ID NO 2
<211> LENGTH: 176
<212> TYPE: PRT
<213> ORGANISM: Homo sapiens
<220> FEATURE:
<223> OTHER INFORMATION: Flattop (Fltp) protein

<400> SEQUENCE: 2

```
Met Ala Thr Asn Tyr Ser Ala Asn Gln Tyr Glu Lys Ala Phe Ser Ser
1               5                   10                  15

Lys Tyr Leu Gln Asn Trp Ser Pro Thr Lys Pro Thr Lys Glu Ser Ile
            20                  25                  30

Ser Ser His Glu Gly Tyr Thr Gln Ile Ile Ala Asn Asp Arg Gly His
        35                  40                  45

Leu Leu Pro Ser Val Pro Arg Ser Lys Ala Asn Pro Trp Gly Ser Phe
    50                  55                  60

Met Gly Thr Trp Gln Met Pro Leu Lys Ile Pro Pro Ala Arg Val Thr
65                  70                  75                  80

Leu Thr Ser Arg Thr Thr Ala Gly Ala Ala Ser Leu Thr Lys Trp Ile
                85                  90                  95

Gln Lys Asn Pro Asp Leu Leu Lys Ala Ser Asn Gly Leu Cys Pro Glu
            100                 105                 110

Ile Leu Gly Lys Pro His Asp Pro Asp Ser Gln Lys Lys Leu Arg Lys
        115                 120                 125

Lys Ser Ile Thr Lys Thr Val Gln Gln Ala Arg Ser Pro Thr Ile Ile
    130                 135                 140

Pro Ser Ser Pro Ala Ala Asn Leu Asn Ser Pro Asp Glu Leu Gln Ser
145                 150                 155                 160
```

Ser His Pro Ser Ala Gly His Thr Pro Gly Pro Gln Arg Pro Ala Lys
            165                 170                 175

<210> SEQ ID NO 3
<211> LENGTH: 1034
<212> TYPE: DNA
<213> ORGANISM: Mus musculus
<220> FEATURE:
<223> OTHER INFORMATION: Flattop (Fltp) nucleic acid

<400> SEQUENCE: 3

| | | | | | |
|---|---|---|---|---|---|
| acctgcttcc | ccctataccc | tcttctcact | tcacgtggac | ttttgttctt | gttgtttggt | 60 |
| tgttgagata | aggcctttct | atgcatccct | gactggcctg | gaacttacta | tgtaaacctg | 120 |
| gttggctcac | atttagaggt | ctgactcctc | caagttctga | gagagaaagg | aagagggtag | 180 |
| tgtaaaccac | agaatgtagc | ccaaccctg | ctgaccggga | gtaactccca | gaaggctggc | 240 |
| cttctgcagt | tgccaggcaa | caagtgtaaa | cagcactgga | tcatggccac | taactacagt | 300 |
| gccaaccagt | atgaaaaagc | ttacttaccc | acgtacctgc | agaactggtc | tcctgccagg | 360 |
| ccaacgaaag | agaaaatcgc | tgcccatgaa | ggttacactc | agatcatcgc | caacgatcga | 420 |
| gggcatctct | tgccttcagt | gccccgttcc | aaggcaagtc | cttggggttc | cttcatgggc | 480 |
| acctggcaaa | tgcccctgaa | gatcccacct | gctaaggtga | ccttgaccgc | ccgtacaact | 540 |
| acagctgccg | acaacctcac | caaatggata | cacaagaatc | ctgatctact | caacgcctgt | 600 |
| aatgggctgc | gtcctgaaat | ctcaggcaag | cccttcgatc | ctgacagtca | gacgaaacag | 660 |
| aagaaatctg | tcaccaagac | tgtacaacaa | gcaccaaatc | caaccataat | tcccagctcc | 720 |
| ccggttatcc | aaggagacaa | cccagatgaa | ccgcaaagct | cgcacccctc | tgcaggtcac | 780 |
| actccaggtc | cccaaactcc | agtcaactct | cccaacaacc | cacctccgag | cccttgtaag | 840 |
| agcaccaagt | aggtcctagt | ctagctgagg | tccagatcta | tgccatgctg | gggtgacatt | 900 |
| ttagagactg | accgaaatag | gtgagaccct | gcctgtattc | agaaatgtgg | aacagagaaa | 960 |
| tggtgggcca | ggagtgaagg | cagatttagg | gaaataaaca | ttgtgtgtta | aatcttttac | 1020 |
| tgacctgggt | tttc | | | | | 1034 |

<210> SEQ ID NO 4
<211> LENGTH: 189
<212> TYPE: PRT
<213> ORGANISM: Mus musculus
<220> FEATURE:
<223> OTHER INFORMATION: Flattop (Fltp) protein

<400> SEQUENCE: 4

Met Ala Thr Asn Tyr Ser Ala Asn Gln Tyr Glu Lys Ala Tyr Leu Pro
1               5                   10                  15

Thr Tyr Leu Gln Asn Trp Ser Pro Ala Arg Pro Thr Lys Glu Lys Ile
            20                  25                  30

Ala Ala His Glu Gly Tyr Thr Gln Ile Ile Ala Asn Asp Arg Gly His
        35                  40                  45

Leu Leu Pro Ser Val Pro Arg Ser Lys Ala Ser Pro Trp Gly Ser Phe
    50                  55                  60

Met Gly Thr Trp Gln Met Pro Leu Lys Ile Pro Ala Lys Val Thr
65                  70                  75                  80

Leu Thr Ala Arg Thr Thr Thr Ala Ala Asp Asn Leu Thr Lys Trp Ile
                85                  90                  95

His Lys Asn Pro Asp Leu Leu Asn Ala Cys Asn Gly Leu Arg Pro Glu

```
                    100                 105                 110
Ile Ser Gly Lys Pro Phe Asp Pro Asp Ser Gln Thr Lys Gln Lys Lys
        115                 120                 125

Ser Val Thr Lys Thr Val Gln Gln Ala Pro Asn Pro Thr Ile Ile Pro
    130                 135                 140

Ser Ser Pro Val Ile Gln Gly Asp Asn Pro Asp Glu Pro Gln Ser Ser
145                 150                 155                 160

His Pro Ser Ala Gly His Thr Pro Gly Pro Gln Thr Pro Val Asn Ser
                165                 170                 175

Pro Asn Asn Pro Pro Pro Ser Pro Cys Lys Ser Thr Lys
            180                 185

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      Epitope for mouse anti-Fltp antibody

<400> SEQUENCE: 5

Asp Asn Pro Asp Glu Pro Gln Ser Ser His Pro Ser Ala Gly His Thr
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      Epitope for human anti-Fltp antibody

<400> SEQUENCE: 6

Asn Ser Pro Asp Glu Leu Gln Ser Ser His Pro Ser Ala Gly His Thr
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      mP17Rik-116-135 (mouse) peptide

<400> SEQUENCE: 7

Lys Pro Phe Asp Pro Asp Ser Gln Thr Lys Gln Lys Lys Ser Val Thr
1               5                   10                  15

Lys Thr Val Gln
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      mP17Rik-116-135 (human) peptide

<400> SEQUENCE: 8

Lys Pro His Asp Pro Asp Ser Gln Lys Lys Leu Arg Lys Lys Ser Ile
1               5                   10                  15

Thr Lys Thr Val Gln
            20
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer human fltp

<400> SEQUENCE: 9
acctggcaaa tgcctctgaa                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer human fltp

<400> SEQUENCE: 10
ggatcatggg gcttgcctaa                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer human fltp

<400> SEQUENCE: 11
cctgacctcc cgtacaactg                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer human fltp

<400> SEQUENCE: 12
tggatcatgg ggcttgccta                                                   20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer mouse fltp

<400> SEQUENCE: 13
agccatacca catttgtaga gg                                                22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer mouse fltp

<400> SEQUENCE: 14
cagcatggca tagatctgga c                                                 21
```

```
<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer mouse fltp

<400> SEQUENCE: 15
gaggctgact gggaacaatc                                              20

<210> SEQ ID NO 16
<211> LENGTH: 608
<212> TYPE: DNA
<213> ORGANISM: Artificial Sequence
<220> FEATURE:
<223> OTHER INFORMATION: Description of Artificial Sequence: Synthetic
      Fltp 5' Southern probe

<400> SEQUENCE: 16
gagcccttac gcacacttaa gtatgccttt tctttccct agtctctctt tctcttaacc    60
ttcttgtgta aagtttgtca gaagtgttct tcaggagccg gagagacggc aagtactggc  120
acttaacctc ctgagtaccg gttttcattg taggtgtaga tgccaccttg tttaatacag  180
atttaaggac aaatactgaa agatagagag cagcttagga aaatgcagga aacacattac  240
aaacctgagg gtgggtacgg atgtctcaaa agagtaagac cagacactta actgaagtca  300
ctgaatagct tccagtcatt acctttatt atgctatttc tgtgtactca cttgagcaac    360
gtagcctata tctcctcctt gggagaaact gactaaagag gaaatgtcac cggtttcatt  420
atacaaggtg acacaccttc ctcttcattg tcttgggata cacttagaac ccaccatcct  480
gaacatgcta attaaaatgc cctgatagca aataactaa gtaaaattca ttttttttaa    540
aagatatctt ctgagaggcc acacgagact gctcctgcaa cctcagataa gatgcagtta  600
atgtcccg                                                           608

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      5' Southern Fltp FWD primer
<220> FEATURE:
<221> NAME/KEY: modified_base
<222> LOCATION: (1)..(3)
<223> OTHER INFORMATION: a, c, t or g

<400> SEQUENCE: 17
nnnctcgagg agcccttacg cacacttaag                                    30

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      5' Southern Fltp REV primer
<220> FEATURE:
<221> NAME/KEY: modified_base
<222> LOCATION: (1)..(3)
<223> OTHER INFORMATION: a, c, t or g

<400> SEQUENCE: 18
nnntctagac gggacattaa ctgcatctta tctgaggttg                         40
```

```
<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      forward primer for 5' HR AscI for knock-in/knock-out
      construct
<220> FEATURE:
<221> NAME/KEY: modified_base
<222> LOCATION: (1)..(3)
<223> OTHER INFORMATION: a, c, t or g

<400> SEQUENCE: 19
nnnggcgcgc cagtcaggaa gtggaagaga agaacacag                              39

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      reverse primer for 5' HR HindIII, SpeI for knock-in/
      knock-out construct
<220> FEATURE:
<221> NAME/KEY: modified_base
<222> LOCATION: (1)..(3)
<223> OTHER INFORMATION: a, c, t or g

<400> SEQUENCE: 20
nnnaagctta ctagtgtggt ggagtgcctg tctacatgtg                             40

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      forward primer for 3' HR HindIII for knock-in/knock-out
      construct
<220> FEATURE:
<221> NAME/KEY: modified_base
<222> LOCATION: (1)..(3)
<223> OTHER INFORMATION: a, c, t or g

<400> SEQUENCE: 21
nnnaagcttc acgacagtca aagctgcaat agaac                                  35

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      reverse primer for 3' HR BamHI for knock-in/knock-out
      construct
<220> FEATURE:
<221> NAME/KEY: modified_base
<222> LOCATION: (1)..(3)
<223> OTHER INFORMATION: a, c, t or g

<400> SEQUENCE: 22
nnnggatccg gtaatttggc aattatagaa ctcaggc                                37

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
``` forward primer for 5' HR SacII for the knock-in into the
ATG of exon two of Fltp
<220> FEATURE:
<221> NAME/KEY: modified_base
<222> LOCATION: (1)..(3)
<223> OTHER INFORMATION: a, c, t or g

<400> SEQUENCE: 23
nnnccgcgga gcagacttaa ctatgttggg gaaacagc                               38

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      reverse primer for 5' HR SalI, NotI for the knock-in into
      the ATG of exon two of Fltp
<220> FEATURE:
<221> NAME/KEY: modified_base
<222> LOCATION: (1)..(3)
<223> OTHER INFORMATION: a, c, t or g

<400> SEQUENCE: 24
nnngtcgacg cggccgctgt ttacacttgt tgcctggcaa ctg                         43

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      forward primer for 5' HR SalI for the knock-in into the
      ATG of exon two of Fltp
<220> FEATURE:
<221> NAME/KEY: modified_base
<222> LOCATION: (1)..(3)
<223> OTHER INFORMATION: a, c, t or g

<400> SEQUENCE: 25
nnngtcgacg gtcctagtct agctgaggtc cagatc                                 36

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      reverse primer for 3' HR KpnI for the knock-in into the
      ATG of exon two of Fltp
<220> FEATURE:
<221> NAME/KEY: modified_base
<222> LOCATION: (1)..(3)
<223> OTHER INFORMATION: a, c, t or g

<400> SEQUENCE: 26
nnnggtacca tgctgtggga gtcactgaca ttcttg                                 36

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      forward primer for oligonucleotide for the H2B-Histon
<220> FEATURE:
<221> NAME/KEY: modified_base
<222> LOCATION: (1)..(3)
<223> OTHER INFORMATION: a, c, t or g

<400> SEQUENCE: 27

```
nnngcggccg cgccaccatg ccagagccag cg                                    32
```

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      reverse primer for oligonucleotide for the H2B-Histon
<220> FEATURE:
<221> NAME/KEY: modified_base
<222> LOCATION: (1)..(3)
<223> OTHER INFORMATION: a, c, t or g

<400> SEQUENCE: 28

```
nnntctagac ttagcgctgg tgtacttggt gatgg                                 35
```

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      forward primer for Venus reporter gene PCR construct
      containing an XbaI site
<220> FEATURE:
<221> NAME/KEY: modified_base
<222> LOCATION: (1)..(3)
<223> OTHER INFORMATION: a, c, t or g

<400> SEQUENCE: 29

```
nnntctagaa tggtgagcaa gggcgaggag ctgttc                                36
```

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      reverse primer for Venus reporter gene PCR construct
      containing an SpeI site
<220> FEATURE:
<221> NAME/KEY: modified_base
<222> LOCATION: (1)..(3)
<223> OTHER INFORMATION: a, c, t or g

<400> SEQUENCE: 30

```
nnnactagtt tacttgtaca gctcgtccat gccgagag                              38
```

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      forward primer for intron-SV40pA oligonucleotide containing
      an SpeI site
<220> FEATURE:
<221> NAME/KEY: modified_base
<222> LOCATION: (1)..(3)
<223> OTHER INFORMATION: a, c, t or g

<400> SEQUENCE: 31

```
nnnactagta ggtaagtgta cccaattcgc cctatag                               37
```

<210> SEQ ID NO 32
<211> LENGTH: 39
<212> TYPE: DNA
<213> ORGANISM: Artificial Sequence

```
<220> FEATURE:
<223> OTHER INFORMATION: Description of Artificial Sequence: Synthetic
      reverse primer for intron-SV40pA oligonucleotide containing
      an BamHI site
<220> FEATURE:
<221> NAME/KEY: modified_base
<222> LOCATION: (1)..(3)
<223> OTHER INFORMATION: a, c, t or g

<400> SEQUENCE: 32
nnnggatcca cgcgttaaga tacattgatg agtttggac                                39

<210> SEQ ID NO 33
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide 2A_fwd

<400> SEQUENCE: 33
ggccgcacgc gtttgaaggt agaggctctt tactaacatg cggcgacgtt gaggaaaacc         60
caggacc                                                                   67

<210> SEQ ID NO 34
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide 2A_rev

<400> SEQUENCE: 34
ggcctggtcc tgggttttcc tcaacgtcgc cgcatgttag taaagagcct ctaccttcaa         60
acgcgtgc                                                                  68

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      forward primer for nuclear localisation
      signal-b-galactosidase fusion protein (NLS-lacZ) containing
      a NotI site
<220> FEATURE:
<221> NAME/KEY: modified_base
<222> LOCATION: (1)..(3)
<223> OTHER INFORMATION: a, c, t or g

<400> SEQUENCE: 35
nnngcggccg cgccaccatg aaccttgaag ctcgaaaaac aaag                          44

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      reverse primer for nuclear localisation
      signal-b-galactosidase fusion protein (NLS-lacZ) containing
      an AscI site
<220> FEATURE:
<221> NAME/KEY: modified_base
<222> LOCATION: (1)..(3)
<223> OTHER INFORMATION: a, c, t or g

<400> SEQUENCE: 36
```
nnnggcgcgc cttttttgaca ccagaccaac tggtaatggt agc         43

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      forward primer 5' HR for the knock-in cassette into the ATG of
      exon two of Fltp
<220> FEATURE:
<221> NAME/KEY: modified_base
<222> LOCATION: (1)..(3)
<223> OTHER INFORMATION: a, c, t or g

<400> SEQUENCE: 37
nnngcggccg cggttggatt ctgaggctga ctggg         35

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      reverse primer 5' HR for the knock-in cassette into the ATG of
      exon two of Fltp
<220> FEATURE:
<221> NAME/KEY: modified_base
<222> LOCATION: (1)..(3)
<223> OTHER INFORMATION: a, c, t or g

<400> SEQUENCE: 38
nnntctagac ttggtgctct tacaagggct cgg         33

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      forward primer 3' HR for the knock-in cassette into the ATG of
      exon two of Fltp
<220> FEATURE:
<221> NAME/KEY: modified_base
<222> LOCATION: (1)..(3)
<223> OTHER INFORMATION: a, c, t or g

<400> SEQUENCE: 39
nnngaattcg tcctagtcta gctgaggtcc agatctatg         39

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      reverse primer 3' HR for the knock-in cassette into the ATG of
      exon two of Fltp
<220> FEATURE:
<221> NAME/KEY: modified_base
<222> LOCATION: (1)..(3)
<223> OTHER INFORMATION: a, c, t or g

<400> SEQUENCE: 40
nnnaagcttg tgggagtcac tgacattctt gttaacc         37

<210> SEQ ID NO 41
<211> LENGTH: 51
<212> TYPE: DNA
<213> ORGANISM: Artificial Sequence

```
<220> FEATURE:
<223> OTHER INFORMATION: Description of Artificial Sequence: Synthetic
      forward primer for Venus sequence containing an XbaI site

<400> SEQUENCE: 41
gcggccgcag ccaccatgtc tagaatggtg agcaagggcg aggagctgtt c                 51

<210> SEQ ID NO 42
<211> LENGTH: 110
<212> TYPE: DNA
<213> ORGANISM: Artificial Sequence
<220> FEATURE:
<223> OTHER INFORMATION: Description of Artificial Sequence: Synthetic
      reverse primer for Venus sequence containing a SpeI
      site and the C-terminal 3xFLAG tag sequence
<220> FEATURE:
<221> NAME/KEY: modified_base
<222> LOCATION: (1)..(3)
<223> OTHER INFORMATION: a, c, t or g

<400> SEQUENCE: 42
nnnactagtt cacttgtcat cgtcatcctt gtaatcgatg tcatgatctt tataatcacc        60
gtcatggtct ttgtagtcct tgtacagctc gtccatgccg agagtgatcc                   110

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      forward (NotI) primer for human FLTP coding sequence

<400> SEQUENCE: 43
gcggccgcgc caccatggcc actaactaca gtgccaac                                38

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      reverse (Eco-RI) primer for human FLTP coding sequence
<220> FEATURE:
<221> NAME/KEY: modified_base
<222> LOCATION: (1)..(4)
<223> OTHER INFORMATION: a, c, t or g

<400> SEQUENCE: 44
nnnngaattc taaggatttg gctggtcttt ggggacc                                 37
```